US007993824B2

(12) United States Patent
Chappey et al.

(10) Patent No.: US 7,993,824 B2
(45) Date of Patent: Aug. 9, 2011

(54) COMPOSITIONS AND METHODS FOR DETERMINING THE SUSCEPTIBILITY OF A PATHOGENIC VIRUS TO PROTEASE INHIBITORS

(75) Inventors: Colombe Chappey, San Francisco, CA (US); Christos J. Petropoulos, Half Moon Bay, CA (US); Neil T. Parkin, Belmont, CA (US)

(73) Assignee: Monogram Biosciences, Inc., South San Francisco, CA (US)

( * ) Notice: Subject to any disclaimer, the term of this patent is extended or adjusted under 35 U.S.C. 154(b) by 299 days.

(21) Appl. No.: 10/612,603

(22) Filed: Jul. 1, 2003

(65) Prior Publication Data
US 2004/0248084 A1  Dec. 9, 2004

Related U.S. Application Data

(60) Provisional application No. 60/393,248, filed on Jul. 1, 2002, provisional application No. 60/414,273, filed on Sep. 27, 2002.

(51) Int. Cl.
*C12Q 1/70* (2006.01)
*C12Q 1/68* (2006.01)
*G01N 33/00* (2006.01)

(52) U.S. Cl. .................................. 435/5; 435/6; 436/89
(58) Field of Classification Search .................. 435/6
See application file for complete search history.

(56) References Cited

U.S. PATENT DOCUMENTS

| 4,683,195 A | 7/1987 | Mullis et al. |
| 4,683,202 A | 7/1987 | Mullis |
| 4,800,159 A | 1/1989 | Mullis et al. |
| 4,965,188 A | 10/1990 | Mullis et al. |
| 5,436,131 A | 7/1995 | Condra et al. |
| 5,766,842 A | 6/1998 | Melnick et al. |
| 5,837,464 A | 11/1998 | Capon et al. |
| 6,033,902 A | 3/2000 | Haseltine et al. |
| 6,103,462 A | 8/2000 | Paulous et al. |
| 6,242,187 B1 | 6/2001 | Capon et al. |
| 2002/0064838 A1 | 5/2002 | Parkin et al. |
| 2003/0108857 A1 | 6/2003 | Parkin et al. |

FOREIGN PATENT DOCUMENTS

| WO | WO99/67427 | 6/1999 |
| WO | WO00/78996 | 12/2000 |
| WO | WO02/22076 | 3/2002 |
| WO | WO02/068618 | 9/2002 |
| WO | WO02/099387 | 12/2002 |
| WO | WO03/070700 | 8/2003 |
| WO | WO2004/003512 | 1/2004 |
| WO | WO2004/003514 | 1/2004 |

OTHER PUBLICATIONS

Robinson L. HIV Type 1 Protease Cleavage Site Mutations and Viral Fitness: Implications for Drug Susceptibility Phenotyping Assays. AIDS Research and Human Retroviruses 2000, vol. 16, No. 12, pp. 1149-1156.*
Schmidt B. Low Level of Cross-Resistance to Amprenavir (141W94) in Samples from Patients Pretreated with Other Protease Inhibitors. Antimicrobial Agents and Chemotherapy 2000, vol. 44, No. 11, pp. 3213-3216.*
Deeks, S. Novel Four-Drug Salvage Treatment Regimens after Failure of a Human Immunodeficiency Virus Type 1 Protease Inhibitor-Containing Regimen. The Journal of Infectious Diseases 1999, vol. 179, pp. 1375-1381.*
Croteau, G. Impaired Fitness of Human Immunodeficiency Virus Type 1 Variants with High-Level Resistance to Protease Inhibitors. Journal of Virology 1997, vol. 71, No. 2, pp. 1089-1096.*
Jorgensen L. Accession No. CAB94359. [online]. National Center for Biotechnology Information [retrieved on Feb. 2, 2006]. Retrived from the Internet <URL: www.ncbi.nlm.nih.gov/entrez/viewer. fcgi?db=protein&val=8517576>.*
Mascolini M. Revisiting Resistance. IAPAC Monthly Aug. 2000. [online] International Association of Physicians in AIDS Care [retrieved on Feb. 2, 2006]. Retrieved fro the internet <www.iapac. org/home.asp?pid=76&toolid=2&itemid=3317#11>.*
Colonno R. Susceptibility Data on Clinical Isolates: NFV. [online] HIV Drug Reistance Database [retrieved on Feb. 2, 2006]. Retrieved from the internet <URL: hivdb.stanford.edu/cgi-bin/GetResiData. cgi?type=allClinicalPhenotype&drug=NFV&class=PI&pos=84>.*
Beerenwinkel N. Accession No. AAK32197. [online]. National Center for Biotechnology Information [retrieved on Feb. 2, 2006]. Retrived from the Internet <URL: www.ncbi.nlm.nih.gov/entrez/ query.fcgi?db=protein&cmd=search&term=AAK32197>.*
Paulsen et al. Amprenavir and Lopinvir cross-resistance in HIV-1 from subjects failing protease inhibitor therapies. 5th International Workshop on HIV Drug Resistance & Treatment Strategies Jun. 4-8, 2001 Antiviral Therapy vol. 6 Suppl. 1, 51-52.*
Gilden D. Retrovirus Conference Report: Three New Agents to the Rescue [online]. Jan. 1999 [retrieved on Sep. 1, 2010]. Retrieved from the Internet:<URL: http://www.thebody.com/content/treat/ art13551.html>.*
Bowie et al. Deciphering the Message in Protein Sequences: Tolerance to Amino Acid Substitutions. Science, New Series, 1990, vol. 247, No. 4948, pp. 1306-1310.*
Colonno et al. Identification of I50L as the Signature Atazanavir (ATV)-Resistance Mutation in Treatment-Naive HIV-1-Infected Patients Receiving ATV-Containing Regimens. Journal of Infectious Diseases, May 15, 2004, vol. 189, pp. 1802-1810.*
Condra et al., (1996), "Genetic Correlates of In Vivo Resistance to Indinavir, a Human Immunodeficiency Virus Type 1 Protease Inhibitor ," *Journal of Virology*, 70(12): 8270-76.

(Continued)

*Primary Examiner* — Zachariah Lucas
*Assistant Examiner* — Louise Humphrey
(74) *Attorney, Agent, or Firm* — Kilpatrick, Townsend & Stockton

(57) ABSTRACT

The present invention provides an approach for developing an algorithm for determining the effectiveness of anti-viral drugs based on a comprehensive analysis of paired phenotypic and genotypic data guided by phenotypic clinical cut-offs. In one aspect, the algorithm allows one to provide a patient with effective treatment. It helps predict whether an infected individual will respond to treatment with an anti-viral compound, thereby allowing an effective treatment regimen to be designed without subjecting the patient to unnecessary side effects. Also, by avoiding the administration of ineffective drugs, considerable time and money is saved.

35 Claims, 7 Drawing Sheets

OTHER PUBLICATIONS

Genbank Accession No. AF324493 HIV-1 vector pNL4 . . . [gi:12831134] (2001).
Gervaix et al., (1997), "A New Reporter Cell Line to Monitor HIV Infection and Drug Susceptibility in Vitro," *Proc. Natl. Acad. Sci. USA*, 94:4653-4658.
Gong et al., (2000), "In Vitro Resistance Profile of the Human Immunodeficiency Virus Type 1 Protease Inhibitor BMS-232632," *Antimicrobial Agents and Chemotherapy*, 44(9): 2319-26.
Gunthard et al., (1998), "Comparative Performance of High-Density Oligonucleotide Sequencing and Dideoxynucleotide Sequencing of HIV Type 1 *pol* From Clinical Samples", *Aids Research and Human Retroviruses*, 14(10): 869-876.
Haubrich et al., (2001), "CCTG 575: A Randomized. Prospective Study of Phenotype Testing Versus Standard of Care For Patients Failing Antiretroviral Therapy;" *Antiviral Therapy*, 6(Supplement 1): 63.
Herrmann et al., (1997), "A Working Hypotheses-Virus Resistance Development As an Indicator of Specific Antiviral Activity," *Ann. NY Acad Sciences*, 284: 632-637.
Hertogs et al., (1998), "A Rapid Method for Simultaneous Detection of Phenotypic Resistance to Inhibitors of Protease and Reverse Transcriptase in Recombinant Human Immunodeficiency Virus Type 1 Isolates From Patients Treated with Antiretroviral Drugs," *Antimicrobial Agents and Chemotherapy*, 42(2): 269-276.
Hirsch et al., (2000), "Antiretroviral Drug Resistance Testing in Adult HIV-1 Infection," *JAMA*, 283(18): 2417-26.
Katzenstein et al., (2002), "Baseline Phenotypic Susceptibility and Virologic failure over 144 weeks Among Nucleoside RT Inhibitor Experienced Subjects in ACTG 364," Antiretroviral Drug Resistance Testing in Adult HIV-1 Infection, *2002 9$^{th}$ Conference on Retroviruses and Opportunistic Infections*, Session 77 Poster Session 591-T.
Katzenstein et al., (2002), "The Inhibitory Quotient (IQ) for Saquinavir (SQV) Predicts Virologic Response to Salvage Therapy," *2002 9$^{th}$ Conference on Retroviruses and Opportunistic Infections*, Session 28 Poster Session 129.
Maguire et al., (2002), "Emergence of Resistance to Protease Inhibitor Amprenavir in Human Immunodeficiency Virus Type 1-Infected Patients: Selection of Four Alternative Viral Protease Genotypes and Influence of Viral Susceptibility to Coadministered Reverse Transcriptase Nucleoside Inhibitors," *Antimicrobial Agents and Chemotherapy*, 46(3): 731-738.
Petropoulos et al., (2000), "A Novel Phenotypic Drug Susceptibility Assay for Human Immunodeficiency Virus Type 1," *Antimicrobial Agents and Chemotherapy*, 44(4): 920-928.
Int'l Search Report for PCT/US03/21335, May 3, 2004.
Race et al., (1999), "Analysis of HIV Cross-Resistance to Protease Inhibitors Using a Rapid Single-Cycle Recombinant Virus Assay for Patients Failing on Combination Therapies," *AIDS*, 13(15): 2061-2068.
Schuurman et al., (1999), "Worldwide Evaluation of DNA Sequencing Approaches for Identification of Drug Resistance Mutations in the Human Immunodeficiency Virus Type 1 Reverse Transcriptase," *Journal of Clinical Microbiology*, 37(7): 2291-2296.
Shi et al., (1997), "A Recombinant Retroviral System for Rapid In Vivo Analysis of Human Immunodeficiency Virus Type 1 Susceptibility to reverse Transcriptase Inhibitors," *Antimicrobial Agents and Chemotherapy*, 41(12): 2781-85.
Carrillo et al., (1998), "In Vitro Selection and Characterization of Human Immunodefciency Virus Type 1 Variants With Increased Resistance to ABT-378, a Novel Protease Inhibitor," *Journal of Virology*, 72(9): 7532-41.
Craig et al., 1998 "HIV Protease Genotype and Viral Sensitivity to HiV Protease Inhibitors Following Saquinavir Therapy", *AIDS*, 12: 1611-1618.
Dreyer GB, et al."A Symmetric Inhibitor Binds HIV-1 Protease Asymmetrically" *Biochemistry* (1993) 32:937-947.
J. Eron, et al., (1995) Preliminary Assessment of 141 W94 in Combination with Other Protease Inhibitors, *5th Conference on Retroviruses and Opportunistic Infections*.
Genbank Accession No. P12497 POL Polyprotein (2004).

Hazuda, et al., 2000 "Inhibitors of Strand Transfer That Prevent Integration and Inhibit HIV-1 Replication in Cells," *Science* 287: 646-650.
Int'l Search Report for PCT/US00/17178, Dec. 2000.
Int'l Search Report for PCT/US01/28754, Mar. 2002.
Int'l Search Report for PCT/US02/01682, Sep. 2002.
Int'l Search Report for PCT/US02/18684, Jan. 2003.
Int'l Search Report for PCT/US03/04362, Dec. 2004.
Int'l Search Report for PCT/US03/21023, Jul. 2004.
Hill, A. et al. (1998) "Low frequency of genotypic mutations associated with resistance to AZT and 3TC after combination treatment with indinavar," *Int. Conf. AIDS* 12:812, (Abstract No. 6).
Kempf et al., (2001), "Identification of Genotypic Changes in Human Immunodeficiency Virus Protease that Correlate With Reduced Susceptibility to the Protease Inhibitor Lopinavir Among Viral Isolates From Protease Inhibitor-Experienced Patients," *Journal of Virology*, 75(16): 7462-69.
Kim, (1995) "Crystal Structure of HIV-1 Protease in Complex with VX-478, a Potent and Orally Bioavailable Inhibitor of the Enzyme," *J. Am. Chem. Soc.*, 117: 1181-1182.
Lambert DM, et al. (1992) "Human Immunodeficiency Virus Type 1 Protease Inhibitors Irreversibly Block Infectivity of Purified Virions From Chronically Infected Cells" *Anit Microb Agents Chem* 36:982-98.
Larder, et al., (1995) "Potential Mechanism for; Sustained Antiretroviral Efficacy of AZT-3TC Combination Therapy," *Science*, 269; 696-699.
Lazdins, et al., (1997) "In Vitro Effect of al-Acid Glycoprotein on the Anti-Human Immunodeficiency Virus (HIV) Activity of the Inhibitor CGP 61775: A Comparative Study wits Other Relevant HIV Protease Inhibitors," *J Infec. Dis.*, 175: 1063-1070.
Livingston, et al., (1995) "Weak Binding of VX-478 tc Human Plasma Proteins and Implications for Anti-Humar Immunodeficiency Virus Therapy," *J Infec. Dis.*, 172:1.238-124.
Mahalingam, et al., (1999) "Structural and Kinetic Analysis of Drug Resistant Mutants of HIV Protease," *Biochem.*, 263: 1-9.
Miller M, et al. (1989) Structure of Complex of Synthetic HIV-lj Protease with a SubstrateBased Inhibitor at 2.3 A Resolution, *Science* 246:1149-1152.
Mohri H, et al. (1993) "Quantitation of Zidovudine-Resistant Human Immunodeficiency Virus Type 1 in the Blood of Treated and Untreated Patients," *PNAS* 90:25-29.
Murphy, et al., (1999) "Treatment with Amprenavir Alone or Amprenavir with Zidovudine and Lamivudine in Adults with Human Immunodeficiency Virus Infection" *J. Infec. Dis.* 179: 808-81 E.
Najera I, et al. (1994) "Natural Occurrence of Drug ResistancE Mutations in the Reverse Transcriptase of Human Immunodeficiency Virus Type 1 Isolates," *Aids Res Hum Retroviruses* 10:1479-1488.
Najera I, et al. (1995) "pol Gene Quasispecies of Humar Immunodeficiency Virus: Mutations Associated with Drug ResistancE in Virus From Patients Undergoing No Drug Therapy," *J Virol* 69:23-31.
Palmer, et al., (1999) "Highly Drug-resistant HIV-1 Clinical Isolates Are Cross-resistant to Many Antiretroviral Compounds in Current Clinical Development,"*AIDS*, 13: 661-667.
Parkin, et al., (1999) "Phenotypic changes in Drug Susceptibility Associated with Failure of Human Immunodeficiency Virus Type 1 (HIV-1) Triple Combination Therapy," *J Infec. Dis.*, 180: 865-870.
Partaledis, et al., (1995) "In Vitro Selection and Characterization of Human Immunodeficiency Virus Type 1 (HIV-1) Isolates with Reduced Sensitivity to Hydroxyethylamino Sulfonamide Inhibitors of HIV-1 Aspartyl Protease," *Journal of Virology*, 69: 5228-5235.
Patick, et al., (1998) "Genotypic and Pheno typic Characterization of Human Immunodeficiency Virus Type 1 Variants Isolated from Patients Treated with the Protease Inhibitor Nelfinavir," *Antimicrobial Agents and Chemotherapy*, 42(10): 2637-44.
Petit SC, et al. (1993) "The Specificity of the HIV-1 Protease" *Drug Discov Des* 1 :69-83.
Roberts NA, et al. (1990) "Rational Design of Peptide-Based HIV Proteinase" *Science* 248:358361.
Roberts, N. A., (1995) "Drug-resistance patterns of saquinavir and other HIV proteinase inhibitors," *AIDS.9* (supp 2) S27-S32.
Rusconi, Stefano. et al. (2000): "Susceptibility to PNU-140690 (Tipranavir) of Human Immunodeficiency Virus Type 1 Isolates Derived From Patients with Multidrug Resistance to Other Protease Inhibitors," *Antimicrobial Agents and Chemotherapy*, 44(5): 1328-32.

Sadler, et al., (1999) "Safety and Pharmacokinetics of Amprenavir (141W94), a Human Immunodeficiency Virus (HIV) Type 1 Protease Inhibitor, Following Oral Administration of Single Doses to HIV-Infected Adults," *Antimicrobial Agents and Chemotherapy*, 43: 1686-1692.

Sarkar, et al., (1990) "The "Megaprimer"Method of Site-Directed Mutagenesis," *BioTech* 8(4):404-407.

Smidt, et al., (1996) "A Mutation in Human Immunodeficiency Virus Type 1 Protease at Position 88, Located Outside the Active Site, Confers Resistance to the Hydroxyethylurea Inhibitor SC-55389A," *Antimicrobial Agents and Chemotherapy*, 41: 515-522.

St. Clair, et al., (1996) "In Vitro Antiviral Activity of 141 W94 (VX-478) in Combination with Other Antiretroviral Agents," *Antiviral Research* 29: 53-56.

Tian, et al., (1998) "Zidovudine/Lamivudine Co-resistance Is Preceded by a Transient Period of Zidovudine Hypersensitivity," 2nd International Workshop on HIV Drug Resistance and Treatment Strategies, Abstract 30.

Tisdale, M. et al. (1998): "Genotypic and phenotypic analysis of HIV from patients on ZDV/3TC/amprenavir combination therapy," *Int. Conf AIDS* 12:583 (Abstract No. 32312).

Tisdale, M. et al. (1995): "Cross-Resistance Analysis of Human Immunodeficiency Virus Type 1 Variants Individually Selected for Resistance to Five Different Protease Inhibitors," *Antimicro. Agents and Chemo.* 39(8):1704-10.

Tucker, et al., (1998) "Estimate of the Frequency of Human Immunodeficiency Virus Type 1 Protease Inhibitor Resistance Within Unselected Virus Populations In Vitro " *Antimicrobial agents and Chemotherapy*, 42: 478-480.

Young et al. J. Infect. Disease 178(5) 1497-1501 (1998).

Ziermann, et al.,(2000), "A Mutation in Human Immunodeficiency Virus Type 1 Protease, N88S, That Causes In Vitro Hypersensitivity to Amprenavir," *Journal of Virology*, 74(9): 4414-4419.

Andrew Chin, Mar. 9, 2002, "On the Preparation and Utilization of Isolated and Purified Oligonucleotides".

Abravaya, K. et al., "Detection of point mutations with a modified ligase chain reaction (Gap-LCR)," 1995, Nucl. Acids Res., 23:675-682.

Allain, J.-P. et al., "Long-Term Evaluation of HIV Antigen and Antibodies to p24 and gp41 in Patients with Hemophilia," 1987, N. Engl. J. Med., 317:1114-1121.

Altschul, S. et al., "Basic Local Alignment Search Tool," 1990, J. Mol. Biol. 215:403-410.

Altschul, S. et al., "Gapped BLAST and PSI-BLAST: a new generation of protein database search programs," 1997, Nucleic Acids Res., 25:3389-3402.

Barany, F., "Genetic disease detection and DNA amplification using cloned thermostable ligase," 1991, Proc. Natl. Acad. Sci. USA, 88:189-193.

Barre-Sinoussi, F. et al., "Isolation of a T-Lymphotropic Retrovirus from a Pateitn at Risk for Acquired Immune Deficiency Syndrome (AIDS)," 1983, Science, 220:868-871.

Colonno, R. et al., "Identification of 150L as the Signature Atazanavir (ATV)-Resistance Mutation in Treatment-Naïve HIV-1-Infected Patients Receiving ATV-Containing Regimens," The Journal of Infectious Diseases, May 15, 2004; 189:1802-10.

Cotton, R. et al., "Reactivity of cytosine and thymine in single-base-pair mismatches with hydroxylamine and osmium tetroxide and its application to the study of mutations," 1988, Proc. Natl. Acad. Sci. USA, 85:4397-4401.

Current Protocols in Molecular Biology, Ausubel, F.M. et al. eds., John Wiley & Sons, NY, 2010 Table of Contents and list of yearly supplements.

Faham, M. and Cox, D., "A Novel in Vivo Method to Detect DNA Sequence Variation," 1995, Genome Res., 5:474-482.

Fischer, S. and Lerman, L., "DNA fragments differing by single base-pair substitutions are separated in denaturing gradient gels: Correspondence with melting theory," 1983, Proc. Natl. Acad. Sci. USA, 80:1579-83.

Freedman, D., Pisani, R., and Purves, R., 1980, Statistics, W.W. Norton, New York.

Goedert, J. et al., "Effect to T4 Count and Cofactors on the Incidence of AIDS in Homosexual Men Infected With Human Immunodeficiency Virus," 1987, JAMA, 257:331-334.

Gupta, S. et al., "Combinations of Mutations in the Connection Domain of Human Immunodeficiency Virus Type 1 Reverse Transcriptase: Assessing the Impact of Nucleoside and Non-nucleoside Reverse Transcriptase Inhibitor Resistance," May 2010, American Society for Microbiology, vol. 54, No. 5, p. 1973-1980.

Hirsch, M. et al., "Antiretroviral Drug Resistance Testing in Adult HIV-1 Infection: 2008 Recommendations of an International AIDS Society-USA Panel," Jul. 15, 2008, Clinical Infectious Diseases, 47:266-85.

Kan, Y. and Dozy, A., "Antenatal Diagnosis of Sickle-Cell Anaemia by D.N. A. Analysis of Amniotic-Fluid Cells," 1987, The Lancet, 2:910-912.

Karlin, S. and Altschul, S., "Methods for assessing the statistical significance of molecular sequence features by using general scoring schemes," 1990, Proc. Natl. Acad. Sci. USA, 87:2264-2268.

Karlin, S. and Altschul, S., "Applications and statistics for multiple high-scoring segments in molecular sequences," 1993, Proc. Natl. Acad. Sci. USA, 90:5873-5877.

Kellam, P. and Larder, B., "Recombinant Virus Assay; a Rapid, Phenotypic Assay for Assessment of Drug Susceptibility of Human Immunodeficiency Virus Type 1 Isolates," 1994, Antimicrobial Agents and Chemo., 38:23-30.

Landegren, U. et al., "A Ligase-Mediated Gene Detection Technique," 1988, Science, 241:1077-1080.

Lucas, S. "The pathology of HIV infection," 2002, Lepr. Rev., 73:64-71.

Maxam, A. and Gilbert, W., "Sequencing End-Labeled DNA with Base-Specific Chemical Cleavages," 1980, Methods in Enzymology, 65:499-560.

Messing, J. et al., "A system for shotgun DNA sequencing," 1981, Nuc. Acids Res., 9:309-321.

Myers, R. et al., "Detection of Single Base Substitutions by Ribonuclease Cleavage at Mismatches in RNA:DNA Duplexed," 1985, Science, 230-1242-1246.

Nikiforov, T. et al., "Genetic Bit Analysis: a solid phase method for typing single nucleotide polymorphisms," 1994, Nucl. Acids Res., 22:4167-4175.

Norris, T., "HIV Update," 2002, Radiol. Technol., 73:339-363.

Orita, M. et al., "Rapid and Sensitive Detection of Point Mutations and DNA Polymorphisms Using the Polymerase Chain Reaction," 1989, Denomics, 5:874-879.

Orita, M. et al., "Detection of polymorphisms of human DNA by gel electrophoresis as single-strand conformation polymorphisms," 1989, Proc. Natl. Acad. Sci. USA, 86:2766-2770.

Orum, H. et al., "Single base pair mutation analysis by PNA directed PCR clamping," 1993, Nucl. Acids Res., 21:5332-5336.

PCR Strategies, 1995, Innis et al. eds., Academic Press, Inc.

Pearson, W. and Lipman, D., "Improved tools for biological sequence comparision," 1988, Proc. Natl. Acad. Sci. USA, 85:2444-2448.

Piatak, M. et al., "High Levels of HIV-1 in Plasma During All Stages of Infection Determined by Competitive PCR," 1983, Science, 259:1749-1754.

Popovic, M. et al., "Detection, Isolation, and Continuous Production of cytopathic Retroviruses (HTLV-III) from Patients with AIDS and Pre-AIDS," 1984, Science, 224:497-500.

Richman, D., "Resistance, Drug Failure, and Disease Progression," 1994, AIDS Research Hum. Retroviruses 10:901-905.

Russell, W. et al., "Specific-locus test shows ethylnitrosourea to be the most potent mutagen in the mouse," 1979, Proc. Nat. Acad. Sci. USA, 76:5818-5819.

Sambrook et al., 2001, Molecular Cloning : A Laboratory Manual, Cold Spring Harbor Laboratory, 3rd ed., NY.

Sanger, F. et al., "DNA sequencing with chain-terminating inhibitors," 1977, Proc. Natl. Acad. Sci USA, 74:5463-5467.

Southern, E.M., "Detection of Specific Sequences Among DNA Fragments Separated by Gel Electrophoresis," 1975, J. Mol. Biol., 98:503-517.

Syvanen, C. et al., "A Primer-Guided Nucleotide Incorporation Assay in the Genotyping of Apolipoprotein E," 1990, Genomics, 8:684-692.

Thiede, C. et al., "Simple and sensitive detection of mutations in the ras proto-oncogenes using PNA-mediated PCR clamping," 1996, Nucl. Acids Res.,24:983-984.

Torelli, A. and Robotti, C., "ADVANCED and ADAM: two algorithms for the analysis of global similarity between homologous informational sequences," 1994, Comput. Appl. Biosci., 10:3-5.

Urdea, M., "Synthesis and Characterization of Branched DNA (bDNA) for the Direct and Quantitative Detection of CNV, HBV, HCV, and HIV," 1993, Clin. Chem., 39:725-726.

Wagner, R. et al., "Mutation detection using immobilized mismatch binding protein (MutS)," 1995, Nucl. Acids Res., 23:3944-3948.

Whitcomb, J. et al., "Broad Nucleoside Reverse-Transcriptase Inhibitor Cross-Resistance in Human Immunodeficiency Virus Type 1 Clinical Isolates," 2003, J. Infectious Diseases, 188:992-1000.

Youil, R. et al., "Screening for mutations by enzyme mismatch cleavage with T4 endonuclease VII," 1995, Proc. Natl. Acad. Sci USA, 92:87-91.

* cited by examiner

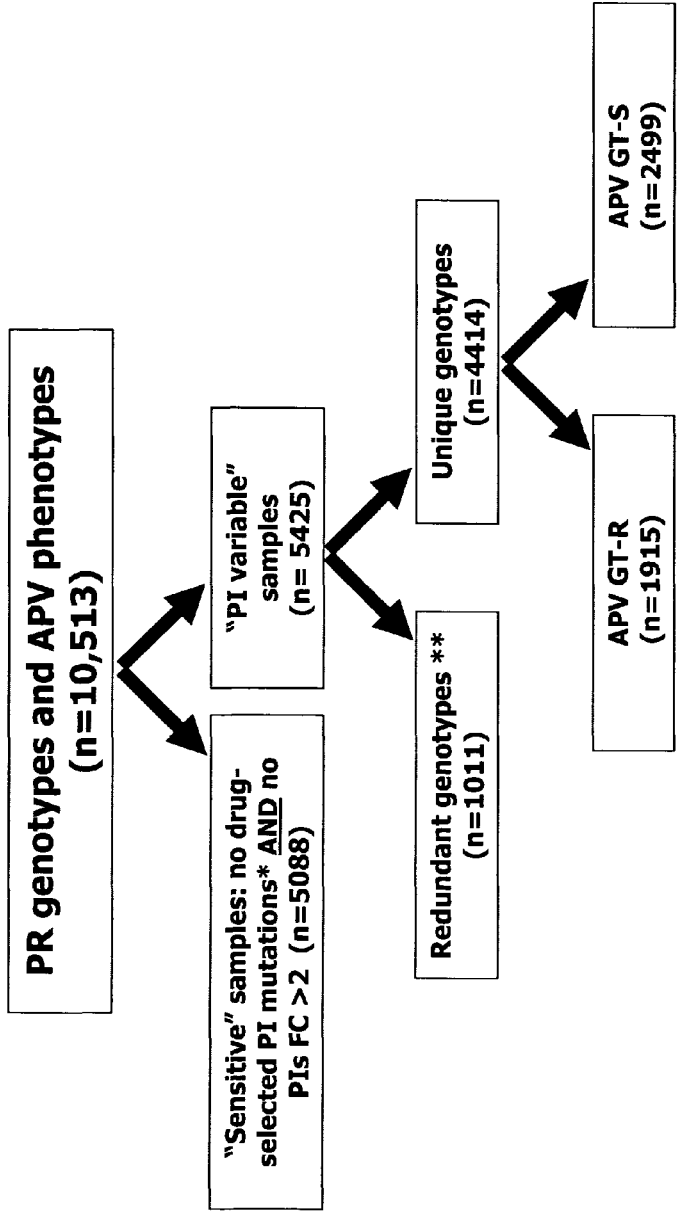

FIGURE 3A

SEQ. ID. NO: 1: NL4-3 HIV Protease Amino Acid Sequence

PQITLWQRPL VTIKIGGQLK EALLDTGADD TVLEEMNLPG RWKPKMIGGI
GGFIKVRQYD QILIEICGHK AIGTVLVGPT PVNIIGRNLL TQIGCTLNF

FIGURE 3B

SEQ. ID. NO: 2: NL4-3 HIV Protease Gene Nucleotide Sequence 1-10   cct cag atc act ctt tgg cag cga ccc ctc 11-20  gtc aca ata aag ata ggg ggg caa tta aag 21-30  gaa gct cta tta gat aca gga gca gat gat 31-40  aca gta tta gaa gaa atg aat ttg cca gga 41-50  aga tgg aaa cca aaa atg ata ggg gga att 51-60  gga ggt ttt atc aaa gta aga cag tat gat 61-70  cag ata ctc ata gaa atc tgc gga cat aaa 71-80  gct ata ggt aca gta tta gta gga cct aca 81-90  cct gtc aac ata att gga aga aat ctg ttg 91-99  act cag att ggc tgc act tta aat ttt

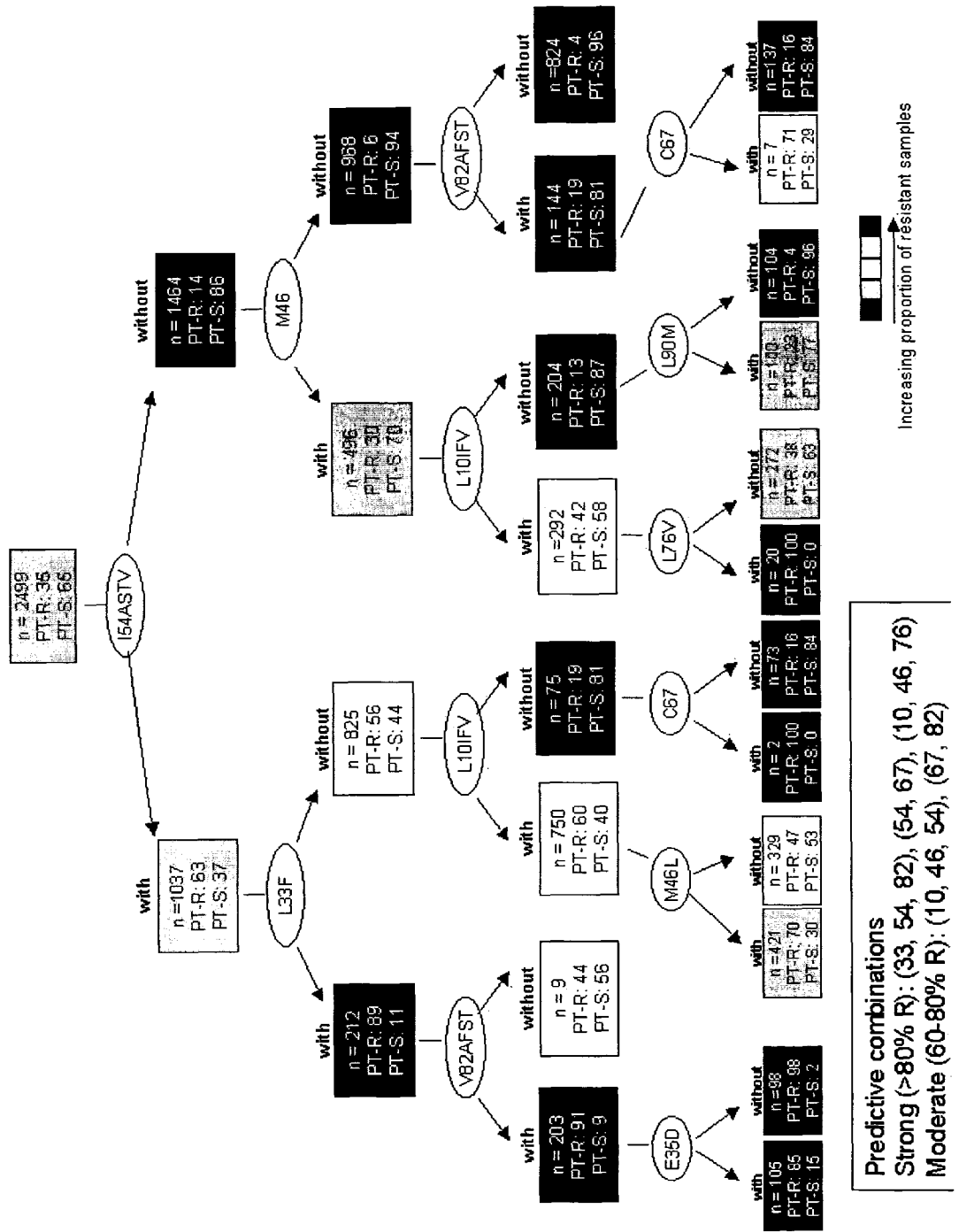

FIGURE 5

COMPOSITIONS AND METHODS FOR DETERMINING THE SUSCEPTIBILITY OF A PATHOGENIC VIRUS TO PROTEASE INHIBITORS

This application is entitled to and claims priority to U.S. Provisional Application Nos. 60/393,248, filed. Jul. 1, 2002; and 60/414,273, filed Sep. 27, 2002, the contents of which are hereby incorporated by reference in their entireties.

1. FIELD OF INVENTION

This invention relates to compositions and methods for determining the susceptibility of a pathogenic virus to an anti-viral compound. The compositions and methods are useful for identifying effective drug regimens for the treatment of viral infections, and identifying and determining the biological effectiveness of potential therapeutic compounds.

2. BACKGROUND OF THE INVENTION

More than 60 million people have been infected with the human immunodeficiency virus ("HIV"), the causative agent of acquired immune deficiency syndrome ("AIDS"), since the early 1980s. See Lucas, 2002, Lepr Rev. 73(1):64-71. HIV/AIDS is now the leading cause of death in sub-Saharan Africa, and is the fourth biggest killer worldwide. At the end of 2001, an estimated 40 million people were living with HIV globally. See Norris, 2002, Radiol Technol. 73(4):339-363.

Modern anti-HIV drugs target different stages of the HIV life cycle and a variety of enzymes essential for HIV's replication and/or survival. Amongst the drugs that have so far been approved for AIDS therapy are nucleoside reverse transcriptase inhibitors such as AZT, ddI, ddC, d4T, 3TC, abacavir, nucleotide reverse transcriptase inhibitors such as tenofovir, non-nucleoside reverse transcriptase inhibitors such as nevirapine, efavirenz, delavirdine and protease inhibitors such as saquinavir, ritonavir, indinavir, nelfinavir, amprenavir and lopinavir.

One consequence of the action of an anti-viral drug is that it can exert sufficient selective pressure on virus replication to select for drug-resistant mutants (Herrmann et al., 1977, Ann NY Acad Sci 284:632-637). With increasing drug exposure, the selective pressure on the replicating virus population increases to promote the more rapid emergence of drug resistant mutants.

With the inevitable emergence of drug resistance, strategies must be designed to optimize treatment in the face of resistant virus populations. Ascertaining the contribution of drug resistance to drug failure is difficult because patients that are likely to develop drug resistance are also likely to have other factors that predispose them to a poor prognosis (Richman, 1994, AIDS Res Hum Retroviruses 10:901-905). In addition, each patient typically harbors a diverse mixture of mutant strains of the virus with different mutant strains having different susceptibilities to anti-viral drugs.

The traditional tools available to assess anti-viral drug resistance are inadequate; the classical tests for determining the resistance of HIV to an anti-viral agent are complex, time-consuming, expensive, potentially hazardous and not custom tailored to the treatment of a given patient. See Barre-Sinoussi et al., 1983, Science 220:868-871; Popovic et al., 1984, Science 224:497-500), and variations of it (see, e.g., Goedert et al., 1987, JAMA 257:331-334; Allain et al., 1987, N. Engl. J. Med. 317:1114-1121; Piatak et al., 1993, Science 259:1749-1754; Urdea, 1993, Clin. Chem. 39:725-726; Kellam and Larder, 1994, Antimicrobial Agents and Chemo. 38:23-30.

Two general approaches are now used for measuring resistance to anti-viral drugs. The first, called phenotypic testing, directly measures the susceptibility of virus taken from an infected person's virus to particular anti-viral drugs. Petropoulos et al., 2000, Antimicrob. Agents Chemother. 44:920-928 and Hertogs et al., 1998, Antimicrob Agents Chemother 42(2):269-76 provide a description of phenotypic assays in widespread use today. Gunthard et al., 1998, AIDS Res Hum Retroviruses 14:869-76 and Schuurman et al., 1999, J Clin Microbiol. 37:2291-96 discuss currently prevalent genotypic assays. Hirsch et al., 2000, JAMA 283:2417-26 provide a general analysis of the currently available assays for testing drug susceptibility.

The second method, called genotypic testing, detects mutations in the virus that affect drug susceptibility and can associate specific genetic mutations with drug resistance and drug failure. Genotypic testing examines virus taken from a patient, looking for the presence of specific genetic mutations that are associated with resistance to certain drugs. Genotypic testing has a few advantages over phenotypic testing, most notably the relative simplicity and speed with which the test can be performed. The testing can take as little as a few days to complete, and because it is less complex, it is somewhat cheaper to perform. However, interpretation of genotypic data is dependent on previous knowledge of the relationships between specific mutations and changes in drug susceptibility.

Efforts to date to use genotypic correlates of reduced susceptibility to predict the effectiveness of anti-viral drugs, especially drugs targeted against the ever-evolving HIV are, at best, imperfect. An algorithm that can more accurately predict whether a given anti-viral drug or combination of drugs would be effective in treating a given patient would save time and money by identifying drugs that are not likely to succeed before they are administered to the patient. More importantly, it would improve the quality of life of the patient by sparing him or her the trauma of treatment with potent toxins that result in no improvement with respect to his or her HIV infection. Therefore, an urgent need exists for a more accurate algorithm for predicting whether a particular drug would be effective for treating a particular patient. Moreover, a genotype based assay can be faster and more cost effective than phenotypic assays.

3. SUMMARY OF THE INVENTION

The present invention provides methods and compositions for developing and using algorithms for determining the effectiveness of an anti-viral therapy or combination of therapies. The algorithms are based on an analysis of paired phenotypic and genotypic data guided by phenotypic clinical cut-offs (the point at which resistance to a therapy begins and sensitivity ends). The algorithms significantly improve the quality of life of a patient by accurately predicting whether a given anti-viral drug would be effective in treating the patient, thereby sparing him or her the trauma of treatment with potent toxins that result in no improvement in his or her HIV infection.

In one aspect, the present invention provides algorithms that allow one to provide a patient with an effective treatment regimen by predicting whether an infected individual will respond to treatment with an anti-viral agent or combination of agents, thereby allowing an effective treatment regimen to be designed without subjecting the patient to unnecessary side effects. Also, by avoiding the administration of ineffective drugs, considerable time and money is saved.

In another aspect, the present invention provides methods for determining the susceptibility of a virus to an anti-viral treatment, comprising detecting, in the viral genome or viral enzymes, the presence or absence of mutations associated with reduced susceptibility to the anti-viral treatment.

In another aspect, the present invention provides methods for determining the effectiveness of an anti-viral treatment of an individual infected with a virus, comprising detecting, in a sample from said individual, the presence or absence of mutations associated with reduced susceptibility to the anti-viral treatment.

The present invention also provides methods of monitoring the clinical progression of viral infection in individuals receiving an anti-viral treatment by determining, as described above, the effectiveness of the same or a different anti-viral treatment.

In one embodiment, the present invention provides nucleic acids and polypeptides comprising a mutation in the protease of a human immunodeficiency virus ("HIV") associated with reduced susceptibility to a protease inhibitor. Examples of protease inhibitors include, but are not limited to, saquinavir, ritonavir, indinavir, nelfinavir, amprenavir and lopinavir.

In one aspect, the invention provides a method for determining whether a human immunodeficiency virus (HIV) has an increased likelihood of having reduced susceptibility to treatment with a protease inhibitor, comprising: detecting whether the protease encoded by said HIV exhibits the presence or absence of one or more HIV protease mutations listed in Table 1; and applying a set of rules to said mutations as provided in Table 4; wherein said HIV has an increased likelihood of being resistant to treatment with said protease inhibitor if said set of rules is satisfied.

In another aspect, the invention provides a method for determining whether an individual infected with a human immunodeficiency virus (HIV) has an increased likelihood of having reduced susceptibility to treatment with a protease inhibitor, comprising: detecting, in a sample from said individual, the presence or absence of one or more HIV protease mutations listed in Table 1; and applying a set of rules to said mutations as provided in Table 4; wherein said individual has an increased likelihood of being resistant to treatment with said protease inhibitor if said set of rules is satisfied.

In another aspect, the invention provides a method for determining whether a HIV has an increased likelihood of having a reduced susceptibility to treatment with a protease inhibitor, comprising: detecting whether the protease encoded by said HIV exhibits the presence or absence of a mutation associated with reduced susceptibility to treatment with said protease inhibitor at amino acid position 11, 32, 33, 34, 43, 46, 47, 48, 50, 54, 58, 71, 76, 79, 82, 83, 84, 91 or 95 of an amino acid sequence of said protease, wherein the presence of said mutation indicates that the HIV has an increased likelihood of having reduced susceptibility to treatment with the protease inhibitor, with the proviso that said mutation is not V32I, M46I, M46L, I47V, I50V, I54L, I54M or I84V.

In another aspect, the invention provides a method of determining whether an individual infected with HIV has an increased likelihood of having a reduced susceptibility to treatment with a protease inhibitor, comprising: detecting, in a sample from said individual, the presence or absence of a mutation associated with reduced susceptibility to treatment with said protease inhibitor at amino acid position 11, 32, 33, 34, 43, 46, 47, 48, 50, 54, 58, 71, 76, 79, 82, 83, 84, 91 or 95 of the amino acid sequence of the protease of the HIV, wherein the presence of said mutation indicates that the individual has an increased likelihood of having reduced susceptibility to treatment with the protease inhibitor, with the proviso that said mutation is not V32I, M46I, M46L, I47V, I50V, I54L, I54M or I84V.

In another aspect, the invention provides a method of determining whether a HIV has an increased likelihood of having a reduced susceptibility to treatment with a protease inhibitor, comprising: detecting whether the protease encoded by said HIV exhibits the presence or absence of a mutation selected from the group consisting of: V11I, V11L, L33F, E34Q, K43T, G48M, I54A, I54S, I54T, Q58E, A71L, L76V, P79, V82A, V82F, N83D, I84A, I84C, T91A, T91S, T91V and C95F, wherein the mutation is associated with reduced susceptibility to treatment with said protease inhibitor and the presence of said mutation indicates that the HIV has an increased likelihood of having reduced susceptibility to treatment with the protease inhibitor.

In a preferred embodiment, the protease inhibitor is amprenavir.

In another preferred embodiment, the human immunodeficiency virus is human immunodeficiency virus type 1 ("HIV-1").

In another aspect, the invention provides an oligonucleotide between about 10 and about 40 nucleotides long encoding a portion of a HIV protease that comprises a mutation at amino acid position 11, 32, 33, 34, 43, 46, 47, 48, 50, 54, 58, 71, 76, 79, 82, 83, 84, 91 or 95 of an amino acid sequence of said protease in said human immunodeficiency virus, wherein the mutation is associated with reduced susceptibility to a protease inhibitor, with the proviso that said mutation is not V32I, M46I, M46L, I47V, I50V, I54L, I54M or I84V.

In another embodiment, the invention provides an isolated polypeptide that comprises at least ten contiguous residues of the amino acid sequence of SEQ ID NO:1, wherein the polypeptide comprises at least one mutation of the invention listed above, and wherein the mutation is associated with reduced susceptibility to a protease inhibitor. In a particular embodiment, the protease inhibitor is amprenavir.

In another embodiment, the polypeptide comprising said mutation or mutations is at least 70%, but less than 100%, identical to a polypeptide having the amino acid sequence of SEQ ID NO:1; the polypeptide has an amino acid sequence that is greater than 80% identical to the amino acid sequence of SEQ ID NO:1; or the polypeptide has an amino acid sequence that is greater than 90% identical to the amino acid sequence of SEQ ID NO:1; wherein the mutation is associated with reduced susceptibility to a protease inhibitor.

In one embodiment, the invention provides a method wherein the presence or absence of a mutation in a protease is detected by hybridization with a sequence-specific oligonucleotide probe to a nucleic acid sequence of human immunodeficiency virus encoding said mutation, wherein the occurrence of hybridization indicates said presence or absence of said mutation.

In another embodiment, the invention provides a method wherein the presence or absence of a mutation in a protease is detected by determining a nucleic acid sequence encoding said mutation.

In another embodiment, the invention provides a method wherein the presence or absence of a mutation in a protease is detected by amplifying the nucleic acid by, for example, polymerase chain reaction.

In one embodiment, the individual is undergoing or has undergone prior treatment with an anti-viral drug. In another embodiment, the anti-viral drug is said or different protease inhibitor.

In one embodiment, the amino acid at position 11 of said protease is an amino acid having a neutral, hydrophobic or non-polar side chain. In another embodiment, the amino acid at position 11 of said protease is I or L. In another embodiment, the amino acid at position 33 of said protease is an amino acid with a neutral, hydrophobic or non-polar side chain. In another embodiment, the amino acid at position 33 of said protease is F. In another embodiment, the amino acid at position 34 of said protease is an amino acid having a neutral, polar or hydrophilic side chain. In another embodiment, the amino acid at position 34 of said protease is Q. In another embodiment, the amino acid at position 43 of said protease is an amino acid with a neutral, hydrophilic or polar side chain. In another embodiment, the amino acid at position 43 of said protease is T. In another embodiment, the amino acid at position 48 of said protease is an amino acid with a neutral, hydrophobic or non-polar side chain. In another embodiment, the amino acid at position 48 of said protease is M. In another embodiment, the amino acid at position 54 of said protease is an amino acid with a neutral, hydrophobic, non-polar, hydrophilic or polar side chain. In another embodiment, the amino acid at position 54 of said protease is an amino acid with a neutral, hydrophobic or non-polar side chain. In another embodiment, the amino acid at position 54 of said protease is A. In another embodiment, the amino acid at position 54 of said protease is an amino acid with a neutral, hydrophilic or polar side chain. In another embodiment, the amino acid at position 54 of said protease is S or T. In another embodiment, the amino acid at position 58 of said protease is an amino acid with an acidic, hydrophilic or polar side chain. In another embodiment, the amino acid at position 58 of said protease is E. In another embodiment, the amino acid at position 71 of said protease is an amino acid with a neutral, hydrophobic or non-polar side chain. In another embodiment, the amino acid at position 71 of said protease is L. In another embodiment, the amino acid at position 76 of said protease is an amino acid with a neutral, hydrophobic or non-polar side chain. In another embodiment, the amino acid at position 76 of said protease is V. In another embodiment, the amino acid at position 79 of said protease is an amino acid with a neutral, hydrophobic, non-polar, acidic, hydrophilic or polar side chain. In another embodiment, the amino acid at position 79 of said protease is an amino acid with a neutral, hydrophobic or non-polar side chain. In another embodiment, the amino acid at position 79 of said protease is an amino acid with an acidic, hydrophilic or polar side chain. In another embodiment, the amino acid at position 79 of said protease is any amino acid, with the proviso that it is not a P. In another embodiment, the amino acid at position 82 of said protease is an amino acid with a neutral, hydrophobic or polar side chain. In another embodiment, the amino acid at position 82 of said protease is A or F. In another embodiment, the amino acid at position 83 of said protease is an amino acid with an acidic, hydrophilic or polar side chain. In another embodiment, the amino acid at position 83 of said protease is D. In another embodiment, the amino acid at position 84 of said protease is an amino acid with a neutral, hydrophobic, non-polar, hydrophilic or polar side chain. In another embodiment, the amino acid at position 84 of said protease is an amino acid with a neutral, hydrophobic or non-polar side chain. In another embodiment, the amino acid at position 84 of said protease is A. In another embodiment, the amino acid at position 84 of said protease is an amino acid with a neutral, hydrophilic or polar side chain. In another embodiment, the amino acid at position 84 of said protease is C. In another embodiment, the amino acid at position 91 of said protease is an amino acid with a neutral, hydrophobic, non-polar, hydrophilic or polar side chain. In another embodiment, the amino acid at position 91 of said protease is an amino acid with a neutral, hydrophobic or non-polar side chain. In another embodiment, the amino acid at position 91 of said protease is A or V. In another embodiment, the amino acid at position 91 of said protease is an amino acid with a neutral, hydrophilic or polar side chain. In another embodiment, the amino acid at position 91 of said protease is S. In another embodiment, the amino acid at position 95 of said protease is an amino acid with a neutral, hydrophobic or non-polar side chain. In another embodiment, the amino acid at position 95 of said protease is F.

In another aspect, the invention provides a method for detecting the presence or absence of a mutation associated with reduced susceptibility to treatment with said protease inhibitor at least 2, 3, 4, 5, 6, 7, 8, 9, 10, 11, 12, 13, 14, 15, 16, 17, 18 or 19 of the amino acid positions.

4. BRIEF DESCRIPTION OF THE FIGURES

FIG. 2 is a flow-chart depicting the steps followed to arrive at a final set of samples that was analyzed in detail.

FIG. 3A shows the amino acid sequence of the NL4-3 HIV (GenBank Accession No. P12497) protease (SEQ. ID. NO: 1).

FIG. 3B shows the nucleic acid sequence for the NL4-3 HIV (GenBank Accession No. AF324493) protease gene (SEQ. ID. NO: 2).

FIG. 4 shows the tree generated by CART analysis of 2499 samples.

Figure 5:
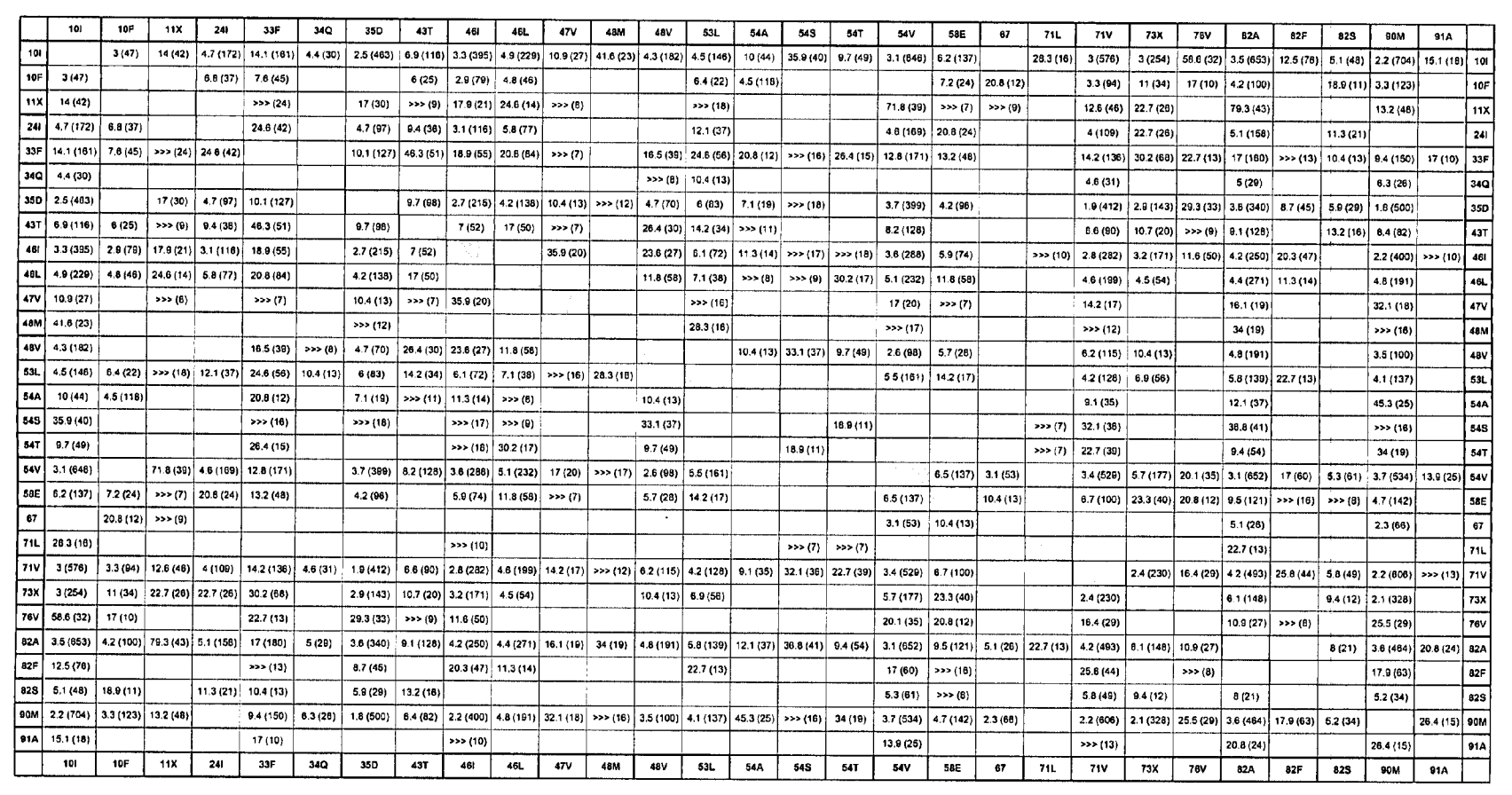

FIG. 5 is a matrix of pairs of mutations associated with amprenavir resistance.

Figure 1:
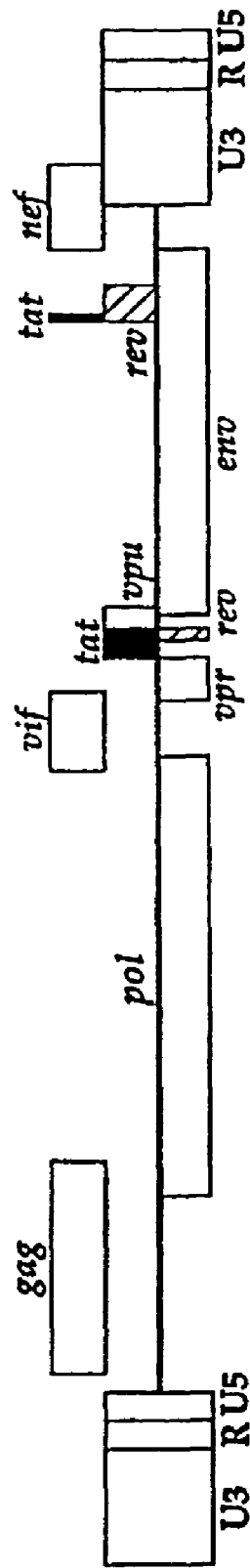
FIG. 1 is a diagrammatic representation of the genomic structure of HIV-1.
Figure 6:
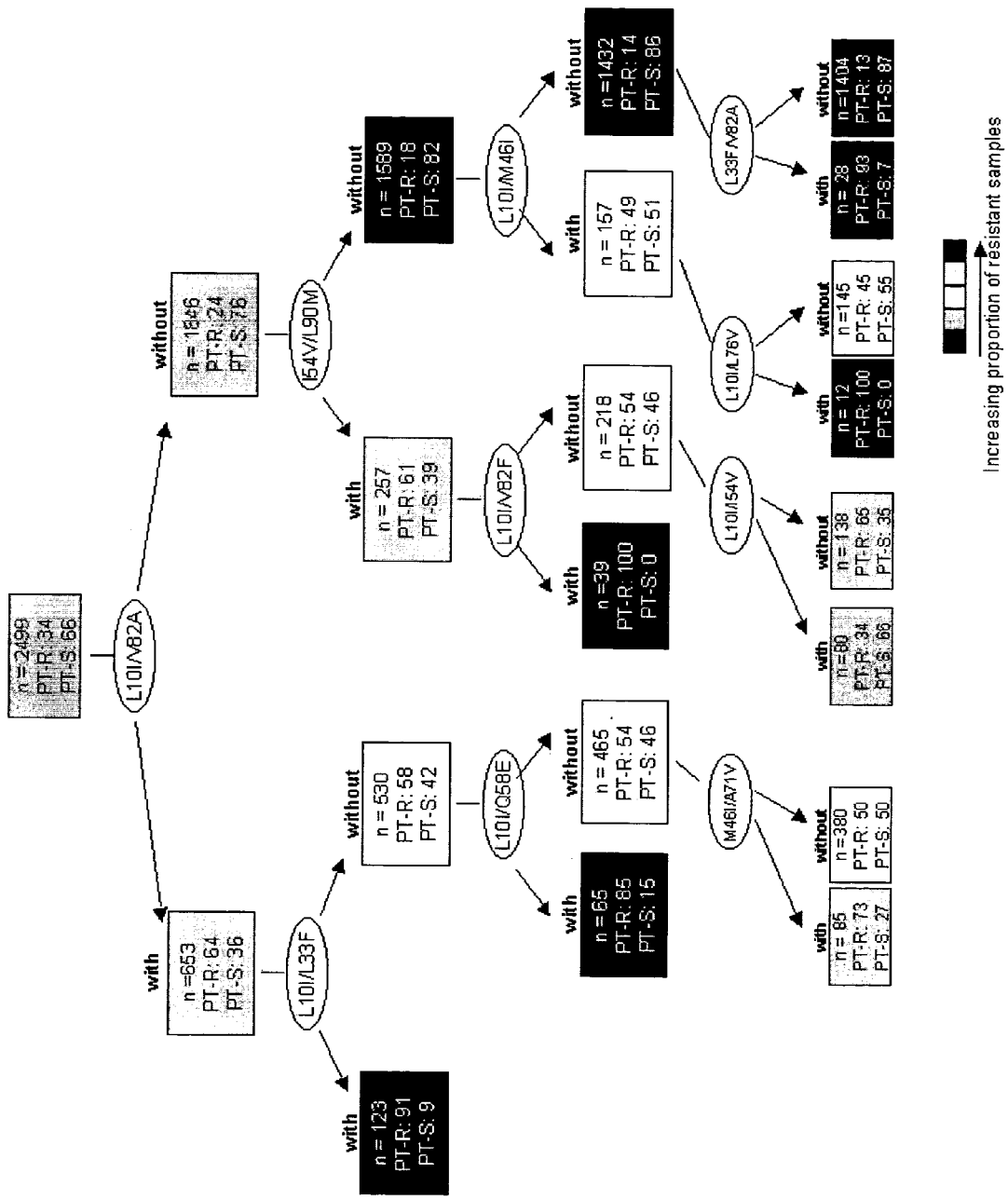

FIG. 6 shows the tree generated by the next round of CART analysis of 2499 samples.

Figure 7:
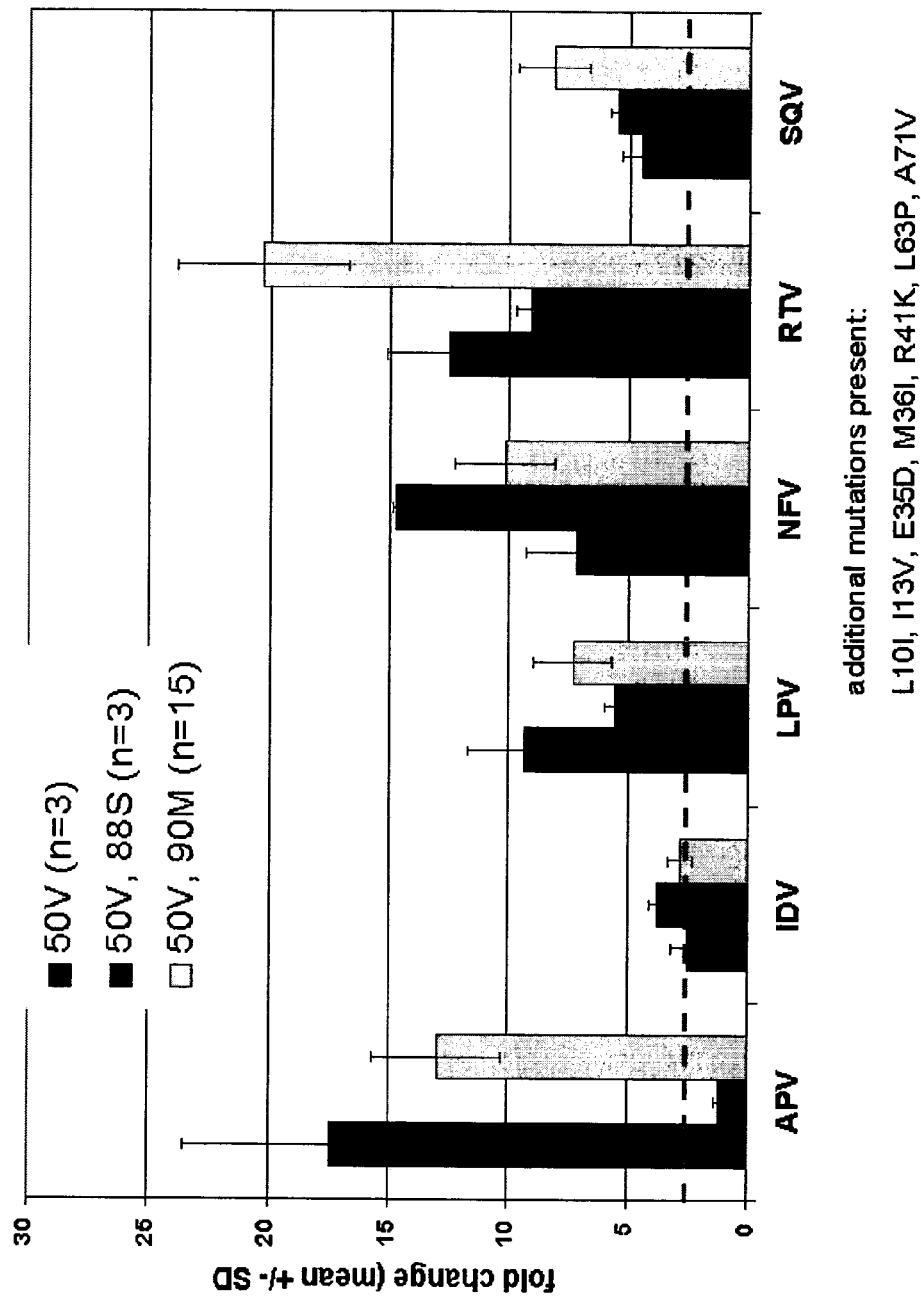

FIG. 7 shows the re-sensitization to amprenavir resistance of an I50V containing virus by N88S. Phenotypic susceptibility of clones containing I50V; I50V and N88S; or I50V and L90M to protease inhibitors with the mean fold-change (error bars represent one standard deviation) for each group of clones is shown. Drug names are abbreviated as follows: APV, amprenavir; IDV, indinavir; LPV, lopinavir; NFV, nelfinavir; RTV, ritonavir; SQV, saquinavir; ATV, atazanavir (BMS 232632).

5. DETAILED DESCRIPTION OF THE INVENTION

The present invention provides methods and compositions for developing an algorithm for determining the effectiveness of anti-viral drugs based on a comprehensive analysis of paired phenotypic and genotypic data guided by phenotypic clinical cut-offs. The present invention also provides methods for determining the susceptibility of a virus to an anti-viral treatment, methods for determining the effectiveness of an anti-viral treatment of an individual infected with a virus, and methods of monitoring the clinical progression of viral infection in individuals receiving anti-viral treatment. In another aspect, the present invention also provides nucleic acids and polypeptides comprising a mutation in the protease of a human immunodeficiency virus ("HIV") associated with reduced susceptibility to protease inhibitors, e.g., amprenavir.

5.1 ABBREVIATIONS

"APV" is an abbreviation for the protease inhibitor amprenavir.

"PI" is an abbreviation for protease inhibitor.

"PT-R" and "PT-S" are abbreviations for "phenotypically resistant" and "phenotypically sensitive," respectively.

"GT-R" and "GT-S" are abbreviations for "genotypically resistant" and "genotypically sensitive," respectively.

"PCR" is an abbreviation for "polymerase chain reaction."

"FC" is an abbreviation for "fold change."

The amino acid notations used herein for the twenty genetically encoded L-amino acids are conventional and are as follows:

| Amino Acid | One-Letter Abbreviation | Three Letter Abbreviation |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

Unless noted otherwise, when polypeptide sequences are presented as a series of one-letter and/or three-letter abbreviations, the sequences are presented in the N->C direction, in accordance with common practice.

Individual amino acids in a sequence are represented herein as AN, wherein A is the standard one letter symbol for the amino acid in the sequence, and N is the position in the sequence. Mutations are represented herein as $A_1NA_2$, wherein $A_1$ is the standard one letter symbol for the amino acid in the reference protein sequence, $A_2$ is the standard one letter symbol for the amino acid in the mutated protein sequence, and N is the position in the amino acid sequence. For example, a G25M mutation represents a change from glycine to methionine at amino acid position 25. Mutations may also be represented herein as $NA_2$, wherein N is the position in the amino acid sequence and $A_2$ is the standard one letter symbol for the amino acid in the mutated protein sequence (e.g., 25M, for a change from the wild-type amino acid to methionine at amino acid position 25). Additionally, mutations may also be represented herein as $A_1N$, wherein $A_1$ is the standard one letter symbol for the amino acid in the reference protein sequence and N is the position in the amino acid sequence (e.g., G25 represents a change from glycine to any amino acid at amino acid position 25). This notation is typically used when the amino acid in the mutated protein sequence is either not known or, if the amino acid in the mutated protein sequence could be any amino acid, except that found in the reference protein sequence. The amino acid positions are numbered based on the full-length sequence of the protein from which the region encompassing the mutation is derived. Representations of nucleotides and point mutations in DNA sequences are analogous.

The abbreviations used throughout the specification to refer to nucleic acids comprising specific nucleobase sequences are the conventional one-letter abbreviations. Thus, when included in a nucleic acid, the naturally occurring encoding nucleobases are abbreviated as follows: adenine (A), guanine (G), cytosine (C), thymine (T) and uracil (U). Unless specified otherwise, single-stranded nucleic acid sequences that are represented as a series of one-letter abbreviations, and the top strand of double-stranded sequences, are presented in the 5'->3' direction.

5.2 DEFINITIONS

As used herein, the following terms shall have the following meanings:

Unless otherwise specified, "primary mutation" refers to a mutation that affects the enzyme active site, i.e. at those amino acid positions that are involved in the enzyme-substrate complex, or that reproducibly appears in an early round of replication when a virus is subject to the selective pressure of an anti-viral agent, or, that has a large effect on phenotypic susceptibility to an anti-viral agent.

"Secondary Mutation" refers to a mutation that is not a primary mutation and that contributes to reduced susceptibility or compensates for gross defects imposed by a primary mutation.

A "phenotypic assay" is a test that measures the sensitivity of a virus (such as HIV) to a specific anti-viral agent.

A "genotypic assay" is a test that determines a genetic sequence of an organism, a part of an organism, a gene or a part of a gene. Such assays are frequently performed in HIV to establish whether certain mutations are associated with drug resistance are present.

As used herein, "genotypic data" are data about the genotype of, for example, a virus. Examples of genotypic data include, but are not limited to, the nucleotide or amino acid sequence of a virus, a part of a virus, a viral gene, a part of a viral gene, or the identity of one or more nucleotides or amino acid residues in a viral nucleic acid or protein.

"Susceptibility" refers to a virus' response to a particular drug. A virus that has decreased or reduced susceptibility to a drug has an increased resistance or decreased sensitivity to the drug. A virus that has increased or enhanced or greater susceptibility to a drug has an increased sensitivity or decreased resistance to the drug.

Phenotypic susceptibility of a virus to a given drug is a continuum. Nonetheless, it is practically useful to define a threshold or thresholds to simplify interpretation of a particular fold-change result. For drugs where sufficient clinical outcome data have been gathered, it is possible to define a "clinical cutoff value," as below.

"Clinical Cutoff Value" refers to a specific point at which resistance begins and sensitivity ends. It is defined by the drug susceptibility level at which a patient's probability of treatment failure with a particular drug significantly increases. The cutoff value is different for different anti-viral agents, as determined in clinical studies. Clinical cutoff values are determined in clinical trials by evaluating resistance and outcomes data. Drug susceptibility (phenotypic) is measured at treatment initiation. Treatment response, such as change in viral load, is monitored at predetermined time points through the course of the treatment. The drug susceptibility is correlated with treatment response and the clinical cutoff value is determined by resistance levels associated with treatment failure (statistical analysis of overall trial results).

"$IC_n$" refers to Inhibitory Concentration. It is the concentration of drug in the patient's blood or in vitro needed to suppress the reproduction of a disease-causing microorganism (such as HIV) by n %. Thus, "$IC_{50}$" refers to the concentration of an anti-viral agent at which virus replication is inhibited by 50% of the level observed in the absence of the drug. "Patient $IC_{50}$" refers to the drug concentration required to inhibit replication of the virus from a patient by 50% and "reference $IC_{50}$" refers to the drug concentration required to inhibit replication of a reference or wild-type virus by 50%. Similarly, "$IC_{90}$" refers to the concentration of an anti-viral agent at which 90% of virus replication is inhibited.

A "fold change" is a numeric comparison of the drug susceptibility of a patient virus and a drug-sensitive reference virus. It is the ratio of the Patient $IC_{50}$ to the drug-sensitive reference $IC_{50}$, i.e., Patient $IC_{50}$/Reference $IC_{50}$=Fold Change ("FC"). A fold change of 1.0 indicates that the patient virus exhibits the same degree of drug susceptibility as the drug-sensitive reference virus. A fold change less than 1 indicates the patient virus is more sensitive than the drug-sensitive reference virus. A fold change greater than 1 indicates the patient virus is less susceptible than the drug-sensitive reference virus. A fold change equal to or greater than the clinical cutoff value means the patient virus has a lower probability of response to that drug. A fold change less than the clinical cutoff value means the patient virus is sensitive to that drug.

"Amprenavir Fold Change" refers to the ratio of the $IC_{50}$ of amprenavir against the HIV from the patient plasma sample to the $IC_{50}$ for amprenavir against the NL4-3 (GenBank Accession No. AF324493) reference viral strain.

A virus is "sensitive" to APV if it has an APV fold change less than 2.5.

A virus is "resistant" to APV if it has an APV fold change of 2.5 or more.

A virus has an "increased likelihood of having reduced susceptibility" to an anti-viral treatment if the virus has a property, for example, a mutation, that is correlated with a reduced susceptibility to the anti-viral treatment. A property of a virus is correlated with a reduced susceptibility if a population of viruses having the property is, on average, less susceptible to the anti-viral treatment than an otherwise similar population of viruses lacking the property. Thus, the correlation between the presence of the property and reduced susceptibility need not be absolute, nor is there a requirement that the property is necessary (i.e., that the property plays a causal role in reducing susceptibility) or sufficient (i.e., that the presence of the property alone is sufficient) for conferring reduced susceptibility.

The term "% sequence homology" is used interchangeably herein with the terms "% homology," "% sequence identity" and "% identity" and refers to the level of amino acid sequence identity between two or more peptide sequences, when aligned using a sequence alignment program. For example, as used herein, 80% homology means the same thing as 80% sequence identity determined by a defined algorithm, and accordingly a homologue of a given sequence has greater than 80% sequence identity over a length of the given sequence. Exemplary levels of sequence identity include, but are not limited to, 60, 70, 80, 85, 90, 95, 98% or more sequence identity to a given sequence.

Exemplary computer programs which can be used to determine identity between two sequences include, but are not limited to, the suite of BLAST programs, e.g., BLASTN, BLASTX, and TBLASTX, BLASTP and TBLASTN, See also Altschul et al., 1990, *J. Mol. Biol.* 215:403-10 (with special reference to the published default setting, i.e., parameters w=4, t=17) and Altschul et al., 1997, *Nucleic Acids Res.*, 25:3389-3402. Sequence searches are typically carried out using the BLASTP program when evaluating a given amino acid sequence relative to amino acid sequences in the GenBank Protein Sequences and other public databases. The BLASTX program is preferred for searching nucleic acid sequences that have been translated in all reading frames against amino acid sequences in the GenBank Protein Sequences and other public databases. Both BLASTP and BLASTX are run using default parameters of an open gap penalty of 11.0, and an extended gap penalty of 1.0, and utilize the BLOSUM-62 matrix. See Altschul, et al., 1997.

A preferred alignment of selected sequences in order to determine "% identity" between two or more sequences, is performed using for example, the CLUSTAL-W program in MacVector version 6.5, operated with default parameters, including an open gap penalty of 10.0, an extended gap penalty of 0.1, and a BLOSUM 30 similarity matrix.

"Polar Amino Acid" refers to a hydrophilic amino acid having a side chain that is uncharged at physiological pH, but which has at least one bond in which the pair of electrons shared in common by two atoms is held more closely by one of the atoms. Genetically encoded polar amino acids include Asn (N), Gln (Q) Ser (S) and Thr (T).

"Nonpolar Amino Acid" refers to a hydrophobic amino acid having a side chain that is uncharged at physiological pH and which has bonds in which the pair of electrons shared in common by two atoms is generally held equally by each of the two atoms (i.e., the side chain is not polar). Genetically encoded apolar amino acids include Ala (A), Gly (G), Ile (I), Leu (L), Met (M) and Val (V).

"Hydrophilic Amino Acid" refers to an amino acid exhibiting a hydrophobicity of less than zero according to the normalized consensus hydrophobicity scale of Eisenberg et al., 1984, J. Mol. Biol. 179:125-142. Genetically encoded hydrophilic amino acids include Arg (R), Asn (N), Asp (D), Glu (E), Gln (Q), H is (H), Lys (K), Ser (S) and Thr (T).

"Hydrophobic Amino Acid" refers to an amino acid exhibiting a hydrophobicity of greater than zero according to the normalized consensus hydrophobicity scale of Eisenberg et al., 1984, J. Mol. Biol. 179:125-142. Genetically encoded hydrophobic amino acids include Ala (A), Gly (G), Ile (I), Leu (L), Met (M), Phe (F), Pro (P), Trp (W), Tyr (Y) and Val (V).

"Acidic Amino Acid" refers to a hydrophilic amino acid having a side chain pK value of less than 7. Acidic amino acids typically have negatively charged side chains at physiological pH due to loss of a hydrogen ion. Genetically encoded acidic amino acids include Asp (D) and Glu (E).

"Basic Amino Acid" refers to a hydrophilic amino acid having a side chain pK value of greater than 7. Basic amino acids typically have positively charged side chains at physiological pH due to association with hydronium ion. Genetically encoded basic amino acids include Arg (R), H is (H) and Lys (K).

A "mutation" is a change in an amino acid sequence or in a corresponding nucleic acid sequence relative to a reference nucleic acid or polypeptide. For embodiments of the invention comprising HIV protease or reverse transcriptase, the reference nucleic acid encoding protease or reverse transcriptase is the protease or reverse transcriptase coding sequence, respectively, present in NL4-3 HIV (GenBank Accession No. AF324493). Likewise, the reference protease or reverse transcriptase polypeptide is that encoded by the NL4-3 HIV sequence. Although the amino acid sequence of a peptide can be determined directly by, for example, Edman degradation or mass spectroscopy, more typically, the amino sequence of a peptide is inferred from the nucleotide sequence of a nucleic acid that encodes the peptide. Any method for determining the sequence of a nucleic acid known in the art can be used, for example, Maxam-Gilbert sequencing (Maxam et al., 1980, *Methods in Enzymology* 65:499), dideoxy sequencing (Sanger et al., 1977, *Proc. Natl. Acad. Sci. USA* 74:5463) or hybridization-based approaches (see e.g., Sambrook et al., 2001, *Molecular Cloning: A Laboratory Manual*, Cold Spring Harbor Laboratory, 3rd ed., NY; and Ausubel et al., 1989, *Current Protocols in Molecular Biology*, Greene Publishing Associates and Wiley Interscience, NY).

A "resistance-associated mutation" ("RAM") in a virus is a mutation correlated with reduced susceptibility of the virus to anti-viral agents. A RAM can be found in several viruses, including, but not limited to a human immunodeficiency virus ("HIV"). Such mutations can be found in one or more of the viral proteins, for example, in the protease, integrase, envelope or reverse transcriptase of HIV. A RAM is defined relative to a reference strain. For embodiments of the invention comprising HIV protease, the reference protease is the protease encoded by NL4-3 HIV (GenBank Accession No. AF324493).

A "mutant" is a virus, gene or protein having a sequence that has one or more changes relative to a reference virus, gene or protein.

The terms "peptide," "polypeptide" and "protein" are used interchangeably throughout.

The terms "reference" and "wild-type" are used interchangeably throughout.

The terms "polynucleotide," "oligonucleotide" and "nucleic acid" are used interchangeably throughout.

5.3 RESISTANCE-ASSOCIATED MUTATIONS

The present invention provides nucleic acids and polypeptides comprising a mutation in the protease of HIV. Preferably, the HIV is human immunodeficiency virus type 1 ("HIV-1"). In one embodiment, the mutation is associated with reduced susceptibility to a protease inhibitor. In another embodiment, the mutation is associated with increased susceptibility to a protease inhibitor. The protease inhibitor can be any protease inhibitor known to one of skill in the art. Examples of protease inhibitors include, but are not limited to, saquinavir, ritonavir, indinavir, nelfinavir, amprenavir and lopinavir. In one embodiment, the protease inhibitor is amprenavir.

In one aspect, the present invention provides peptides, polypeptides or proteins comprising a mutation in the protease of HIV associated with either reduced or increased susceptibility to a protease inhibitor, e.g., amprenavir. In one embodiment, the invention provides a polypeptide derived from the HIV protease and comprising a mutation associated with reduced susceptibility to a protease inhibitor. In another embodiment, the polypeptide comprises more than one mutation associated with reduced susceptibility to a protease inhibitor. In another embodiment, the polypeptide comprises a mutation associated with increased susceptibility to a protease inhibitor. In another embodiment, the polypeptide comprises more than one mutation associated with increased susceptibility to a protease inhibitor. Polypeptides of the invention include peptides, polypeptides and proteins that are modified or derived from these polypeptides. In one embodiment, the polypeptide comprises post-translational modifications. In another embodiment, the polypeptide comprises one or more amino acid analogs.

In a preferred embodiment, the polypeptide comprises one or more mutations associated with reduced susceptibility to amprenavir. Table 1 provides a list of mutations associated with reduced susceptibility to amprenavir.

In another preferred embodiment, the invention provides a polypeptide derived from the HIV protease and comprising at least one mutation selected from a group of mutations consisting of: V11I, V11L, L33F, E34Q, K43T, G48M, I54A, I54S, I54T, Q58E, A71L, L76V, P79, V82A, V82F, N83D, I84A, I84C, T91A, T91S, T91V and C95F, wherein the mutation is associated with reduced susceptibility to amprenavir.

In another preferred embodiment, the polypeptide comprising said mutation comprises at least 10, 15, 20, 25, 30, 35, 40, 45, 50, 60, 70, 80, 85, 90 or 95 contiguous amino acids of SEQ ID NO: 1, within which sequence said mutation or mutations can be present.

In another embodiment, the polypeptide comprising said mutation or mutations is at least 70%, but less than 100%, identical to a polypeptide having the amino acid sequence of SEQ ID NO:1; the polypeptide has an amino acid sequence that is greater than 80% identical to the amino acid sequence of SEQ ID NO:1; or the polypeptide has an amino acid sequence that is greater than 90% identical to the amino acid sequence of SEQ ID NO:1; wherein the mutation is associated with reduced susceptibility to a protease inhibitor.

In one embodiment, said polypeptide is naturally-occurring. In another embodiment, said polypeptide is artificially designed.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (% identity=# of identical positions/total # of positions (e.g., overlapping positions)×100). In one embodiment, the two sequences are the same length.

The determination of percent identity between two sequences can be accomplished using a mathematical algorithm. A preferred, non-limiting example of a mathematical algorithm utilized for the comparison of two sequences is the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877. Such an algorithm is incorporated into the NBLAST and XBLAST programs of Altschul, et al. (1990) *J. Mol. Biol.* 215:403-410. BLAST nucleotide searches can be performed with the NBLAST program, score=100, wordlength=12 to obtain nucleotide sequences homologous to a nucleic acid molecules of the invention. BLAST protein searches can be performed with the XBLAST program, score=50, wordlength=3 to obtain amino acid sequences homologous to a protein molecules of the invention. To obtain gapped alignments for comparison purposes, Gapped BLAST can be utilized as described in Altschul et al. (1997) *Nucleic Acids Res.* 25:3389-3402. Alternatively, PSI-Blast can be used to perform an iterated search that detects distant relationships between molecules. Id. When utilizing BLAST, Gapped BLAST, and PSI-Blast programs, the default parameters of the respective programs (e.g., XBLAST and NBLAST) can be used.

Another preferred, non-limiting example of a mathematical algorithm utilized for the comparison of sequences is the algorithm of Myers and Miller, CABIOS (1989). Such an algorithm is incorporated into the ALIGN program (version 2.0) that is part of the CGC sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis and Robotti (1994) *Comput. Appl. Biosci.*, 10:3-5; and FASTA described in Pearson and Lipman (1988) *Proc. Natl. Acad. Sci.* 85:2444-8. Within FASTA, ktup is a control option that sets the sensitivity and speed of the search. If ktup=2, similar regions in the two sequences being compared are found by looking at pairs of aligned residues; if ktup=1, single aligned amino acids are examined. ktup can be set to 2 or 1 for protein sequences, or from 1 to 6 for DNA sequences. The default if ktup is not specified is 2 for proteins and 6 for DNA.

The percent identity between two sequences can be determined using techniques similar to those described above, with or without allowing gaps. In calculating percent identity, typically exact matches are counted.

In another aspect, the present invention provides polynucleotides, oligonucleotides or nucleic acids encoding or relating to a polypeptide of the invention or a biologically active portion thereof, including, for example, nucleic acid molecules sufficient for use as hybridization probes, PCR primers or sequencing primers for identifying, analyzing, mutating or amplifying the nucleic acids of the invention.

In one embodiment, the nucleic acid encodes a polypeptide comprising a mutation in the protease of HIV associated with either reduced or increased susceptibility to a protease inhibitor, e.g., amprenavir. In one embodiment, the invention provides a nucleic acid encoding a polypeptide derived from the HIV protease and comprising one or more mutations associated with reduced susceptibility to a protease inhibitor. In another embodiment, the nucleic acid encodes a polypeptide that comprises one or more mutations associated with increased susceptibility to a protease inhibitor. Nucleic acids of the invention include nucleic acids, polynucleotides and oligonucleotides that are modified or derived from these nucleic acid sequences. In one embodiment, the nucleic acid comprises nucleic acid analogs. In one embodiment, the na is naturally-occurring. In another embodiment, said nucleic acid is artificially designed.

The nucleic acid can be any length. The nucleic acid can be, for example, at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 85, 90, 100, 110, 120, 125, 150, 175, 200, 250, 300, 350, 375, 400, 425, 450, 475 or 500 nucleotides in length. The nucleic acid can be, for example, less than 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 85, 90, 100, 110, 120, 125, 150, 175, 200, 250, 300, 350, 375, 400, 425, 450, 475, 500, 525, 550, 575, 600, 650, 700, 750, 800, 850, 900, 950, 1000, 1100, 1200, 1300, 1400, 1500, 1600, 1700, 1800, 1900, 2000, 2500, 3000, 3500, 4000, 4500, 5000, 5500, 6000, 6500, 7000, 7500, 8000, 8500, 9000, 9500 or 10000 nucleotides in length. In a preferred embodiment, the nucleic acid has a length and a sequence suitable for detecting a mutation described herein, for example, as a probe or a primer.

In one embodiment, the nucleic acid encodes a polypeptide, or a portion of a polypeptide, that comprises one or more mutations associated with reduced susceptibility to amprenavir. Table 1 provides a list of mutations associated with reduced susceptibility to amprenavir.

In another embodiment, the invention provides an oligonucleotide encoding a polypeptide derived from the HIV protease and comprising at least one mutation selected from a group of mutations consisting of: V11I, V11L, L33F, E34Q, K43T, G48M, I54A, I54S, I54T, Q58E, A71L, L76V, P79, V82A, V82F, N83D, I84A, I84C, T91A, T91S, T91V and C95F.

In another embodiment, said oligonucleotide comprising said mutation comprises 15, 30, 45, 60, 75, 90, 105, 120, 135, 150, 180, 210, 240, 255, 270 or 285 contiguous nucleic acids of SEQ ID NO: 2, within which sequence said mutation or mutations can be present.

In another embodiment, the oligonucleotide comprising said mutation or mutations is at least 60%, but less than 100%, identical to an oligonucleotide having the nucleic acid sequence of SEQ ID NO:2; the oligonucleotide has an nucleic acid sequence that is greater than 70% identical to the nucleic acid sequence of SEQ ID NO:2; the oligonucleotide has an nucleic acid sequence that is greater than 80% identical to the nucleic acid sequence of SEQ ID NO:2; or the oligonucleotide has an nucleic acid sequence that is greater than 90% identical to the nucleic acid sequence of SEQ ID NO:2, wherein the mutation is associated with reduced susceptibility to a protease inhibitor. The percent identity of two nucleic acid sequences can be determined as described above.

In addition to the nucleotide sequence of SEQ ID NO: 2, it will be appreciated by those skilled in the art that DNA sequence polymorphisms that lead to changes in the amino acid sequence may exist within a population (e.g., the human population). Such genetic polymorphisms may exist among individuals within a population due to natural allelic variation. Natural allelic variations can typically result in 1-5% variance in the nucleotide sequence of a given gene. Any and all such nucleotide variations and resulting amino acid variations or polymorphisms that are the result of natural allelic variation and that do not alter the functional activity are intended to be within the scope of the invention.

In another embodiment, the present invention provides nucleic acid molecules that are suitable for use as primers or hybridization probes for the detection of nucleic acid sequences of the invention. A nucleic acid molecule of the invention can comprise only a portion of a nucleic acid sequence encoding a full length polypeptide of the invention for example, a fragment that can be used as a probe or primer or a fragment encoding a biologically active portion of a polypeptide of the invention. The probe can comprise a labeled group attached thereto, e.g., a radioisotope, a fluorescent compound, an enzyme, or an enzyme co-factor. In various embodiments, the nucleic acid molecules of the invention can be modified at the base moiety, sugar moiety or phosphate backbone.

5.4 FINDING DRUG RESISTANCE-ASSOCIATED VIRAL MUTATIONS

In another aspect, the present invention provides methods for finding resistance-associated mutation in a virus or a derivative of the virus.

5.4.1 The Virus and Viral Samples

A resistance-associated mutation ("RAM") according to the present invention can be present in any type of virus, for example, any virus found in animals. In one embodiment of the invention, the virus includes viruses known to infect mammals, including dogs, cats, horses, sheep, cows etc. In a preferred embodiment, the virus is known to infect primates. In an even more preferred embodiment the virus is known to infect humans. Examples of human viruses include, but are not limited to, human immunodeficiency virus ("HIV"), herpes simplex virus, cytomegalovirus virus, varicella zoster virus, other human herpes viruses, influenza A virus, respiratory syncytial virus, hepatitis A, B and C viruses, rhinovirus, and human papilloma virus. In a preferred embodiment of the invention, the virus is HIV. Preferably, the virus is human immunodeficiency virus type 1 ("HIV-1"). The foregoing are representative of certain viruses for which there is presently available anti-viral chemotherapy and represent the viral families retroviridae, herpesviridae, orthomyxoviridae, paramxyxovirus, picornavirus, flavivirus, pneumovirus and hepadnaviridae. This invention can be used with other viral infections due to other viruses within these families as well as viral infections arising from viruses in other viral families for which there is or there is not a currently available therapy.

A RAM according to the present invention can be found in a viral sample obtained by any means known in the art for obtaining viral samples. Such methods include, but are not limited to, obtaining a viral sample from a human or an animal infected with the virus or obtaining a viral sample from a viral culture. In one embodiment, the viral sample is obtained from a human individual infected with the virus. The viral sample could be obtained from any part of the infected individual's body or any secretion expected to contain the virus. Examples of such parts include, but are not limited to blood, serum, plasma, sputum, lymphatic fluid, semen, vaginal mucus and samples of other bodily fluids. In a preferred embodiment, the sample is a blood, serum or plasma sample.

In another embodiment, a RAM according to the present invention is present in a virus that can be obtained from a culture. In some embodiments, the culture can be obtained from a laboratory. In other embodiments, the culture can be obtained from a collection, for example, the American Type Culture Collection.

In certain embodiments, a RAM according to the present invention is present in a derivative of a virus. In one embodiment, the derivative of the virus is not itself pathogenic. In another embodiment, the derivative of the virus is a plasmid-based system, wherein replication of the plasmid or of a cell transfected with the plasmid is affected by the presence or absence of the selective pressure, such that mutations are selected that increase resistance to the selective pressure. In some embodiments, the derivative of the virus comprises the nucleic acids or proteins of interest, for example, those nucleic acids or proteins to be targeted by an anti-viral treatment. In one embodiment, the genes of interest can be incorporated into a vector. See, e.g., U.S. Pat. Nos. 5,837,464 and 6,242,187 and PCT publication, WO 99/67427, each of which is incorporated herein by reference. In a preferred embodiment, the genes can be those that encode for a protease or reverse transcriptase.

In another embodiment, the intact virus need not be used. Instead, a part of the virus incorporated into a vector can be used. Preferably that part of the virus is used that is targeted by an anti-viral drug.

In another embodiment, a RAM according to the present invention is present in a genetically modified virus. The virus can be genetically modified using any method known in the art for genetically modifying a virus. For example, the virus can be grown for a desired number of generations in a laboratory culture. In one embodiment, no selective pressure is applied (i.e., the virus is not subjected to a treatment that favors the replication of viruses with certain characteristics), and new mutations accumulate through random genetic drift. In another embodiment, a selective pressure is applied to the virus as it is grown in culture (i.e., the virus is grown under conditions that favor the replication of viruses having one or more characteristics). In one embodiment, the selective pressure is an anti-viral treatment. Any known anti-viral treatment can be used as the selective pressure. In one embodiment, the virus is HIV and the selective pressure is a protease inhibitor. In another embodiment, the virus is HIV-1 and the selective pressure is a protease inhibitor. Any protease inhibitor can be used to apply the selective pressure. Examples of protease inhibitors include, but are not limited to, saquinavir, ritonavir, indinavir, nelfinavir, amprenavir and lopinavir. In one embodiment, the protease inhibitor is selected from a group consisting of saquinavir, ritonavir, indinavir, nelfinavir, amprenavir and lopinavir. In another embodiment, the protease inhibitor is amprenavir. By treating HIV cultured in vitro with a protease inhibitor, e.g., amprenavir, one can select for mutant strains of HIV that have an increased resistance to amprenavir. The stringency of the selective pressure can be manipulated to increase or decrease the survival of viruses not having the selected-for characteristic.

In another aspect, a RAM according to the present invention is made by mutagenizing a virus, a viral genome, or a part of a viral genome. Any method of mutagenesis known in the art can be used for this purpose. In one embodiment, the mutagenesis is essentially random. In another embodiment, the essentially random mutagenesis is performed by exposing the virus, viral genome or part of the viral genome to a mutagenic treatment. In another embodiment, a gene that encodes a viral protein that is the target of an anti-viral therapy is mutagenized. Examples of essentially random mutagenic treatments include, for example, exposure to mutagenic substances (e.g., ethidium bromide, ethylmethanesulphonate, ethyl nitroso urea (ENU) etc.) radiation (e.g., ultraviolet light), the insertion and/or removal of transposable elements (e.g., Tn5, Tn10), or replication in a cell, cell extract, or in vitro replication system that has an increased rate of mutagenesis. See, e.g., Russell et al., 1979, *Proc. Nat. Acad. Sci. USA* 76:5918-5922; Russell, W., 1982, Environmental Mutagens and Carcinogens: Proceedings of the Third International Conference on Environmental Mutagens. One of skill in the art will appreciate that while each of these methods of mutagenesis is essentially random, at a molecular level, each has its own preferred targets.

In another aspect, a mutation that might affect the sensitivity of a virus to an anti-viral therapy is made using site-directed mutagenesis. Any method of site-directed mutagenesis known in the art can be used (see e.g., Sambrook et al., 2001, *Molecular Cloning: A Laboratory Manual*, Cold Spring Harbor Laboratory, 3rd ed., NY; and Ausubel et al., 1989, *Current Protocols in Molecular Biology*, Greene Publishing Associates and Wiley Interscience, NY). The site directed mutagenesis can be directed to, e.g., a particular gene or genomic region, a particular part of a gene or genomic region, or one or a few particular nucleotides within a gene or genomic region. In one embodiment, the site directed mutagenesis is directed to a viral genomic region, gene, gene fragment, or nucleotide based on one or more criteria. In one embodiment, a gene or a portion of a gene is subjected to site-directed mutagenesis because it encodes a protein that is known or suspected to be a target of an anti-viral therapy, e.g., the gene encoding the HIV protease. In another embodiment, a portion of a gene, or one or a few nucleotides within a gene, are selected for site-directed mutagenesis. In one embodiment, the nucleotides to be mutagenized encode amino acid residues that are known or suspected to interact with an anti-viral compound. In another embodiment, the nucleotides to be mutagenized encode amino acid residues that are known or suspected to be mutated in viral strains having decreased susceptibility to the anti-viral treatment. In another embodiment, the mutagenized nucleotides encode amino acid residues that are adjacent to or near in the primary sequence of the protein residues known or suspected to interact with an anti-viral compound or known or suspected to be mutated in viral strains having decreased susceptibility to an anti-viral treatment. In another embodiment, the mutagenized nucleotides encode amino acid residues that are adjacent to or near to in the secondary, tertiary or quaternary structure of the protein residues known or suspected to interact with an anti-viral compound or known or suspected to be mutated in viral strains having decreased susceptibility to an anti-viral treatment. In another embodiment, the mutagenized nucleotides encode amino acid residues in or near the active site of a protein that is known or suspected to bind to an anti-viral compound. See, e.g., Sarkar and Sommer, 1990, *Biotechniques,* 8:404-407.

5.4.2 Detecting the Presence or Absence of Mutations in a Virus

The presence or absence of a RAM according to the present invention in a virus can be detected by any means known in the art for detecting a mutation. The mutation can be detected in the viral gene that encodes a particular protein, or in the protein itself, i.e., in the amino acid sequence of the protein.

In one embodiment, the mutation is in the viral genome. Such a mutation can be in, for example, a gene encoding a viral protein, in a cis or trans acting regulatory sequence of a gene encoding a viral protein, an intergenic sequence, or an intron sequence. The mutation can affect any aspect of the structure, function, replication or environment of the virus that changes its susceptibility to an anti-viral treatment. In one embodiment, the mutation is in a gene encoding a viral protein that is the target of an anti-viral treatment.

A mutation within a viral gene can be detected by utilizing a number of techniques. Viral DNA or RNA can be used as the starting point for such assay techniques, and may be isolated according to standard procedures which are well known to those of skill in the art.

The detection of a mutation in specific nucleic acid sequences, such as in a particular region of a viral gene, can be accomplished by a variety of methods including, but not limited to, restriction-fragment-length-polymorphism detection based on allele-specific restriction-endonuclease cleavage (Kan and Dozy, 1978, *Lancet* ii:910-912), mismatch-repair detection (Faham and Cox, 1995, *Genome Res* 5:474-482), binding of MutS protein (Wagner et al., 1995, *Nucl Acids Res* 23:3944-3948), denaturing-gradient gel electrophoresis (Fisher et al., 1983, *Proc. Natl. Acad. Sci. U.S.A.* 80:1579-83), single-strand-conformation-polymorphism detection (Orita et al., 1983, *Genomics* 5:874-879), RNAase cleavage at mismatched base-pairs (Myers et al., 1985, *Science* 230:1242), chemical (Cotton et al., 1988, *Proc. Natl. Acad. Sci. U.S.A.* 85:4397-4401) or enzymatic (Youil et al., 1995, *Proc. Natl. Acad. Sci. U.S.A.* 92:87-91) cleavage of heteroduplex DNA, methods based on oligonucleotide-specific primer extension (Syvänen et al., 1990, *Genomics* 8:684-692), genetic bit analysis (Nikiforov et al., 1994, *Nucl Acids Res* 22:4167-4175), oligonucleotide-ligation assay (Landegren et al., 1988, *Science* 241:1077), oligonucleotide-specific ligation chain reaction ("LCR") (Barrany, 1991, *Proc. Natl. Acad. Sci. U.S.A.* 88:189-193), gap-LCR (Abravaya et al., 1995, *Nucl Acids Res* 23:675-682), radioactive or fluorescent DNA sequencing using standard procedures well known in the art, and peptide nucleic acid (PNA) assays (Orum et al., 1993, *Nucl. Acids Res.* 21:5332-5356; Thiede et al., 1996, *Nucl. Acids Res.* 24:983-984).

In addition, viral DNA or RNA may be used in hybridization or amplification assays to detect abnormalities involving gene structure, including point mutations, insertions, deletions and genomic rearrangements. Such assays may include, but are not limited to, Southern analyses (Southern, 1975, *J. Mol. Biol.* 98:503-517), single stranded conformational polymorphism analyses (SSCP) (Orita et al., 1989, *Proc. Natl. Acad. Sci. USA* 86:2766-2770), and PCR analyses (U.S. Pat. Nos. 4,683,202; 4,683,195; 4,800,159; and 4,965,188; PCR Strategies, 1995 Innis et al. (eds.), Academic Press, Inc.).

Such diagnostic methods for the detection of a gene-specific mutation can involve for example, contacting and incubating the viral nucleic acids with one or more labeled nucleic acid reagents including recombinant DNA molecules, cloned genes or degenerate variants thereof, under conditions favorable for the specific annealing of these reagents to their complementary sequences. Preferably, the lengths of these nucleic acid reagents are at least 15 to 30 nucleotides. After incubation, all non-annealed nucleic acids are removed from the nucleic acid molecule hybrid. The presence of nucleic acids which have hybridized, if any such molecules exist, is then detected. Using such a detection scheme, the nucleic acid from the virus can be immobilized, for example, to a solid support such as a membrane, or a plastic surface such as that on a microtiter plate or polystyrene beads. In this case, after incubation, non-annealed, labeled nucleic acid reagents of the type described above are easily removed. Detection of the remaining, annealed, labeled nucleic acid reagents is accomplished using standard techniques well-known to those in the art. The gene sequences to which the nucleic acid reagents have annealed can be compared to the annealing pattern expected from a normal gene sequence in order to determine whether a gene mutation is present.

Alternative diagnostic methods for the detection of gene specific nucleic acid molecules may involve their amplification, e.g., by PCR (U.S. Pat. Nos. 4,683,202; 4,683,195; 4,800,159; and 4,965,188; PCR Strategies, 1995 Innis et al. (eds.), Academic Press, Inc.), followed by the detection of the amplified molecules using techniques well known to those of skill in the art. The resulting amplified sequences can be compared to those which would be expected if the nucleic acid being amplified contained only normal copies of the respective gene in order to determine whether a gene mutation exists.

Additionally, the nucleic acid can be sequenced by any sequencing method known in the art. For example, the viral DNA can be sequenced by the dideoxy method of Sanger et al., 1977, *Proc. Natl. Acad. Sci. USA* 74:5463, as further described by Messing et al., 1981, *Nuc. Acids Res.* 9:309, or by the method of Maxam et al., 1980, *Methods* in Enzymology 65:499. See also the techniques described in Sambrook et al., 2001, *Molecular Cloning: A Laboratory Manual*, Cold Spring Harbor Laboratory, 3rd ed., NY; and Ausubel et al., 1989, *Current Protocols in Molecular Biology*, Greene Publishing Associates and Wiley Interscience, NY.

Antibodies directed against the viral gene products, i.e., viral proteins or viral peptide fragments can also be used to detect mutations in the viral proteins. Alternatively, the viral protein or peptide fragments of interest can be sequenced by any sequencing method known in the art in order to yield the amino acid sequence of the protein of interest. An example of such a method is the Edman degradation method which can be used to sequence small proteins or polypeptides. Larger proteins can be initially cleaved by chemical or enzymatic reagents known in the art, for example, cyanogen bromide, hydroxylamine, trypsin or chymotrypsin, and then sequenced by the Edman degradation method.

5.5 MEASURING PHENOTYPIC SUSCEPTIBILITY OF A MUTANT VIRUS

Any method known in the art can be used to determine the phenotypic susceptibility of a mutant virus or population of viruses to an anti-viral therapy. See e.g., U.S. Pat. Nos. 5,837,464 and 6,242,187, incorporated herein by reference in their entireties. In some embodiments a phenotypic analysis is performed, i.e., the susceptibility of the virus to a given antiviral agent is assayed with respect to the susceptibility of a reference virus without the mutations. This is a direct, quantitative measure of drug susceptibility and can be performed by any method known in the art to determine the susceptibility of a virus to an anti-viral agent. An example of such methods includes, but is not limited to, determining the fold change in $IC_{50}$ values with respect to a reference virus. Phenotypic testing measures the ability of a specific viral strain to grow in vitro in the presence of a drug inhibitor. A virus is less susceptible to a particular drug when more of the drug is required to inhibit viral activity, versus the amount of drug required to inhibit the reference virus.

In one embodiment, a phenotypic analysis is performed and used to calculate the $IC_{50}$ or $IC_{90}$ of a drug for a viral strain. The results of the analysis can also be presented as fold-change in $IC_{50}$ or $IC_{90}$ for each viral strain as compared with a drug-susceptible control strain or a prior viral strain from the same patient. Because the virus is directly exposed to each of the available anti-viral medications, results can be directly linked to treatment response. For example, if the patient virus shows resistance to a particular drug, that drug is avoided or omitted from the patient's treatment regimen, allowing the physician to design a treatment plan that is more likely to be effective for a longer period of time.

In another embodiment, the phenotypic analysis is performed using recombinant virus assays ("RVAs"). RVAs use virus stocks generated by homologous recombination between viral vectors and viral gene sequences, amplified from the patient virus. In some embodiments, the viral vector is a HIV vector and the viral gene sequences are protease and/or reverse transcriptase sequences.

In a preferred embodiment, the phenotypic analysis is performed using PHENOSENSE™ (ViroLogic Inc., South San Francisco, Calif.). See Petropoulos et al., 2000, *Antimicrob. Agents Chemother.* 44:920-928; U.S. Pat. Nos. 5,837,464 and 6,242,187. PHENOSENSE™ is a phenotypic assay that achieves the benefits of phenotypic testing and overcomes the drawbacks of previous assays. Because the assay has been automated, PHENOSENSE™ offers higher throughput under controlled conditions. The result is an assay that accurately defines the susceptibility profile of a patient's HIV isolates to all currently available antiretroviral drugs, and delivers results directly to the physician within about 10 to about 15 days of sample receipt. PHENOSENSE™ is accurate and can obtain results with only one round of viral replication, thereby avoiding selection of subpopulations of virus. The results are quantitative, measuring varying degrees of drug susceptibility, and sensitive—the test can be performed on blood specimens with a viral load of about 500 copies/mL and can detect minority populations of some drug-resistant virus at concentrations of 10% or less of total viral population. Furthermore, the results are reproducible and can vary by less than about 1.4-2.5 fold, depending on the drug, in about 95% of the assays performed.

PHENOSENSE™ can be used with nucleic acids from amplified viral gene sequences. As discussed in Section 5.4.1, the sample containing the virus may be a sample from a human or an animal infected with the virus or a sample from a culture of viral cells. In one embodiment, the viral sample comprises a genetically modified laboratory strain.

A resistance test vector ("RTV") can then be constructed by incorporating the amplified viral gene sequences into a replication defective viral vector by using any method known in the art of incorporating gene sequences into a vector. In one embodiment, restrictions enzymes and conventional cloning methods are used. See Sambrook et al., 2001, *Molecular Cloning: A Laboratory Manual*, Cold Spring Harbor Laboratory, 3$^{rd}$ ed., NY; and Ausubel et al., 1989, *Current Protocols in Molecular Biology*, Greene Publishing Associates and Wiley Interscience, NY. In a preferred embodiment, ApaI and PinAI restriction enzymes are used. Preferably, the replication defective viral vector is the indicator gene viral vector ("IGVV"). In a preferred embodiment, the viral vector contains a means for detecting replication of the RTV. Preferably, the viral vector contains a luciferase expression cassette.

The assay can be performed by first co-transfecting host cells with RTV DNA and a plasmid that expresses the envelope proteins of another retrovirus, for example, amphotropic murine leukemia virus (MLV). Following transfection, virus particles can be harvested and used to infect fresh target cells. The completion of a single round of viral replication can be detected by the means for detecting replication contained in the vector. In a preferred embodiment, the completion of a single round of viral replication results in the production of luciferase. Serial concentrations of anti-viral agents can be added at either the transfection step or the infection step.

Susceptibility to the anti-viral agent can be measured by comparing the replication of the vector in the presence and absence of the anti-viral agent. For example, susceptibility to the anti-viral agent can be measured by comparing the luciferase activity in the presence and absence of the anti-viral agent. Susceptible viruses would produce low levels of luciferase activity in the presence of antiviral agents, whereas viruses with reduced susceptibility would produce higher levels of luciferase activity.

In preferred embodiments, PHENOSENSE™ is used in evaluating the phenotypic susceptibility of HIV-1 to anti-viral drugs. Preferably, the anti-viral drug is a protease inhibitor. More preferably, it is amprenavir. In preferred embodiments, the reference viral strain is HIV strain NL4-3 or HXB-2.

In one embodiment, viral nucleic acid, for example, HIV-1 RNA is extracted from plasma samples, and a fragment of, or entire viral genes could be amplified by methods such as, but not limited to PCR. See, e.g., Hertogs et al., 1998, *Antimicrob Agents Chemother* 42(2):269-76. In one example, a 2.2-kb fragment containing the entire HIV-1 PR- and RT-coding sequence is amplified by nested reverse transcription-PCR. The pool of amplified nucleic acid, for example, the PR-RT-coding sequences, is then cotransfected into a host cell such as CD4+ T lymphocytes (MT4) with the pGEMT3deltaPRT plasmid from which most of the PR (codons 10 to 99) and RT (codons 1 to 482) sequences are deleted. Homologous recombination leads to the generation of chimeric viruses containing viral coding sequences, such as the PR- and RT-coding sequences derived from HIV-1 RNA in plasma. The susceptibilities of the chimeric viruses to all currently available anti-viral agents targeting the products of the transfected genes (proRT and/or PR inhibitors, for example), can be determined by any cell viability assay known in the art. For example, an MT4 cell-3-(4,5-dimethylthiazol-2-yl)-2,5-diphenyltetrazolium bromide-based cell viability assay can be used in an automated system that allows high sample throughput. The profile of resistance to all the anti-viral agents, such as the RT and PR inhibitors can be displayed graphically in a single PR-RT-Antivirogram.

Other assays for evaluating the phenotypic susceptibility of a virus to anti-viral drugs known to one of skill in the art can be used. See, e.g., Shi and Mellors, 1997, *Antimicrob Agents Chemother.* 41(12):2781-85; Gervaix et al., 1997, *Proc Natl Acad Sci U.S.A.* 94(9):4653-8; Race et al., 1999, *AIDS* 13:2061-2068, incorporated herein by reference in their entireties.

In another embodiment, the susceptibility of a virus to treatment with an anti-viral treatment is determined by assaying the activity of the target of the anti-viral treatment in the presence of the anti-viral treatment. In one embodiment, the virus is HIV, the anti-viral treatment is a protease inhibitor, and the target of the anti-viral treatment is the HIV protease. See, e.g., U.S. Pat. Nos. 5,436,131, 6,103,462, incorporated herein by reference in their entireties.

5.6 CORRELATING PHENOTYPIC AND GENOTYPIC SUSCEPTIBILITY

Any method known in the art can be used to determine whether a mutation is correlated with a decrease in susceptibility of a virus to an anti-viral treatment and thus is a RAM according to the present invention. In one embodiment, P values are used to determine the statistical significance of the correlation, such that the smaller the P value, the more significant the measurement. Preferably the P values will be less than 0.05. More preferably, P values will be less than 0.01. P values can be calculated by any means known to one of skill in the art. In one embodiment, P values are calculated using Fisher's Exact Test. See, e.g., David Freedman, Robert Pisani & Roger Purves, 1980, STATISTICS, W. W. Norton, New York.

In a preferred embodiment, numbers of samples with the mutation being analyzed that have an $IC_{50}$ fold change below or above 2.5-fold are compared to numbers of samples without the mutation. A 2×2 table can be constructed and the P value can be calculated using Fisher's Exact Test (see Example 1). P values smaller than 0.05 or 0.01 can be classified as statistically significant.

5.7 DETERMINING SUSCEPTIBILITY TO THE ANTI-VIRAL TREATMENT

In another aspect, the present invention provides a method for determining a virus' susceptibility to anti-viral treatment. Resistance-associated mutations (RAMs) can be identified and correlated with reduced susceptibility of a virus to an anti-viral treatment as described in Sections 5.3-5.6 above. The presence of a RAM in a virus can be detected by any means known in the art, e.g., as discussed in Section 5.4.2 above. The presence of a RAM in the virus can indicate that the virus has an increased likelihood of having reduced susceptibility for the anti-viral treatment. In one embodiment, the virus is human immunodeficiency virus (HIV). In another embodiment, the virus is human immunodeficiency virus type-1 (HIV-1). In another embodiment, the anti-viral treatment is a protease inhibitor. Examples of protease inhibitors include, but are not limited to, saquinavir, ritonavir, indinavir, nelfinavir, amprenavir and lopinavir. In one embodiment, the protease inhibitor is selected from a group consisting of saquinavir, ritonavir, indinavir, nelfinavir, amprenavir and lopinavir.

In another embodiment, the invention provides a method for determining whether a HIV has an increased likelihood of having a reduced susceptibility to treatment with a protease inhibitor, comprising detecting in the protease of said HIV the presence or absence of a mutation associated with reduced susceptibility to treatment with said protease inhibitor at amino acid position 11, 32, 33, 34, 43, 46, 47, 48, 50, 54, 58, 71, 76, 79, 82, 83, 84, 91 or 95 of an amino acid sequence of said protease, wherein the presence of said mutation indicates that the HIV has an increased likelihood of having reduced susceptibility to treatment with the protease inhibitor, with the proviso that said mutation is not V32I, M46I, M46L, I47V, I50V, I54L, I54M or I84V.

In another embodiment, the invention provides a method of determining whether a HIV has an increased likelihood of having a reduced susceptibility to treatment with a protease inhibitor, comprising detecting in the protease of said HIV the presence or absence of a mutation selected from the group consisting of: V11I, V11L, L33F, E34Q, K43T, G48M, I54A, I54S, I54T, Q58E, A71L, L76V, P79, V82A, V82F, N83D, I84A, I84C, T91A, T91S, T91V and C95F, wherein the mutation is associated with reduced susceptibility to treatment with said protease inhibitor and the presence of said mutation indicates that the HIV has an increased likelihood of having reduced susceptibility to treatment with the protease inhibitor compared to a HIV without said mutation, e.g., a wild type or reference HIV.

In another aspect, the present invention provides a method for determining the susceptibility of an individual infected with a virus to anti-viral treatment. Resistance-associated mutations (RAMs) can be identified and correlated with reduced susceptibility of a virus to an anti-viral treatment as described in Sections 5.3-5.6 above. The presence of a RAM in a virus present in a sample from the individual can be detected by any means known in the art, e.g., as discussed in Section 5.4.2 above. The presence of a RAM in the virus can indicate that the individual has an increased likelihood of having reduced susceptibility for the anti-viral treatment. In one embodiment, the virus is HIV. In another embodiment, the virus is HIV-1. In another embodiment, the anti-viral treatment is a protease inhibitor. Examples of protease inhibitors include, but are not limited to, saquinavir, ritonavir, indinavir, nelfinavir, amprenavir and lopinavir. In one embodiment, the protease inhibitor is selected from a group consisting of saquinavir, ritonavir, indinavir, nelfinavir, amprenavir and lopinavir. In another embodiment, the protease inhibitor is amprenavir.

In another embodiment, the invention provides a method of determining whether an individual infected with HIV has an increased likelihood of having a reduced susceptibility to treatment with a protease inhibitor, comprising detecting, in a sample from said individual, the presence or absence of a mutation associated with reduced susceptibility to treatment with said protease inhibitor at amino acid position 11, 32, 33, 34, 43, 46, 47, 48, 50, 54, 58, 71, 76, 79, 82, 83, 84, 91 or 95 of the amino acid sequence of the protease of the HIV, wherein the presence of said mutation indicates that the individual has an increased likelihood of having reduced susceptibility to treatment with the protease inhibitor, with the proviso that said mutation is not V32I, M46I, M46L, I47V, I50V, I54L, I54M or I84V.

In another embodiment, the invention provides a method for determining the effectiveness of protease inhibitor treatment of an individual infected with a HIV, comprising detecting, in a sample from said individual, the presence or absence of a mutation associated with reduced susceptibility to treatment with said protease inhibitor at amino acid position 11, 32, 33, 34, 43, 46, 47, 48, 50, 54, 58, 71, 76, 79, 82, 83, 84, 91 or 95 of the amino acid sequence of the protease of the HIV, wherein the presence of said mutation indicates that the individual has a reduced susceptibility to treatment with said protease inhibitor, with the proviso that said mutation is not V32I, M46I, M46L, I47V, I50V, I54L, I54M or I84V.

In another embodiment, the invention provides a method of determining whether an individual infected with HIV has an increased likelihood of having a reduced susceptibility to treatment with a protease inhibitor, comprising detecting in the protease of said HIV the presence or absence of a mutation associated with reduced susceptibility to treatment with said protease inhibitor selected from the group consisting of: V11I, V11L, L33F, E34Q, K43T, G48M, I54A, I54S, I54T, Q58E, A71L, L76V, P79, V82A, V82F, N83D, I84A, I84C, T91A, T91S, T91V and C95F, wherein the presence of said mutation indicates that the individual has an increased likelihood of having reduced susceptibility to treatment with the protease inhibitor compared to an individual infected with a HIV without said mutation, e.g., a wild type or reference HIV.

5.8 CONSTRUCTING AN ALGORITHM

In one aspect, the present invention provides a method of constructing an algorithm that correlates genotypic data about a virus with phenotypic data about the virus. In one embodiment, the phenotypic data relate to the susceptibility of the virus to an anti-viral treatment. In another embodiment, the anti-viral treatment is an anti-viral compound. In another embodiment, the anti-viral compound is a protease inhibitor. In another embodiment, the protease inhibitor is amprenavir.

In one embodiment, the method of constructing the algorithm comprises creating a rule or rules that correlate genotypic data about a set of viruses with phenotypic data about the set of viruses.

In one embodiment, a data set comprising genotypic and phenotypic data about each virus in a set of viruses is assembled. Any method known in the art can be used to collect genotypic data about a virus. Examples of methods of collecting such data are provided above. Any method known in the art can be used for collecting phenotypic data about a virus. Examples of such methods are provided above. In a preferred embodiment, the data set comprises one or more RAMs as described above. In one embodiment, each genotypic datum is the sequence of all or part of a viral protein of a virus in the set of viruses. In another embodiment, each genotypic datum in the data set is a single amino acid change in a protein encoded by the virus, relative to a reference protein in the reference virus. In other embodiments, the genotype comprises two, three, four, five, six or more amino acid changes in the viral protein. In another embodiment, the virus is HIV, and the protein is HIV protease. In a preferred embodiment, the virus is HIV-1. In another embodiment, the reference protein is the protease from NL4-3 HIV.

In one embodiment, each phenotypic datum in the data set is the susceptibility to an anti-viral treatment of a virus in the set of viruses. In one embodiment, the anti-viral treatment is an anti-viral compound. In another embodiment, the anti-viral compound is a protease inhibitor. In a preferred embodiment, the protease inhibitor is amprenavir. In one embodiment, the susceptibility is measured as a change in the susceptibility of the virus relative to a reference virus. In another embodiment, the susceptibility is measured as a change in the $IC_{50}$ of the virus relative to a reference virus. In another embodiment, the change in $IC_{50}$ is represented as the fold-change in $IC_{50}$. In certain embodiments the virus is HIV. In a preferred embodiment, the virus is HIV-1. In another preferred embodiment, the reference HIV is NL4-3 HIV.

The genotypic and phenotypic data in the data set can be represented or organized in any way known in the art. In one embodiment, the data are displayed in the form of a graph. In this type of representation, the y-axis represents the fold change in $IC_{50}$ of a virus in the data set relative to a reference virus. Each point on the graph corresponds to one virus in the data set. The x-axis represents the number of mutations that a virus in the data set has. The position of the point indicates both the number of mutations and the fold change in anti-viral therapy treatment that the virus has, both measured relative to a reference strain. In another embodiment, the genotypic and phenotypic data in the data set are displayed in the form of a chart.

In one aspect, an algorithm is formulated that correlates the genotypic data with the phenotypic data in the data set. In one embodiment, a phenotypic cutoff point is defined. In a preferred embodiment, the phenotype is susceptibility to an anti-viral treatment. In another embodiment, the phenotype is change in sensitivity to an anti-viral treatment relative to a reference virus, and the cutoff point is the value above which a virus or population of viruses is defined as phenotypically resistant ("PT-R") to the anti-viral therapy and below which a virus or population of viruses is defined as phenotypically sensitive ("PT-S") to the anti-viral therapy. In some embodiments, the cutoff point is 2-fold, 2.5-fold, 3-fold, 5-fold, 10-fold, 15-fold, 20-fold, 30-fold, 40-fold, 50-fold or 100-fold greater than the $IC_{50}$ of a reference virus. In some embodiments, the phenotypic cutoff point is the clinical cutoff value as defined above. In a preferred embodiment, the virus is HIV and the anti-viral therapy is treatment with a protease inhibitor. In a preferred embodiment, the protease inhibitor is amprenavir.

In some embodiments, the phenotypic cutoff point is used to define a genotypic cutoff point. In one embodiment this is done by correlating the number of mutations in a virus of the data set with the phenotypic susceptibility of the virus. This can be done, for example, using a graph similar to one discussed above. A genotypic cutoff point is selected such that most viruses having more than that number of mutations in the data set are phenotypically resistant ("PT-R"), and most viruses having fewer than that number of mutations are phenotypically sensitive ("PT-S"). By definition, a virus in the data set with number of mutations equal to, or more than the genotypic cutoff is genotypically resistant ("GT-R") to the anti-viral treatment, and a virus in the data set with fewer than the genotypic cutoff number of mutations is genotypically sensitive ("GT-S") to the anti-viral treatment. Thus, in one embodiment, a genotypic cutoff point is selected that produces the greatest percentage of viruses in the data set that are either phenotypically resistant and genotypically resistant ("PT-R, GT-R"), or phenotypically sensitive and genotypically sensitive ("PT-S, GT-S").

While this algorithm can provide a useful approximation of the relationship between the genotypic and phenotypic data in the data set, in most cases there will be a significant number of strains that are genotypically sensitive but phenotypically resistant ("GT-S, PT-R"), or genotypically resistant but phenotypically sensitive ("GT-R, PT-S"). Thus, in a preferred embodiment, the algorithm is further modified to reduce the percentage of discordant results in the data set. This is done, for example, by removing from the data set each data point that corresponds to a virus population comprising a mixture of mutations including the wild-type, at a single position considered by the algorithm tested. This can have the effect of reducing the number of PT-S, GT-R results, thus lowering the overall percentage of discordant results and so improves the fit of the algorithm to a data set.

In another embodiment, differential weight values are assigned to one or more mutations observed in the data set. An algorithm that does not include this step assumes that each mutation in the data set contributes equally to the overall resistance of a virus or population of viruses to an anti-viral therapy. For example a mutation could be present in a data set that is almost always correlated with phenotypic resistance to an anti-viral treatment. That is, almost every virus that has the mutation is phenotypically resistant to the anti-viral treatment, even those strains having only one or two total mutations. In one embodiment, such mutations are "weighted," i.e., assigned an increased mutation score. A mutation can be assigned a weight of, for example, two, three, four, five, six, seven, eight or more. For example, a mutation assigned a weight of 2 will be counted as two mutations in a virus. Fractional weighting values can also be assigned. In another embodiment, values of less than 1, and of less than zero, can be assigned, wherein a mutation is associated with an increased sensitivity of the virus to the anti-viral treatment.

One of skill in the art will appreciate that there is a tradeoff involved in assigning an increased weight to certain mutations. As the weight of the mutation is increased, the number of GT-R, PT-S discordant results may increase. Thus, assigning a weight to a mutation that is too great may increase the overall discordance of the algorithm. Accordingly, in one embodiment, a weight is assigned to a mutation that balances the reduction in GT-S, PT-R discordant results with the increase in GT-R, PT-S discordant results.

In another embodiment, the interaction of different mutations in the data set with each other is also factored into the algorithm. For example, it might be found that two or more mutations behave synergistically, i.e., that the coincidence of the mutations in a virus contributes more significantly to the resistance of the virus than would be predicted based on the effect of each mutation independent of the other. Alternatively, it might be found that the coincidence of two or more mutations in a virus contributes less significantly to the resistance of the virus than would be expected from the contributions made to resistance by each mutation when it occurs independently. Also, two or more mutations may be found to occur more frequently together than as independent mutations. Thus, in one embodiment, mutations occurring together are weighted together. For example, only one of the mutations is assigned a weight of 1 or greater, and the other mutation or mutations are assigned a weight of zero, in order to avoid an increase in the number of GT-R, PT-S discordant results.

In another aspect, the phenotypic cutoff point can be used to define a genotypic cutoff point by correlating the number as well as the class of mutations in a virus of the data set with the phenotypic susceptibility of the virus. Examples of classes of mutations include, but are not limited to, primary amino acid mutations, secondary amino acid mutations, mutations in which the net charge on the polypeptide is conserved and mutations that do not alter the polarity, hydrophobicity or hydrophilicity of the amino acid at a particular position. Other classes of mutations that are within the scope of the invention would be evident to one of skill in the art, based on the teachings herein.

In one embodiment, an algorithm is constructed that factors in the requirement for one or more classes of mutations. In another embodiment, the algorithm factors in the requirement for a minimum number of one or more classes of mutations. In another embodiment, the algorithm factors in the requirement for a minimum number of primary or secondary mutations. In another embodiment, the requirement for a primary or a secondary mutation in combination with other mutations is also factored into the algorithm. For example, it might be found that a virus with a particular combination of mutations is resistant to an anti-viral treatment, whereas a virus with any mutation in that combination, alone or with other mutations that are not part of the combination, is not resistant to the anti-viral treatment.

By using, for example, the methods discussed above, the algorithm can be designed to achieve any desired result. In one embodiment, the algorithm is designed to maximize the overall concordance (the sum of the percentages of the PT-R, GT-R and the PT-S, GT-S groups, or 100 minus (percentage of the PT-S, GT-R+PT-R, GT-S groups). In preferred embodiments, the overall concordance is greater than about 75%, 80%, 85%, 90% or 95%. In another embodiment, the algorithm is designed to minimize the percentage of PT-R, GT-S results. In another embodiment, the algorithm is designed to minimize the percentage of PT-S, GT-R results. In another embodiment, the algorithm is designed to maximize the percentage of PT-S, GT-S results. In another embodiment, the algorithm is designed to maximize the percentage of PT-R, GT-R results.

At any point during the construction of the algorithm, or after it is constructed, it can be further tested on a second data set. In one embodiment, the second data set consists of viruses that are not included in the data set used to construct the algorithm, i.e., the second data set is a naive data set. In another embodiment, the second data set contains one or more viruses that were in the data set used to construct the algorithm and one or more viruses that were not in that data set. Use of the algorithm on a second data set, particularly a naive data set, allows the predictive capability of the algorithm to be assessed. Thus, in one embodiment, the accuracy of an algorithm is assessed using a second data set, and the rules of the algorithm are modified as described above to improve its accuracy. In a preferred embodiment, an iterative approach is used to create the algorithm, whereby an algorithm is tested and then modified repeatedly until a desired level of accuracy is achieved.

In one aspect, the construction or implementation of the algorithm can begin with a few "starting mutations" and proceed in steps in which it factors in the presence of certain mutations or classes of mutations. In one embodiment, the algorithm factors in the presence of either I50V on its own or, any one or more of V32I, I54L or M, I84A or V plus two secondary mutations. Any of the secondary mutations listed in Table 5 can be used. Next, the algorithm factors in other mutations in addition to the starting mutations. The additional mutations can include, e.g., 82F and I84C as well as any one or more of 54A, 54S or 54T. In one embodiment, the algorithm, in all future stages, factors in a minimum number of secondary mutations. In a more particular embodiment, the algorithm, in all future stages, factors in at least 2 secondary mutations. The algorithm can then factor in the presence of additional mutations, e.g., the combination of 33F and 82A. When the algorithm factors in the combination of 2 or more mutations, it is generally understood that both mutations, e.g., 33F and 82A, be present in the same virus (or sample). Finally, the algorithm can factor in additional combinations, e.g., the combination of 46I or 46L with any one or more of 47V, 54V, 71L, 76V, or 82A. During the construction or implementation of an algorithm as described above, a decrease in the overall discordance as well as the percentage of data in the PT-R, GT-S group decreased with each step of the algorithm is indicative that the algorithm improved each time in correctly predicting the mutations and combinations of mutations that led to phenotypic resistance.

5.9 USING AN ALGORITHM TO PREDICT THE SUSCEPTIBILITY OF A VIRUS

In another aspect, the present invention also provides a method for using an algorithm of the invention to predict the phenotypic susceptibility of a virus or a derivative of a virus to an anti-viral treatment based on the genotype of the virus. In one embodiment, the method comprises detecting, in the virus or derivative of the virus, the presence or absence of one or more RAMs, applying the rules of the algorithm to the detected RAMs, wherein a virus that satisfies the rules of the algorithm is genotypically resistant to the anti-viral treatment, and a virus that does not satisfy the rules of the algorithm is genotypically sensitive to the anti-viral treatment. In another embodiment, the method comprises detecting, in the virus or derivative of the virus, the presence or absence of one or more RAMs, applying the rules of the algorithm to the detected RAMs, wherein a score equal to, or greater than the genotypic cutoff score indicates that the virus is genotypically resistant to the anti-viral treatment, and a score less than the genotypic cutoff score indicates that the virus is genotypically sensitive to the anti-viral treatment.

The algorithm of this invention can be used for any viral disease where anti-viral drug susceptibility is a concern, as discussed above in Section 5.4.1. In certain embodiments the assay of the invention can be used to determine the susceptibility of a retrovirus to an anti-viral drug. In a preferred embodiment, the retrovirus is HIV. Preferably, the virus is HIV-1.

The anti-viral agent of the invention could be any treatment effective against a virus. It is useful to the practice of this invention, for example, to understand the structure, life cycle and genetic elements of the viruses which can be tested in the drug susceptibility test of this invention. These would be known to one of ordinary skill in the art and provide, for example, key enzymes and other molecules at which the anti-viral agent can be targeted. Examples of anti-viral agents of the invention include, but are not limited to, nucleoside reverse transcriptase inhibitors such as AZT, ddI, ddC, d4T, 3TC, abacavir, nucleotide reverse transcriptase inhibitors such as tenofovir, non-nucleoside reverse transcriptase inhibitors such as nevirapine, efavirenz, delavirdine, fusion inhibitors such as T-20 and T-1249 and protease inhibitors such as saquinavir, ritonavir, indinavir, nelfinavir, amprenavir and lopinavir.

In some embodiments of the invention, the anti-viral agents are directed at retroviruses. In certain embodiments, the anti-viral agents are protease inhibitors such as saquinavir, ritonavir, indinavir, nelfinavir, amprenavir and lopinavir. In a preferred embodiment, the anti-viral agent is amprenavir.

Some mutations associated with reduced susceptibility to treatment with an anti-viral agent are known in the art. See, e.g., Maguire et al., 2002, *Antimicrob Agents Chemother* 46:731-738. Others can be determined by methods described in Sections 5.4-5.8 above. For example, Table 1 provides a list of mutations associated with reduced susceptibility to amprenavir.

5.10 USING AN ALGORITHM TO PREDICT THE EFFECTIVENESS OF ANTI-VIRAL TREATMENT FOR AN INDIVIDUAL

In another aspect, the present invention also provides a method for using an algorithm of the invention to predict the effectiveness of an anti-viral treatment for an individual infected with a virus based on the genotype of the virus to the anti-viral treatment. In one embodiment, the method comprises detecting, in the virus or derivative of the virus, the presence or absence of one or more RAMs, applying the rules of the algorithm to the detected RAMs, wherein a virus that satisfies the rules of the algorithm is genotypically resistant to the anti-viral treatment, and a virus that does not satisfy the rules of the algorithm is genotypically sensitive to the anti-viral treatment. In another embodiment, the method comprises detecting, in the virus or a derivative of the virus, the presence or absence of one or more RAMs, applying the rules of the algorithm to the detected RAMs, wherein a score equal to, or greater than the genotypic cutoff score indicates that the virus is genotypically resistant to the anti-viral treatment, and a score less than the genotypic cutoff score indicates that the virus is genotypically sensitive to the anti-viral treatment.

As described in Section 5.4.1 above, the algorithm of the invention can be used for any viral disease where anti-viral drug susceptibility is a concern and the anti-viral agent of the invention could be any treatment effective against a virus. In certain embodiments the assay of the invention is used to determine the susceptibility of a retrovirus to an anti-viral drug. In a preferred embodiment, the retrovirus is HIV. Preferably, the virus is HIV-1. In some embodiments of the invention, the anti-viral agents are directed at retroviruses. In certain embodiments, the anti-viral agents are protease inhibitors such as saquinavir, ritonavir, indinavir, nelfinavir, amprenavir and lopinavir. In a preferred embodiment, the anti-viral agent is amprenavir.

As described in Section 5.9 above, mutations associated with reduced susceptibility to treatment with an anti-viral agent may be obtained from the art or determined by methods described above in Sections 5.4-5.8.

In some embodiments, the present invention provides a method for monitoring the effectiveness of an anti-viral treatment in an individual infected with a virus and undergoing or having undergone prior treatment with the same or different anti-viral treatment, comprising, detecting, in a sample of said individual, the presence or absence of an amino acid residue associated with reduced susceptibility to treatment the anti-viral treatment, wherein the presence of the residue correlates with a reduced susceptibility to treatment with the anti-viral treatment.

5.11 CORRELATING SUSCEPTIBILITY TO ONE ANTI-VIRAL TREATMENT WITH SUSCEPTIBILITY TO ANOTHER ANTI-VIRAL TREATMENT

In another aspect, the present invention provides a method for using an algorithm of the invention to predict the effectiveness of an anti-viral treatment against a virus based on the genotypic susceptibility of the virus to a different anti-viral treatment. In one embodiment, the method comprises detecting, in a virus or a derivative of a virus, the presence or absence of one or more mutations correlated with resistance to an anti-viral treatment and applying the rules of an algorithm of the invention to the detected mutations, wherein a virus that satisfies the rules of the algorithm is genotypically resistant to the anti-viral treatment, and a virus that does not satisfy the rules of the algorithm is genotypically sensitive to the anti-viral treatment. In another embodiment, the method comprises detecting, in the virus or a derivative of the virus, the presence or absence of one or more mutations correlated with resistance to an anti-viral treatment and applying the rules of the algorithm to the detected mutations, wherein a score equal to, or greater than the genotypic cutoff score indicates that the virus is genotypically resistant to a different anti-viral treatment, and a score less than the genotypic cutoff score indicates that the virus is genotypically sensitive to a different anti-viral treatment. In another embodiment, the two anti-viral treatments affect the same viral protein. In another embodiment, the two anti-viral treatments are both protease inhibitors. Examples of protease inhibitors include, but are not limited to, saquinavir, ritonavir, indinavir, nelfinavir, amprenavir and lopinavir. In another embodiment, one of the two anti-viral treatments is amprenavir. In another embodiment, a mutation correlated with resistance to one protease inhibitor is also correlated with resistance to another protease inhibitor.

6. EXAMPLES

The following examples are provided to illustrate certain aspects of the present invention and not intended as limiting the subject matter thereof.

6.1 Example 1

Analysis of Patient Samples to Identify Resistance-Associated Mutations

This example demonstrates a method of analyzing patient samples so as to identify mutations that are associated either with increased or with decreased susceptibility to protease inhibitors such as amprenavir.

In order to determine the relationship between an HIV-1 strain's protease sequence and its susceptibility to treatment with amprenavir, a data set of 10,513 samples was used. From this data set, all "wild type" samples, i.e., samples with FC<2 for all protease inhibitors and no drug selected mutation were removed. FIG. 2 shows a flow-chart depicting the steps followed to arrive at a final set of samples that was analyzed in detail. The drug-selected PI mutations used as a criterion for removing a sample were those that occurred at amino acid positions 23, 24, 30, 32, 33F, 46, 48, 50, 53, 54, 82 (except 82I), 84, 88 or 90 of the HIV protease (FIG. 2). Next, samples with the same genotype were removed from the data set. This resulted in a data set of 4414 patient plasma samples that was analyzed genotypically as well as phenotypically.

The phenotypic assay was conducted using the PHENOSENSE™ (Virologic, South San Francisco, Calif.) HIV assay (Petropoulos et al., 2000, *Antimicrob. Agents Chemother.* 44:920-928; U.S. Pat. Nos. 5,837,464 and 6,242,187). $IC_{50}$ values for amprenavir were obtained for the HIV-1 from the patient sample. This was compared to the $IC_{50}$ for amprenavir against the NL4-3 (GenBank Accession No. AF324493) reference viral strain. Phenotypic data were expressed as "fold change" (or log fold change) in 50% inhibitory concentration ($IC_{50}$) of amprenavir. The fold $IC_{50}$ values were calculated by dividing the $IC_{50}$ of amprenavir against the HIV-1 from the patient plasma sample by the $IC_{50}$ for amprenavir against the NL4-3 (GenBank Accession No. AF324493) reference viral strain. The cut-off used to define phenotypic resistance to APV was 2.5-fold. This cut-off value has not been derived from clinical outcome studies, however the 2.5-fold threshold is meaningful because: strong correlations exist between phenotypic results using this cutoff and clinical response data in cohorts that included patients receiving amprenavir (Haubrich et al., 2001, *Antivir Ther* 6 (suppl 1):63; Katzenstein et al., 2002, *9th CROI*, Seattle, Wash.); reductions in susceptibility to amprenavir observed in patients who experienced viral load rebound while using amprenavir as their first PI are modest (as low as 2-3 fold) (Maguire et al., 2002, *Antimicrob Agents Chemother* 46:731-738); and the 99th percentile for the distribution of amprenavir FC in genotypically wild-type viruses using the PhenoSense™ Assay was 2.1-fold. For those mutants that had an amprenavir FC>2.5, % R and % S values were calculated according to the formulae:

% $R$=(number of samples with mutant that were PT-R)/(total no. of PT-R samples)

% $S$=(number of samples with mutant that were PT-S)/(total no. of PT-S samples)

In order to define the genotypic changes correlated with reduced susceptibility to amprenavir, the entire amino acid sequences of HIV proteases in each of the patients' samples were analyzed. Mutations were compared to the protease sequence of the NL4-3 (GenBank Accession No. AF324493) reference strain. All positions that were mutated in at least 1% of the 4414 samples (i.e., in at least 44 samples) were analyzed in detail. Mixtures were counted as mutants. In some cases, different amino acids at the same position were grouped together (e.g., position 67), whereas at other positions (e.g., position 82), the different mutations (e.g., V82A, F, S or T) were counted separately.

P values were calculated for determining the statistical significance of the phenotypic and genotypic correlations. For each mutation the number of samples in the data set that had an APV FC<2.5 or an APV FC>2.5 were compared in samples with or without the mutation in question. A 2×2 table was constructed and the P value was calculated using Fisher's Exact test. Mutations that had a P<0.001 and % R/% S>3 were considered to be associated with reduced susceptibility to amprenavir; while mutations that had a P<0.001 and a % R/% S<0.3 were considered to be associated with increased susceptibility to amprenavir. Other values for P, e.g., P<0.05 and % R/% S ratios, e.g., % R/% S>4 or 5 and % R/% S<0.25 or 0.2, which are within the scope of the invention, will be evident to one of skill in the art based on the teachings herein. Table 2 provides the entire list of mutations that were analyzed and Table 1 provides a list of mutations that were associated with either reduced or increased susceptibility to amprenavir (i.e., those mutations with P<0.001 and % R/% S>3 or % R/% S<0.3).

6.2 Example 2

Correlation of Amprenavir Susceptibility to the Mutations in HIV Protease

This example demonstrates the construction of an algorithm that correlates the mutations in the protease gene of an HIV with its susceptibility to amprenavir.

A data set of 4414 patient plasma samples was analyzed and mutations associated with reduced susceptibility to amprenavir were identified, as described in Example 1. The phenotypic susceptibility to amprenavir (amprenavir fold change) was analyzed as a function of the number of mutations in the protease of the HIV present in a patient's plasma sample. The fold change for each sample was calculated by dividing the $IC_{50}$ of amprenavir against the HIV from the patient's plasma sample by the $IC_{50}$ for amprenavir against the NL4-3 (GenBank Accession No. AF324493) reference viral strain. The genotype data was obtained by sequencing the protease of the HIV present in each patient's sample and determining the sequence changes with respect to the sequence of the NL4-3 (GenBank Accession No. AF324493) HIV. The amino sequence for the NL4-3 protease is provided in SEQ. ID. No. 1 (FIG. 3A) and the nucleic acid sequence for the NL4-3 protease gene is provided in SEQ. ID. No. 2 (FIG. 3B).

The mutations used in a preliminary round of analysis were the primary amprenavir mutations I54M, I50V, V32I, I54L, I84V (identified by Maguire et al., 2002, *Antimicrob Agents Chemother* 46:731-738) and I84A. Samples were defined as genotypically resistant ("GT-R") if any of the above mutations (V32I, I50V, I54L or M, or I84A or V) were present. Data were analyzed using univariate analysis (P<0.001 by Fisher's exact test was considered significant) and regression tree (CART) analysis (Statview 5.0 software; SAS, Cary, N.C.).

The results of this analysis were divided into four groups. Viruses that contain none of the above-identified mutations in their protease and are phenotypically and genotypically sensitive (PT-S, GT-S) to amprenavir were present in 1635, or 37% of the 4414 samples. Viruses that contain at least one of the above-identified mutations and are phenotypically and genotypically resistant (PT-R, GT-R) to amprenavir (APV FC>2.5; Log amprenavir fold change>0.398) were present in 1698, or 38.5% of the samples. The other two groups correspond to the "exceptions" where a virus was predicted based on genotype (number of mutations) to be susceptible, but was phenotypically (based on Log amprenavir fold change) resistant (PT-R, GT-S) or where a virus was predicted based on genotype to be resistant, but was phenotypically (based on Log amprenavir fold change) susceptible (PT-S, GT-R).

Nearly one quarter of the initial genotypic interpretations were discordant with the observed phenotypic results. 865 samples, corresponding to 19.6% of the samples lacked any of the above-identified mutations, but, contrary to expectations, were found to be phenotypically resistant to amprenavir (PT-R, GT-S). Conversely, some viruses that had one or more of the above-identified mutations did not exhibit any greater resistance to amprenavir than did the WT strain (PT-S, GT-R) (216 samples (4.9%)).

6.3 Example 3

Analysis of the PT-R, GT-S Discordant Group

This example demonstrates that certain mutations and certain combinations of mutations make a greater contribution to amprenavir resistance than others.

The samples in the PT-R, GT-S group of Example 2 correspond to viruses with no known primary mutations in the HIV protease associated with reduced susceptibility to amprenavir (i.e., none of V32I, I50V, I54L or M, or I84A or V). These viruses were phenotypically resistant (had an amprenavir fold change greater than 2.5) but were predicted to be genotypically sensitive (because they had none of the known primary mutations). Since the majority of the discordance for amprenavir is of the PT-R, GT-S type, the development of the algorithm focused on mutations which were associated with this phenotype, and not those that simply appeared along with a known mutation. Therefore, samples with known mutations (GT-R) were removed. This resulted in a total of 2499 remaining samples. 34% of these had APV FC>2.5 (FIG. 4).

CART (Classification and Regression Tree) analysis enabled the identification of the most important variables for defining APV reduced susceptibility. FIG. 4 shows the tree generated by the analysis. The analysis resulted in the identification of a list of mutations that contribute to reduced susceptibility to amprenavir: V11I, L, V32I, L33F, E34Q, K43T, I47V, G48M, I50V, I54M, I54S, I54A, I54L, I54T, A71L, L76V, V82F, I84A and T91. Further, the analysis also enabled the identification of some mutations that were not independently associated with reduced susceptibility to amprenavir, but were likely to be associated with reduced susceptibility to amprenavir in combination with other mutations. This list included: L10F, L10F, L24I, E35, M46I, M46L, G48V, F53L, I54V, Q58E, C67, A71V, G73, V82S, V82A, I84A and L90M. All possible pairs of these mutations were tested and Fisher's Exact test performed, as described above. The results are summarized in Table 3 as well as in FIG. 5. FIG. 5 is a matrix of pairs of mutations associated with resistance to amprenavir. The numbers in each cell are the odds ratio (% R:% S) for that pair of mutations and the numbers in brackets indicate the number of samples with that pair. Only those cells for which the corresponding pair had P<0.001 (as determined by Fisher's exact test) have numbers in them.

Pairs of the above mutations with strong associations with reduced susceptibility to amprenavir were tested again by CART analysis as shown in FIG. 6.

Thus, it is evident that the PT-R, GT-S group can be associated with the presence of mutations that are not independently associated with reduced susceptibility to amprenavir, but contribute to reduced susceptibility to amprenavir in combination with other mutations.

6.4 Example 4

Algorithm and Demonstration of its Accuracy

This example demonstrates the construction of an algorithm that reduces the incidence of PT-R, GT-S results by requiring certain mutations, classes of mutations and combinations of mutations.

As described in Example 3, from a starting data set of 4414 samples, those samples with APV GT-R were removed, resulting in a data set of 2499 samples. The final rules were formulated based on the results observed with both data sets, those with 4414 and 2499 samples (these data were called the "training data"). The accuracy of the devised rules or algorithm was evaluated based on the accuracy with which the susceptibility of the viruses could be determined based solely on the algorithm. When discrepancies were seen between the predictions and the observed results, the algorithm was modified so that it remained consistent with the observed results. The rules devised from the training data were then tested on a "validation data set" of patients. The validation data set was obtained by starting with a data set of 11,768 samples. From this data set, following the steps described in Example 1, all samples with FC<2 for all protease inhibitors and no drug selected mutation were removed. Next, samples with the same genotype were removed. Finally samples that were present in the training data set were excluded. This resulted in a validation data set of 1634 samples that was used to test the accuracy of the algorithm derived using only the training data set.

Table 4 provides a summary of the rules applied at each round or version of the development of the algorithm and the results obtained for the training data set with 4414 samples and the validation data set with 1634 samples. The first column provides the rules used for each round of testing. The rules are cumulative, i.e., the rules for each round is added to the rules for the round preceding it.

The next four columns provide, in order, the number of samples in the PT-S, GT-S, the PT-R, GT-R, the PT-R, GT-S and the PT-S, GT-R groups. The number in the PT-S, GT-R column excludes the PT-S, GT-R samples associated with mixtures at a primary or at least two secondary positions. Because mixtures were counted as mutants, a sample with say, less than 50% mutant, would be counted as a mutant for genotypic purposes, even though its phenotypic resistance may not be as high as a true mutant. This gives rise to more samples in the PT-S, GT-R group, than expected based on the rules alone.

The next 3 columns of Table 4 provide, in order, the percentage of samples that are in the PT-R, GT-S and the PT-S, GT-R groups and the overall discordance (the sum of the percentages of the PT-R, GT-S and the PT-S, GT-R groups, or 100−(percentage of the PT-S, GT-S+PT-R, GT-R groups).

The algorithm began with requiring the "starting mutations," which refers to either I50V on its own or, any one or more of V32I, I54L or M, I84A or V plus two secondary mutations. Any of the secondary mutations listed in Table 5 can be used. In the next round, 82F and I84C as well as any one or more of 54A, 54S or 54T were added. From this round on, at least 2 secondary mutations ("2mut" in Table 4) were needed. In the next round the combination of 33F and 82A was added. This required that both, 33F and 82A be present in the same virus (or sample). In the last round, the combination of 46I or 46L with any one or more of 47V, 54V, 71L, 76V, or 82A was added.

The overall discordance as well as the percentage of data in the PT-R, GT-S group decreased with each round of the algorithm, indicating that the algorithm improved each time in correctly predicting the mutations and combinations of mutations that led to phenotypic resistance. For the training data set, the total discordance decreased significantly, from 24.5% in the first round to 14.7% in the last round and the number of samples in the PT-R, GT-S group correspondingly decreased from 19.6% to 5.9% of the total samples.

The validation data set had a lower starting total discordance (15.8%) and fewer samples in the PT-R, GT-S group (12.8%) as compared to the training data set. Without being bound by theory, it is believed that this was because the validation data set contained fewer samples with complex viral protease genotypes. The accuracy of the algorithm, developed using samples only form the training data set, to correctly predict the susceptibility of any virus to amprenavir is demonstrated by its performance on the validation data set. The application of the final algorithm, i.e., the rules in the last row of the training data set in Table 4 (denoted as "final algorithm" in the validation data set section) reduced the total discordance as well as the percentage of data in the PT-R, GT-S group significantly, from 15.8% to 10.3% and from 12.8% to 4.4%, respectively.

6.5 Example 5

Effect of the N88S Mutation

This example demonstrates that N88S can re-sensitize viruses containing mutations that are strongly associated with reduced susceptibility to amprenavir.

N88S is a protease inhibitor resistance mutation and is selected in vitro by atazanavir (Gong et al., 2000, *Antimicrob Agents Chemother* 44:2319-26). It is also seen following treatment with indinavir (Condra et al., 1996, *J. Virol.* 70:8270-8276). As can be seen from Tables 1 and 2, the HIV protease mutation N88S is correlated with an increased susceptibility of a virus in which it is present to amprenavir. I50V, on the other hand, has the opposite effect and is correlated with reduced susceptibility. A sample from an HIV-infected patient was analyzed genotypically and phenotypically. The sample was found to contain L10I, I13V, E35D, M36I, R41K, I50V, L63P, A71V, N88N/S (i.e., a mixture of N and S at position 88), and L90M mutations in HIV protease. Phenotypically, the following fold changes in $IC_{50}$ to different protease inhibitors were seen: amprenavir: 4.1; indinavir: 1.4; lopinavir: 3.3; nelfinavir: 5.3; ritonavir: 11; and saquinavir: 3.6.

Clones from the population were selected so as to isolate some clones with the N88S mutation and some without it. Resistance test vector pools constructed from the original plasma sample (Petropoulos et al., 2000, *Antimicrob Agents Chemother* 44:920-8) were transformed into *E. Coli*, and plasmid DNA from individual colonies was screened in the PhenoSense® assay for protease genotype. A total of 21 clones were isolated, 3 with only I50V, 15 with I50V and L90M, and 3 with I50V and N88S, in addition to the other mutations present in the pool. FIG. 7 summarizes the phenotypic susceptibility to the different protease inhibitors as mean fold changes (FC) for each group of clones. Clones with I50V only, or I50V plus L90M, displayed marked reductions in susceptibility to amprenavir (13-17 FC), lopinavir (7-9 FC), nelfinavir (7-10 FC), and ritonavir (12-20 FC). The effect of L90M was small in each case, except for saquinavir (1.8-fold increase in FC with L90M). However, when N88S was present in combination with I50V, amprenavir susceptibility was increased by a factor of 14.5. As seen in FIG. 7, the fold change for a virus containing I50V, but not N88S (bar 1 for APV) is about 17-fold. However, the fold change dropped to wild type level (1.2 FC) when the virus contained N88S in addition to I50V (bar 2 for APV). The levels of lopinavir and ritonavir susceptibility were also increased (by a 1.7-fold and a 1.4-fold decrease in $IC_{50}$, respectively) in the presence of N88S. Conversely, susceptibility to nelfinavir and atazanavir decreased in the presence of N88S, as is seen by a 2.1-fold and a 2.3-fold increase, respectively, in $IC_{50}$.

These results demonstrate that N88S can completely re-sensitize HIV-1 containing the I50 mutation to amprenavir. Thus, if N88S can be maintained, future treatment options for patients who harbor I50V-containing virus may include amprenavir, perhaps in combination with ritonavir. As seen in the FIG. 7, N88S also lowered the level of resistance to lopinavir imparted by I50V. The congruence of directionality in the effect of N88S on amprenavir and lopinavir is consistent with observations regarding cross-resistance between these two PIs.

All references cited herein are incorporated by reference in their entireties.

The examples provided herein, both actual and prophetic, are merely embodiments of the present invention and are not intended to limit the invention in any way.

TABLE 1

Mutations Associated with Resistance to Amprenavir

| Mutation | PT-S, mt | PT-S, wt | PT-R, mt | PT-R, wt | P value | % mt S | % mt R | % R/% S |
|---|---|---|---|---|---|---|---|---|
| G48M | 1 | 1849 | 34 | 2530 | <0.0001 | 0.0 | 1.3 | 24.5 |
| I54S | 2 | 1848 | 63 | 2501 | <0.0001 | 0.1 | 2.5 | 22.7 |
| I50V | 9 | 1841 | 187 | 2377 | <0.0001 | 0.5 | 7.3 | 15.0 |
| T91ASV** | 5 | 1845 | 102 | 2462 | <0.0001 | 0.3 | 4.0 | 14.7 |
| I47V | 20 | 1830 | 327 | 2237 | <0.0001 | 1.1 | 12.8 | 11.8 |
| V11IL** | 18 | 1832 | 269 | 2295 | <0.0001 | 1.0 | 10.5 | 10.8 |
| V32I | 28 | 1822 | 358 | 2206 | <0.0001 | 1.5 | 14.0 | 9.2 |
| E34Q | 15 | 1835 | 157 | 2407 | <0.0001 | 0.8 | 6.1 | 7.6 |
| L33F | 81 | 1769 | 819 | 1745 | <0.0001 | 4.4 | 31.9 | 7.3 |
| A71L | 4 | 1846 | 38 | 2526 | <0.0001 | 0.2 | 1.5 | 6.8 |
| L76V | 14 | 1836 | 132 | 2432 | <0.0001 | 0.8 | 5.2 | 6.8 |

TABLE 1-continued

Mutations Associated with Resistance to Amprenavir

| Mutation | PT-S, mt | PT-S, wt | PT-R, mt | PT-R, wt | P value | % mt S | % mt R | % R/% S |
|---|---|---|---|---|---|---|---|---|
| I54A | 9 | 1841 | 78 | 2486 | <0.0001 | 0.5 | 3.0 | 6.2 |
| I54L | 32 | 1818 | 266 | 2298 | <0.0001 | 1.7 | 10.4 | 6.0 |
| K43T | 46 | 1804 | 365 | 2199 | <0.0001 | 2.5 | 14.2 | 5.7 |
| I84V | 167 | 1683 | 1122 | 1442 | <0.0001 | 9.0 | 43.8 | 4.9 |
| I54T | 11 | 1839 | 72 | 2492 | <0.0001 | 0.6 | 2.8 | 4.7 |
| V82F | 17 | 1833 | 102 | 2462 | <0.0001 | 0.9 | 4.0 | 4.3 |
| C95F | 27 | 1823 | 141 | 2423 | <0.0001 | 1.5 | 5.5 | 3.8 |
| P79** | 19 | 1831 | 96 | 2468 | <0.0001 | 1.0 | 3.7 | 3.6 |
| N83D | 11 | 1839 | 54 | 2510 | <0.0001 | 0.6 | 2.1 | 3.5 |
| Q58E | 82 | 1768 | 385 | 2179 | <0.0001 | 4.4 | 15.0 | 3.4 |
| I84A | 2 | 1848 | 9 | 2555 | 0.1343 | 0.1 | 0.4 | 3.2 |
| I84C | 1 | 1849 | 8 | 2556 | 0.0891 | 0.05 | 0.31 | 5.8 |
| E65D* | 41 | 1809 | 19 | 2545 | <0.0001 | 2.2 | 0.7 | 0.3 |
| D30N* | 357 | 1493 | 67 | 2497 | <0.0001 | 19.3 | 2.6 | 0.1 |
| N88S* | 91 | 1759 | 4 | 2560 | <0.0001 | 4.9 | 0.2 | 0.03 |

*Associated with increased susceptibility (sensitivity) to amprenavir.
**All variants treated equally.
Number of samples = 4414.
%R: Percent of samples with mutation compared to all PT-R, GT-S samples.
%S: Percent of samples with mutation compared to all PT-S, GT-S samples.

TABLE 2

Mutations Analyzed to Determine Resistance or Sensitivity to Amprenavir

| Mutation | PT-S, mt | PT-S, wt | PT-R, mt | PT-R, wt | P value | % mt S | % mt R | % R/% S | p < 0.001 | ratio > 3 | ratio < 0.3 |
|---|---|---|---|---|---|---|---|---|---|---|---|
| I54M | 5 | 1845 | 233 | 2331 | <0.0001 | 0.3 | 9.1 | 33.6 | 1 | 1 | 0 |
| G48M | 1 | 1849 | 34 | 2530 | <0.0001 | 0.0 | 1.3 | 24.5 | 1 | 1 | 0 |
| I54S | 2 | 1848 | 63 | 2501 | <0.0001 | 0.1 | 2.5 | 22.7 | 1 | 1 | 0 |
| I50V | 9 | 1841 | 187 | 2377 | <0.0001 | 0.5 | 7.3 | 15.0 | 1 | 1 | 0 |
| T91ASV | 5 | 1845 | 102 | 2462 | <0.0001 | 0.3 | 4.0 | 14.7 | 1 | 1 | 0 |
| I47V | 20 | 1830 | 327 | 2237 | <0.0001 | 1.1 | 12.8 | 11.8 | 1 | 1 | 0 |
| V11IL | 18 | 1832 | 269 | 2295 | <0.0001 | 1.0 | 10.5 | 10.8 | 1 | 1 | 0 |
| V32I | 28 | 1822 | 358 | 2206 | <0.0001 | 1.5 | 14.0 | 9.2 | 1 | 1 | 0 |
| E34Q | 15 | 1835 | 157 | 2407 | <0.0001 | 0.8 | 6.1 | 7.6 | 1 | 1 | 0 |
| L33F | 81 | 1769 | 819 | 1745 | <0.0001 | 4.4 | 31.9 | 7.3 | 1 | 1 | 0 |
| A71L | 4 | 1846 | 38 | 2526 | <0.0001 | 0.2 | 1.5 | 6.8 | 1 | 1 | 0 |
| L76V | 14 | 1836 | 132 | 2432 | <0.0001 | 0.8 | 5.2 | 6.8 | 1 | 1 | 0 |
| I54A | 9 | 1841 | 78 | 2486 | <0.0001 | 0.5 | 3.0 | 6.2 | 1 | 1 | 0 |
| I54L | 32 | 1818 | 266 | 2298 | <0.0001 | 1.7 | 10.4 | 6.0 | 1 | 1 | 0 |
| K43T | 46 | 1804 | 365 | 2199 | <0.0001 | 2.5 | 14.2 | 5.7 | 1 | 1 | 0 |
| I84V | 167 | 1683 | 1122 | 1442 | <0.0001 | 9.0 | 43.8 | 4.9 | 1 | 1 | 0 |
| I54T | 11 | 1839 | 72 | 2492 | <0.0001 | 0.6 | 2.8 | 4.7 | 1 | 1 | 0 |
| V82F | 17 | 1833 | 102 | 2462 | <0.0001 | 0.9 | 4.0 | 4.3 | 1 | 1 | 0 |
| C95F | 27 | 1823 | 141 | 2423 | <0.0001 | 1.5 | 5.5 | 3.8 | 1 | 1 | 0 |
| P79X | 19 | 1831 | 96 | 2468 | <0.0001 | 1.0 | 3.7 | 3.6 | 1 | 1 | 0 |
| N83D | 11 | 1839 | 54 | 2510 | <0.0001 | 0.6 | 2.1 | 3.5 | 1 | 1 | 0 |
| Q58E | 82 | 1768 | 385 | 2179 | <0.0001 | 4.4 | 15.0 | 3.4 | 1 | 1 | 0 |
| I84A | 2 | 1848 | 9 | 2555 | 0.1343 | 0.1 | 0.4 | 3.2 | 0 | 1 | 0 |
| L89 | 90 | 1760 | 379 | 2185 | <0.0001 | 4.9 | 14.8 | 3.0 | 1 | 0 | 0 |
| F53 | 84 | 1766 | 348 | 2216 | <0.0001 | 4.5 | 13.6 | 3.0 | 1 | 0 | 0 |
| I54 | 456 | 1394 | 1857 | 707 | <0.0001 | 24.7 | 72.4 | 2.9 | 1 | 0 | 0 |
| F53L | 80 | 1770 | 316 | 2248 | <0.0001 | 4.3 | 12.3 | 2.8 | 1 | 0 | 0 |
| G73 | 214 | 1636 | 834 | 1730 | <0.0001 | 11.6 | 32.5 | 2.8 | 1 | 0 | 0 |
| K55 | 98 | 1752 | 378 | 2186 | <0.0001 | 5.3 | 14.7 | 2.8 | 1 | 0 | 0 |
| A22 | 12 | 1838 | 46 | 2518 | 0.0007 | 0.6 | 1.8 | 2.8 | 1 | 0 | 0 |
| L24 | 84 | 1766 | 317 | 2247 | <0.0001 | 4.5 | 12.4 | 2.7 | 1 | 0 | 0 |
| G48 | 86 | 1764 | 312 | 2252 | <0.0001 | 4.6 | 12.2 | 2.6 | 1 | 0 | 0 |
| I66 | 58 | 1792 | 206 | 2358 | <0.0001 | 3.1 | 8.0 | 2.6 | 1 | 0 | 0 |
| G48V | 76 | 1774 | 268 | 2296 | <0.0001 | 4.1 | 10.5 | 2.5 | 1 | 0 | 0 |
| Q92 | 68 | 1782 | 238 | 2326 | <0.0001 | 3.7 | 9.3 | 2.5 | 1 | 0 | 0 |
| L24I | 79 | 1771 | 273 | 2291 | <0.0001 | 4.3 | 10.6 | 2.5 | 1 | 0 | 0 |
| L10F | 159 | 1691 | 546 | 2018 | <0.0001 | 8.6 | 21.3 | 2.5 | 1 | 0 | 0 |
| V82S | 20 | 1830 | 67 | 2497 | 0.0003 | 1.1 | 2.6 | 2.4 | 1 | 0 | 0 |
| I54V | 410 | 1440 | 1249 | 1315 | <0.0001 | 22.2 | 48.7 | 2.2 | 1 | 0 | 0 |
| C67 | 62 | 1788 | 187 | 2377 | <0.0001 | 3.4 | 7.3 | 2.2 | 1 | 0 | 0 |
| G48S | 1 | 1849 | 3 | 2561 | 0.6442 | 0.0 | 0.1 | 2.2 | 0 | 0 | 0 |
| I85 | 105 | 1745 | 309 | 2255 | <0.0001 | 5.7 | 12.0 | 2.1 | 1 | 0 | 0 |
| M46I | 439 | 1411 | 1288 | 1276 | <0.0001 | 23.7 | 50.2 | 2.1 | 1 | 0 | 0 |
| M46 | 605 | 1245 | 1758 | 806 | <0.0001 | 32.7 | 68.6 | 2.1 | 1 | 0 | 0 |
| K20R | 204 | 1646 | 583 | 1981 | <0.0001 | 11.0 | 22.7 | 2.1 | 1 | 0 | 0 |
| M46L | 184 | 1666 | 518 | 2046 | <0.0001 | 10.0 | 20.2 | 2.0 | 1 | 0 | 0 |

TABLE 2-continued

Mutations Analyzed to Determine Resistance or Sensitivity to Amprenavir

| Mutation | PT-S, mt | PT-S, wt | PT-R, mt | PT-R, wt | P value | % mt S | % mt R | % R/% S | p < 0.001 | ratio > 3 | ratio < 0.3 |
|---|---|---|---|---|---|---|---|---|---|---|---|
| V82A | 418 | 1432 | 1168 | 1396 | <0.0001 | 22.6 | 45.6 | 2.0 | 1 | 0 | 0 |
| V82 | 586 | 1264 | 1562 | 1002 | <0.0001 | 31.7 | 60.9 | 1.9 | 1 | 0 | 0 |
| L10I | 690 | 1160 | 1778 | 786 | <0.0001 | 37.3 | 69.3 | 1.9 | 1 | 0 | 0 |
| Q18 | 46 | 1804 | 117 | 2447 | 0.0003 | 2.5 | 4.6 | 1.8 | 1 | 0 | 0 |
| A71V | 608 | 1242 | 1535 | 1029 | <0.0001 | 32.9 | 59.9 | 1.8 | 1 | 0 | 0 |
| M36L | 41 | 1809 | 97 | 2467 | 0.0037 | 2.2 | 3.8 | 1.7 | 0 | 0 | 0 |
| L10 | 1011 | 839 | 2379 | 185 | <0.0001 | 54.6 | 92.8 | 1.7 | 1 | 0 | 0 |
| L23 | 24 | 1826 | 56 | 2508 | 0.0300 | 1.3 | 2.2 | 1.7 | 0 | 0 | 0 |
| A71I | 104 | 1746 | 234 | 2330 | <0.0001 | 5.6 | 9.1 | 1.6 | 1 | 0 | 0 |
| K20 | 587 | 1263 | 1267 | 1297 | <0.0001 | 31.7 | 49.4 | 1.6 | 1 | 0 | 0 |
| I172 | 382 | 1468 | 813 | 1751 | <0.0001 | 20.7 | 31.7 | 1.5 | 1 | 0 | 0 |
| L90 | 843 | 1007 | 1803 | 761 | <0.0001 | 45.6 | 70.3 | 1.5 | 1 | 0 | 0 |
| L90M | 843 | 1007 | 1803 | 761 | <0.0001 | 45.6 | 70.3 | 1.5 | 1 | 0 | 0 |
| K20I | 186 | 1664 | 369 | 2195 | <0.0001 | 10.0 | 14.4 | 1.4 | 1 | 0 | 0 |
| G16 | 101 | 1749 | 197 | 2367 | 0.0035 | 5.5 | 7.7 | 1.4 | 0 | 0 | 0 |
| A71 | 987 | 863 | 1921 | 643 | <0.0001 | 53.4 | 74.9 | 1.4 | 1 | 0 | 0 |
| I62 | 787 | 1063 | 1435 | 1129 | <0.0001 | 42.5 | 56.0 | 1.3 | 1 | 0 | 0 |
| D60 | 229 | 1621 | 412 | 2152 | 0.0006 | 12.4 | 16.1 | 1.3 | 1 | 0 | 0 |
| M36I | 687 | 1163 | 1221 | 1343 | <0.0001 | 37.1 | 47.6 | 1.3 | 1 | 0 | 0 |
| I15 | 386 | 1464 | 670 | 1894 | <0.0001 | 20.9 | 26.1 | 1.2 | 1 | 0 | 0 |
| M36 | 772 | 1078 | 1342 | 1222 | <0.0001 | 41.7 | 52.3 | 1.2 | 1 | 0 | 0 |
| T4 | 1518 | 332 | 2537 | 27 | <0.0001 | 82.0 | 99.0 | 1.2 | 1 | 0 | 0 |
| L19 | 269 | 1581 | 447 | 2117 | 0.0103 | 14.5 | 17.4 | 1.2 | 0 | 0 | 0 |
| I13 | 540 | 1310 | 889 | 1675 | 0.0001 | 29.2 | 34.7 | 1.2 | 1 | 0 | 0 |
| H69 | 188 | 1662 | 308 | 2256 | 0.0596 | 10.2 | 12.0 | 1.2 | 0 | 0 | 0 |
| L63P | 1388 | 462 | 2241 | 323 | <0.0001 | 75.0 | 87.4 | 1.2 | 1 | 0 | 0 |
| E35 | 676 | 1174 | 1065 | 1499 | 0.0008 | 36.5 | 41.5 | 1.1 | 1 | 0 | 0 |
| Q61 | 142 | 1708 | 219 | 2345 | 0.3166 | 7.7 | 8.5 | 1.1 | 0 | 0 | 0 |
| N37 | 690 | 1160 | 1063 | 1501 | 0.0055 | 37.3 | 41.5 | 1.1 | 0 | 0 | 0 |
| M46V | 12 | 1838 | 18 | 2546 | 1.0000 | 0.6 | 0.7 | 1.1 | 0 | 0 | 0 |
| T74S | 173 | 1677 | 259 | 2305 | 0.4121 | 9.4 | 10.1 | 1.1 | 0 | 0 | 0 |
| I93 | 829 | 1021 | 1226 | 1338 | 0.0504 | 44.8 | 47.8 | 1.1 | 0 | 0 | 0 |
| K20M | 119 | 1731 | 175 | 2389 | 0.6249 | 6.4 | 6.8 | 1.1 | 0 | 0 | 0 |
| L10V | 193 | 1657 | 268 | 2296 | 1.0000 | 10.4 | 10.5 | 1.0 | 0 | 0 | 0 |
| R57 | 263 | 1587 | 341 | 2223 | 0.3991 | 14.2 | 13.3 | 0.9 | 0 | 0 | 0 |
| R41 | 526 | 1324 | 686 | 1878 | 0.2188 | 28.4 | 26.8 | 0.9 | 0 | 0 | 0 |
| T12 | 212 | 1638 | 265 | 2299 | 0.2387 | 11.5 | 10.3 | 0.9 | 0 | 0 | 0 |
| K70 | 93 | 1757 | 114 | 2450 | 0.3869 | 5.0 | 4.4 | 0.9 | 0 | 0 | 0 |
| K20T | 128 | 1722 | 153 | 2411 | 0.2116 | 6.9 | 6.0 | 0.9 | 0 | 0 | 0 |
| I64 | 500 | 1350 | 568 | 1996 | 0.0002 | 27.0 | 22.2 | 0.8 | 1 | 0 | 0 |
| V82T | 132 | 1718 | 146 | 2418 | 0.0594 | 7.1 | 5.7 | 0.8 | 0 | 0 | 0 |
| V77 | 775 | 1075 | 786 | 1778 | <0.0001 | 41.9 | 30.7 | 0.7 | 1 | 0 | 0 |
| K14 | 205 | 1645 | 204 | 2360 | 0.0005 | 11.1 | 8.0 | 0.7 | 1 | 0 | 0 |
| L63Q | 45 | 1805 | 42 | 2522 | 0.0629 | 2.4 | 1.6 | 0.7 | 0 | 0 | 0 |
| P39 | 67 | 1783 | 55 | 2509 | 0.0038 | 3.6 | 2.2 | 0.6 | 0 | 0 | 0 |
| L63C | 26 | 1824 | 20 | 2544 | 0.0506 | 1.4 | 0.8 | 0.6 | 0 | 0 | 0 |
| A71T | 384 | 1466 | 300 | 2264 | <0.0001 | 20.8 | 11.7 | 0.6 | 1 | 0 | 0 |
| L63T | 89 | 1761 | 58 | 2506 | <0.0001 | 4.8 | 2.3 | 0.5 | 1 | 0 | 0 |
| K45 | 120 | 1730 | 70 | 2494 | <0.0001 | 6.5 | 2.7 | 0.4 | 1 | 0 | 0 |
| L10R | 21 | 1829 | 11 | 2553 | 0.0106 | 1.1 | 0.4 | 0.4 | 0 | 0 | 0 |
| L63S | 92 | 1758 | 46 | 2518 | <0.0001 | 5.0 | 1.8 | 0.4 | 1 | 0 | 0 |
| L63A | 114 | 1736 | 56 | 2508 | <0.0001 | 6.2 | 2.2 | 0.4 | 1 | 0 | 0 |
| E65D | 41 | 1809 | 19 | 2545 | <0.0001 | 2.2 | 0.7 | 0.3 | 1 | 0 | 1 |
| N88 | 389 | 1461 | 102 | 2462 | <0.0001 | 21.0 | 4.0 | 0.2 | 1 | 0 | 1 |
| D30N | 357 | 1493 | 67 | 2497 | <0.0001 | 19.3 | 2.6 | 0.1 | 1 | 0 | 1 |
| N88S | 91 | 1759 | 4 | 2560 | <0.0001 | 4.9 | 0.2 | 0.03 | 1 | 0 | 1 |

The last 3 columns (P < 0.001, ratio > 3, ratio < 0.3) contain either a "1" if the condition at the top of the column (e.g., P < 0.001) is true and a "0" if the condition is false.

TABLE 3

ANALYSIS OF COMBINATIONS OF PAIRS OF MUTATIONS

| Mutation Pair | PS, mt | PS, wt | PR, mt | PR, wt | P value | % mt S | % mt R | % R/% S | P < 0.001 | Ratio > 3 | Ratio < 0.3 |
|---|---|---|---|---|---|---|---|---|---|---|---|
| L33F-I47V | 0 | 1634 | 7 | 858 | 0.0006 | 0.0% | 0.8% | -N/A- | 1 | 1 | 0 |
| L33F-I54S | 0 | 1634 | 16 | 849 | <0.0001 | 0.0% | 1.8% | -N/A- | 1 | 1 | 0 |
| L33F-V82F | 0 | 1634 | 13 | 852 | <0.0001 | 0.0% | 1.5% | -N/A- | 1 | 1 | 0 |
| L33F-V11 | 0 | 1634 | 24 | 841 | <0.0001 | 0.0% | 2.8% | -N/A- | 1 | 1 | 0 |
| M46I-I54S | 0 | 1634 | 17 | 848 | <0.0001 | 0.0% | 2.0% | -N/A- | 1 | 1 | 0 |
| M46I-I54T | 0 | 1634 | 18 | 847 | <0.0001 | 0.0% | 2.1% | -N/A- | 1 | 1 | 0 |
| M46I-A71L | 0 | 1634 | 10 | 855 | <0.0001 | 0.0% | 1.2% | -N/A- | 1 | 1 | 0 |
| M46I-91 | 0 | 1634 | 10 | 855 | <0.0001 | 0.0% | 1.2% | -N/A- | 1 | 1 | 0 |
| M46L-I54A | 0 | 1634 | 8 | 857 | 0.0002 | 0.0% | 0.9% | -N/A- | 1 | 1 | 0 |

TABLE 3-continued

ANALYSIS OF COMBINATIONS OF PAIRS OF MUTATIONS

| Mutation Pair | PS, mt | PS, wt | PR, mt | PR, wt | P value | % mt S | % mt R | % R/% S | P < 0.001 | Ratio > 3 | Ratio < 0.3 |
|---|---|---|---|---|---|---|---|---|---|---|---|
| M46L-I54S | 0 | 1634 | 9 | 856 | <0.0001 | 0.0% | 1.0% | -N/A- | 1 | 1 | 0 |
| I47V-V11 | 0 | 1634 | 8 | 857 | 0.0002 | 0.0% | 0.9% | -N/A- | 1 | 1 | 0 |
| I47V-K43T | 0 | 1634 | 7 | 858 | 0.0006 | 0.0% | 0.8% | -N/A- | 1 | 1 | 0 |
| I47V-F53L | 0 | 1634 | 16 | 849 | <0.0001 | 0.0% | 1.8% | -N/A- | 1 | 1 | 0 |
| I47V-Q58E | 0 | 1634 | 7 | 858 | 0.0006 | 0.0% | 0.8% | -N/A- | 1 | 1 | 0 |
| G48M-I54V | 0 | 1634 | 17 | 848 | <0.0001 | 0.0% | 2.0% | -N/A- | 1 | 1 | 0 |
| G48M-A71V | 0 | 1634 | 12 | 853 | <0.0001 | 0.0% | 1.4% | -N/A- | 1 | 1 | 0 |
| G48M-L90M | 0 | 1634 | 16 | 849 | <0.0001 | 0.0% | 1.8% | -N/A- | 1 | 1 | 0 |
| G48M-35 | 0 | 1634 | 12 | 853 | <0.0001 | 0.0% | 1.4% | -N/A- | 1 | 1 | 0 |
| G48V-E34Q | 0 | 1634 | 8 | 857 | 0.0002 | 0.0% | 0.9% | -N/A- | 1 | 1 | 0 |
| I54A-K43T | 0 | 1634 | 11 | 854 | <0.0001 | 0.0% | 1.3% | -N/A- | 1 | 1 | 0 |
| I54S-A71L | 0 | 1634 | 7 | 858 | 0.0006 | 0.0% | 0.8% | -N/A- | 1 | 1 | 0 |
| I54S-L90M | 0 | 1634 | 16 | 849 | <0.0001 | 0.0% | 1.8% | -N/A- | 1 | 1 | 0 |
| I54S-M46I | 0 | 1634 | 17 | 848 | <0.0001 | 0.0% | 2.0% | -N/A- | 1 | 1 | 0 |
| I54S-35 | 0 | 1634 | 18 | 847 | <0.0001 | 0.0% | 2.1% | -N/A- | 1 | 1 | 0 |
| I54T-A71L | 0 | 1634 | 7 | 858 | 0.0006 | 0.0% | 0.8% | -N/A- | 1 | 1 | 0 |
| I54T-M46I | 0 | 1634 | 18 | 847 | <0.0001 | 0.0% | 2.1% | -N/A- | 1 | 1 | 0 |
| A71L-A71V | 0 | 1634 | 8 | 857 | 0.0002 | 0.0% | 0.9% | -N/A- | 1 | 1 | 0 |
| A71L-M46I | 0 | 1634 | 10 | 855 | <0.0001 | 0.0% | 1.2% | -N/A- | 1 | 1 | 0 |
| A71V-91 | 0 | 1634 | 13 | 852 | <0.0001 | 0.0% | 1.5% | -N/A- | 1 | 1 | 0 |
| V82F-Q58E | 0 | 1634 | 16 | 849 | <0.0001 | 0.0% | 1.8% | -N/A- | 1 | 1 | 0 |
| V82F-L76V | 0 | 1634 | 8 | 857 | 0.0002 | 0.0% | 0.9% | -N/A- | 1 | 1 | 0 |
| V82S-Q58E | 0 | 1634 | 8 | 857 | 0.0002 | 0.0% | 0.9% | -N/A- | 1 | 1 | 0 |
| V11-K43T | 0 | 1634 | 9 | 856 | <0.0001 | 0.0% | 1.0% | -N/A- | 1 | 1 | 0 |
| V11-F53L | 0 | 1634 | 18 | 847 | <0.0001 | 0.0% | 2.1% | -N/A- | 1 | 1 | 0 |
| V11-Q58E | 0 | 1634 | 7 | 858 | 0.0006 | 0.0% | 0.8% | -N/A- | 1 | 1 | 0 |
| V11-67 | 0 | 1634 | 9 | 856 | <0.0001 | 0.0% | 1.0% | -N/A- | 1 | 1 | 0 |
| K43T-L76V | 0 | 1634 | 9 | 856 | <0.0001 | 0.0% | 1.0% | -N/A- | 1 | 1 | 0 |
| M46I-91 | 0 | 1634 | 10 | 855 | <0.0001 | 0.0% | 1.2% | -N/A- | 1 | 1 | 0 |
| V82A-V11 | 1 | 1633 | 42 | 823 | <0.0001 | 0.1% | 4.9% | 79.3 | 1 | 1 | 0 |
| I54V-V11 | 1 | 1633 | 38 | 827 | <0.0001 | 0.1% | 4.4% | 71.8 | 1 | 1 | 0 |
| L10I-L76V | 1 | 1633 | 31 | 834 | <0.0001 | 0.1% | 3.6% | 58.6 | 1 | 1 | 0 |
| L33F-K43T | 2 | 1632 | 49 | 816 | <0.0001 | 0.1% | 5.7% | 46.3 | 1 | 1 | 0 |
| I54A-L90M | 1 | 1633 | 24 | 841 | <0.0001 | 0.1% | 2.8% | 45.3 | 1 | 1 | 0 |
| L10I-G48M | 1 | 1633 | 22 | 843 | <0.0001 | 0.1% | 2.5% | 41.6 | 1 | 1 | 0 |
| I54S-V82A | 2 | 1632 | 39 | 826 | <0.0001 | 0.1% | 4.5% | 36.8 | 1 | 1 | 0 |
| L10I-I54S | 2 | 1632 | 38 | 827 | <0.0001 | 0.1% | 4.4% | 35.9 | 1 | 1 | 0 |
| M46I-I47V | 1 | 1633 | 19 | 846 | <0.0001 | 0.1% | 2.2% | 35.9 | 1 | 1 | 0 |
| I47V-M46I | 1 | 1633 | 19 | 846 | <0.0001 | 0.1% | 2.2% | 35.9 | 1 | 1 | 0 |
| G48M-V82A | 1 | 1633 | 18 | 847 | <0.0001 | 0.1% | 2.1% | 34.0 | 1 | 1 | 0 |
| I54T-L90M | 1 | 1633 | 18 | 847 | <0.0001 | 0.1% | 2.1% | 34.0 | 1 | 1 | 0 |
| G48V-I54S | 2 | 1632 | 35 | 830 | <0.0001 | 0.1% | 4.0% | 33.0 | 1 | 1 | 0 |
| I47V-L90M | 1 | 1633 | 17 | 848 | <0.0001 | 0.1% | 2.0% | 32.1 | 1 | 1 | 0 |
| I54S-A71V | 2 | 1632 | 34 | 831 | <0.0001 | 0.1% | 3.9% | 32.1 | 1 | 1 | 0 |
| L33F-G73 | 4 | 1630 | 64 | 801 | <0.0001 | 0.2% | 7.4% | 30.2 | 1 | 1 | 0 |
| M46L-I54T | 1 | 1633 | 16 | 849 | <0.0001 | 0.1% | 1.8% | 30.2 | 1 | 1 | 0 |
| L76V-35 | 2 | 1632 | 31 | 834 | <0.0001 | 0.1% | 3.6% | 29.3 | 1 | 1 | 0 |
| L10I-A71L | 1 | 1633 | 15 | 850 | <0.0001 | 0.1% | 1.7% | 28.3 | 1 | 1 | 0 |
| G48M-F53L | 1 | 1633 | 15 | 850 | <0.0001 | 0.1% | 1.7% | 28.3 | 1 | 1 | 0 |
| L33F-I54T | 1 | 1633 | 14 | 851 | <0.0001 | 0.1% | 1.6% | 26.4 | 1 | 1 | 0 |
| G48V-K43T | 2 | 1632 | 28 | 837 | <0.0001 | 0.1% | 3.2% | 26.4 | 1 | 1 | 0 |
| L90M-91 | 1 | 1633 | 14 | 851 | <0.0001 | 0.1% | 1.6% | 26.4 | 1 | 1 | 0 |
| A71V-V82F | 3 | 1631 | 41 | 824 | <0.0001 | 0.2% | 4.7% | 25.8 | 1 | 1 | 0 |
| L90M-L76V | 2 | 1632 | 27 | 838 | <0.0001 | 0.1% | 3.1% | 25.5 | 1 | 1 | 0 |
| L33F-F53L | 4 | 1630 | 52 | 813 | <0.0001 | 0.2% | 6.0% | 24.6 | 1 | 1 | 1 |
| M46L-V1I | 1 | 1633 | 13 | 852 | <0.0001 | 0.1% | 1.5% | 24.6 | 1 | 1 | 0 |
| L33F-L24I | 3 | 1631 | 39 | 826 | <0.0001 | 0.2% | 4.5% | 24.6 | 1 | 1 | 0 |
| M46I-G48V | 2 | 1632 | 25 | 840 | <0.0001 | 0.1% | 2.9% | 23.6 | 1 | 1 | 0 |
| G48V-M46I | 2 | 1632 | 25 | 840 | <0.0001 | 0.1% | 2.9% | 23.6 | 1 | 1 | 0 |
| Q58E-G73 | 3 | 1631 | 37 | 828 | <0.0001 | 0.2% | 4.3% | 23.3 | 1 | 1 | 0 |
| L33F-L76V | 1 | 1633 | 12 | 853 | <0.0001 | 0.1% | 1.4% | 22.7 | 1 | 1 | 0 |
| I54T-A71V | 3 | 1631 | 36 | 829 | <0.0001 | 0.2% | 4.2% | 22.7 | 1 | 1 | 0 |
| A71L-V82A | 1 | 1633 | 12 | 853 | <0.0001 | 0.1% | 1.4% | 22.7 | 1 | 1 | 0 |
| V82F-F53L | 1 | 1633 | 12 | 853 | <0.0001 | 0.1% | 1.4% | 22.7 | 1 | 1 | 0 |
| V11-G73 | 2 | 1632 | 24 | 841 | <0.0001 | 0.1% | 2.8% | 22.7 | 1 | 1 | 0 |
| L24I-G73 | 2 | 1632 | 24 | 841 | <0.0001 | 0.1% | 2.8% | 22.7 | 1 | 1 | 0 |
| L10F-67 | 1 | 1633 | 11 | 854 | <0.0001 | 0.1% | 1.3% | 20.8 | 1 | 1 | 0 |
| L33F-M46L | 7 | 1627 | 77 | 788 | <0.0001 | 0.4% | 8.9% | 20.8 | 1 | 1 | 0 |
| L33F-I54A | 1 | 1633 | 11 | 854 | <0.0001 | 0.1% | 1.3% | 20.8 | 1 | 1 | 0 |
| V82A-91 | 2 | 1632 | 22 | 843 | <0.0001 | 0.1% | 2.5% | 20.8 | 1 | 1 | 0 |
| L24I-Q58E | 2 | 1632 | 22 | 843 | <0.0001 | 0.1% | 2.5% | 20.8 | 1 | 1 | 0 |
| Q58E-L76V | 1 | 1633 | 11 | 854 | <0.0001 | 0.1% | 1.3% | 20.8 | 1 | 1 | 0 |
| M46I-V82F | 4 | 1630 | 43 | 822 | <0.0001 | 0.2% | 5.0% | 20.3 | 1 | 1 | 0 |
| V82F-M46I | 4 | 1630 | 43 | 822 | <0.0001 | 0.2% | 5.0% | 20.3 | 1 | 1 | 0 |
| I54V-L76V | 3 | 1631 | 32 | 833 | <0.0001 | 0.2% | 3.7% | 20.1 | 1 | 1 | 0 |
| L10F-V82S | 1 | 1633 | 10 | 855 | 0.0002 | 0.1% | 1.2% | 18.9 | 1 | 1 | 0 |

TABLE 3-continued

ANALYSIS OF COMBINATIONS OF PAIRS OF MUTATIONS

| Mutation Pair | PS, mt | PS, wt | PR, mt | PR, wt | P value | % mt S | % mt R | % R/% S | P < 0.001 | Ratio > 3 | Ratio < 0.3 |
|---|---|---|---|---|---|---|---|---|---|---|---|
| I54S-I54T | 1 | 1633 | 10 | 855 | 0.0002 | 0.1% | 1.2% | 18.9 | 1 | 1 | 0 |
| L33F-M46I | 5 | 1629 | 50 | 815 | <0.0001 | 0.3% | 5.8% | 18.9 | 1 | 1 | 0 |
| L33F-M46I | 5 | 1629 | 50 | 815 | <0.0001 | 0.3% | 5.8% | 18.9 | 1 | 1 | 0 |
| M46I-V11 | 2 | 1632 | 19 | 846 | <0.0001 | 0.1% | 2.2% | 17.9 | 1 | 1 | 0 |
| V82F-L90M | 6 | 1628 | 57 | 808 | <0.0001 | 0.4% | 6.6% | 17.9 | 1 | 1 | 0 |
| V11-M46I | 2 | 1632 | 19 | 846 | <0.0001 | 0.1% | 2.2% | 17.9 | 1 | 1 | 0 |
| L10F-L76V | 1 | 1633 | 9 | 856 | 0.0005 | 0.1% | 1.0% | 17.0 | 1 | 1 | 0 |
| L33F-91 | 1 | 1633 | 9 | 856 | 0.0005 | 0.1% | 1.0% | 17.0 | 1 | 1 | 0 |
| I47V-I54V | 2 | 1632 | 18 | 847 | <0.0001 | 0.1% | 2.1% | 17.0 | 1 | 1 | 0 |
| L33F-V82A | 18 | 1616 | 162 | 703 | <0.0001 | 1.1% | 18.7% | 17.0 | 1 | 1 | 0 |
| M46L-K43T | 5 | 1629 | 45 | 820 | <0.0001 | 0.3% | 5.2% | 17.0 | 1 | 1 | 0 |
| I54V-V82F | 6 | 1628 | 54 | 811 | <0.0001 | 0.4% | 6.2% | 17.0 | 1 | 1 | 0 |
| V11-35 | 3 | 1631 | 27 | 838 | <0.0001 | 0.2% | 3.1% | 17.0 | 1 | 1 | 0 |
| L33F-G48V | 4 | 1630 | 35 | 830 | <0.0001 | 0.2% | 4.0% | 16.5 | 1 | 1 | 0 |
| A71V-L76V | 3 | 1631 | 26 | 839 | <0.0001 | 0.2% | 3.0% | 16.4 | 1 | 1 | 0 |
| I47V-V82A | 2 | 1632 | 17 | 848 | <0.0001 | 0.1% | 2.0% | 16.1 | 1 | 1 | 0 |
| L10I-91 | 2 | 1632 | 16 | 849 | <0.0001 | 0.1% | 1.8% | 15.1 | 1 | 1 | 0 |
| L33F-A71V | 16 | 1618 | 120 | 745 | <0.0001 | 1.0% | 13.9% | 14.2 | 1 | 1 | 0 |
| I47V-A71V | 2 | 1632 | 15 | 850 | <0.0001 | 0.1% | 1.7% | 14.2 | 1 | 1 | 0 |
| K43T-F53L | 4 | 1630 | 30 | 835 | <0.0001 | 0.2% | 3.5% | 14.2 | 1 | 1 | 0 |
| F53L-Q58E | 2 | 1632 | 15 | 850 | <0.0001 | 0.1% | 1.7% | 14.2 | 1 | 1 | 0 |
| L10I-L33F | 19 | 1615 | 142 | 723 | <0.0001 | 1.2% | 16.4% | 14.1 | 1 | 1 | 0 |
| L10I-V11 | 5 | 1629 | 37 | 828 | <0.0001 | 0.3% | 4.3% | 14.0 | 1 | 1 | 0 |
| I54V-91 | 3 | 1631 | 22 | 843 | <0.0001 | 0.2% | 2.5% | 13.9 | 1 | 1 | 0 |
| V82S-K43T | 2 | 1632 | 14 | 851 | <0.0001 | 0.1% | 1.6% | 13.2 | 1 | 1 | 0 |
| L33F-Q58E | 6 | 1628 | 42 | 823 | <0.0001 | 0.4% | 4.9% | 13.2 | 1 | 1 | 0 |
| L90M-V11 | 6 | 1628 | 42 | 823 | <0.0001 | 0.4% | 4.9% | 13.2 | 1 | 1 | 0 |
| L33F-I54V | 22 | 1612 | 149 | 716 | <0.0001 | 1.3% | 17.2% | 12.8 | 1 | 1 | 0 |
| A71V-V11 | 6 | 1628 | 40 | 825 | <0.0001 | 0.4% | 4.6% | 12.6 | 1 | 1 | 0 |
| L10I-V82F | 10 | 1624 | 66 | 799 | <0.0001 | 0.6% | 7.6% | 12.5 | 1 | 1 | 0 |
| I54A-V82A | 5 | 1629 | 32 | 833 | < 0.0001 | 0.3% | 3.7% | 12.1 | 1 | 1 | 0 |
| L24I-F53L | 5 | 1629 | 32 | 833 | <0.0001 | 0.3% | 3.7% | 12.1 | 1 | 1 | 0 |
| M46L-G48V | 8 | 1626 | 50 | 815 | <0.0001 | 0.5% | 5.8% | 11.8 | 1 | 1 | 0 |
| M46L-Q58E | 8 | 1626 | 50 | 815 | <0.0001 | 0.5% | 5.8% | 11.8 | 1 | 1 | 0 |
| M46I-L76V | 7 | 1627 | 43 | 822 | <0.0001 | 0.4% | 5.0% | 11.6 | 1 | 1 | 0 |
| M46I-L76V | 7 | 1627 | 43 | 822 | <0.0001 | 0.4% | 5.0% | 11.6 | 1 | 1 | 0 |
| M46I-I54A | 2 | 1632 | 12 | 853 | 0.0001 | 0.1% | 1.4% | 11.3 | 1 | 1 | 0 |
| M46L-V82F | 2 | 1632 | 12 | 853 | 0.0001 | 0.1% | 1.4% | 11.3 | 1 | 1 | 0 |
| I54A-M46I | 2 | 1632 | 12 | 853 | 0.0001 | 0.1% | 1.4% | 11.3 | 1 | 1 | 0 |
| V82S-L24I | 3 | 1631 | 18 | 847 | <0.0001 | 0.2% | 2.1% | 11.3 | 1 | 1 | 0 |
| L10F-G73 | 5 | 1629 | 29 | 836 | <0.0001 | 0.3% | 3.4% | 11.0 | 1 | 1 | 0 |
| L10I-I47V | 4 | 1630 | 23 | 842 | <0.0001 | 0.2% | 2.7% | 10.9 | 1 | 1 | 0 |
| V82A-L76V | 4 | 1630 | 23 | 842 | <0.0001 | 0.2% | 2.7% | 10.9 | 1 | 1 | 0 |
| K43T-G73 | 3 | 1631 | 17 | 848 | <0.0001 | 0.2% | 2.0% | 10.7 | 1 | 1 | 0 |
| L33F-V82S | 2 | 1632 | 11 | 854 | 0.0003 | 0.1% | 1.3% | 10.4 | 1 | 1 | 0 |
| I47V-35 | 2 | 1632 | 11 | 854 | 0.0003 | 0.1% | 1.3% | 10.4 | 1 | 1 | 0 |
| G48V-I54A | 2 | 1632 | 11 | 854 | 0.0003 | 0.1% | 1.3% | 10.4 | 1 | 1 | 0 |
| G48V-G73 | 2 | 1632 | 11 | 854 | 0.0003 | 0.1% | 1.3% | 10.4 | 1 | 1 | 0 |
| E34Q-F53L | 2 | 1632 | 11 | 854 | 0.0003 | 0.1% | 1.3% | 10.4 | 1 | 1 | 0 |
| Q58E-67 | 2 | 1632 | 11 | 854 | 0.0003 | 0.1% | 1.3% | 10.4 | 1 | 1 | 0 |
| L33F-35 | 20 | 1614 | 107 | 758 | <0.0001 | 1.2% | 12.4% | 10.1 | 1 | 1 | 0 |
| L10I-I54A | 7 | 1627 | 37 | 828 | <0.0001 | 0.4% | 4.3% | 10.0 | 1 | 1 | 0 |
| L10I-I54T | 8 | 1626 | 41 | 824 | <0.0001 | 0.5% | 4.7% | 9.7 | 1 | 1 | 0 |
| G48V-I54T | 8 | 1626 | 41 | 824 | <0.0001 | 0.5% | 4.7% | 9.7 | 1 | 1 | 0 |
| K43T-35 | 16 | 1618 | 82 | 783 | <0.0001 | 1.0% | 9.5% | 9.7 | 1 | 1 | 0 |
| V82A-Q58E | 20 | 1614 | 101 | 764 | <0.0001 | 1.2% | 11.7% | 9.5 | 1 | 1 | 0 |
| L33F-L90M | 25 | 1609 | 125 | 740 | <0.0001 | 1.5% | 14.5% | 9.4 | 1 | 1 | 0 |
| I54T-V82A | 9 | 1625 | 45 | 820 | <0.0001 | 0.6% | 5.2% | 9.4 | 1 | 1 | 0 |
| V82S-G73 | 2 | 1632 | 10 | 855 | 0.0007 | 0.1% | 1.2% | 9.4 | 1 | 1 | 0 |
| L24I-K43T | 6 | 1628 | 30 | 835 | <0.0001 | 0.4% | 3.5% | 9.4 | 1 | 1 | 0 |
| I54A-A71V | 6 | 1628 | 29 | 836 | <0.0001 | 0.4% | 3.4% | 9.1 | 1 | 1 | 0 |
| V82A-K43T | 22 | 1612 | 106 | 759 | <0.0001 | 1.3% | 12.3% | 9.1 | 1 | 1 | 0 |
| V82F-35 | 8 | 1626 | 37 | 828 | <0.0001 | 0.5% | 4.3% | 8.7 | 1 | 1 | 0 |
| L90M-K43T | 15 | 1619 | 67 | 798 | <0.0001 | 0.9% | 7.7% | 8.4 | 1 | 1 | 0 |
| I54V-K43T | 24 | 1610 | 104 | 761 | <0.0001 | 1.5% | 12.0% | 8.2 | 1 | 1 | 0 |
| V82A-V82S | 4 | 1630 | 17 | 848 | <0.0001 | 0.2% | 2.0% | 8.0 | 1 | 1 | 0 |
| L10F-L33F | 9 | 1625 | 36 | 829 | <0.0001 | 0.6% | 4.2% | 7.6 | 1 | 1 | 0 |
| L10F-Q58E | 5 | 1629 | 19 | 846 | <0.0001 | 0.3% | 2.2% | 7.2 | 1 | 1 | 0 |
| M46L-F53L | 8 | 1626 | 30 | 835 | <0.0001 | 0.5% | 3.5% | 7.1 | 1 | 1 | 0 |
| I54A-35 | 4 | 1630 | 15 | 850 | <0.0001 | 0.2% | 1.7% | 7.1 | 1 | 1 | 0 |
| M46I-K43T | 11 | 1623 | 41 | 824 | <0.0001 | 0.7% | 4.7% | 7.0 | 1 | 1 | 0 |
| K43T-M46I | 11 | 1623 | 41 | 824 | <0.0001 | 0.7% | 4.7% | 7.0 | 1 | 1 | 0 |
| F53L-G73 | 12 | 1622 | 44 | 821 | <0.0001 | 0.7% | 5.1% | 6.9 | 1 | 1 | 0 |
| L10I-K43T | 25 | 1609 | 91 | 774 | <0.0001 | 1.5% | 10.5% | 6.9 | 1 | 1 | 0 |
| L10F-L24I | 8 | 1626 | 29 | 836 | <0.0001 | 0.5% | 3.4% | 6.9 | 1 | 1 | 0 |
| A71V-Q58E | 22 | 1612 | 78 | 787 | <0.0001 | 1.3% | 9.0% | 6.7 | 1 | 1 | 0 |

TABLE 3-continued

ANALYSIS OF COMBINATIONS OF PAIRS OF MUTATIONS

| Mutation Pair | PS, mt | PS, wt | PR, mt | PR, wt | P value | % mt S | % mt R | % R/% S | P < 0.001 | Ratio > 3 | Ratio < 0.3 |
|---|---|---|---|---|---|---|---|---|---|---|---|
| A71V-K43T | 20 | 1614 | 70 | 795 | <0.0001 | 1.2% | 8.1% | 6.6 | 1 | 1 | 0 |
| I54V-Q58E | 31 | 1603 | 106 | 759 | <0.0001 | 1.9% | 12.3% | 6.5 | 1 | 1 | 0 |
| L10F-F53L | 5 | 1629 | 17 | 848 | <0.0001 | 0.3% | 2.0% | 6.4 | 1 | 1 | 0 |
| L90M-E34Q | 6 | 1628 | 20 | 845 | <0.0001 | 0.4% | 2.3% | 6.3 | 1 | 1 | 0 |
| L10I-Q58E | 32 | 1602 | 105 | 760 | <0.0001 | 2.0% | 12.1% | 6.2 | 1 | 1 | 0 |
| G48V-A71V | 27 | 1607 | 88 | 777 | <0.0001 | 1.7% | 10.2% | 6.2 | 1 | 1 | 0 |
| M46I-F53L | 17 | 1617 | 55 | 810 | <0.0001 | 1.0% | 6.4% | 6.1 | 1 | 1 | 0 |
| M46I-F53L | 17 | 1617 | 55 | 810 | <0.0001 | 1.0% | 6.4% | 6.1 | 1 | 1 | 0 |
| V82A-G73 | 35 | 1599 | 113 | 752 | <0.0001 | 2.1% | 13.1% | 6.1 | 1 | 1 | 0 |
| L10F-K43T | 6 | 1628 | 19 | 846 | <0.0001 | 0.4% | 2.2% | 6.0 | 1 | 1 | 0 |
| F53L-35 | 20 | 1614 | 63 | 802 | <0.0001 | 1.2% | 7.3% | 6.0 | 1 | 1 | 0 |
| V82S-35 | 7 | 1627 | 22 | 843 | <0.0001 | 0.4% | 2.5% | 5.9 | 1 | 1 | 0 |
| M46I-Q58E | 18 | 1616 | 56 | 809 | <0.0001 | 1.1% | 6.5% | 5.9 | 1 | 1 | 0 |
| M46I-Q58E | 18 | 1616 | 56 | 809 | <0.0001 | 1.1% | 6.5% | 5.9 | 1 | 1 | 0 |
| V82A-F53L | 34 | 1600 | 105 | 760 | <0.0001 | 2.1% | 12.1% | 5.8 | 1 | 1 | 0 |
| A71V-V82S | 12 | 1622 | 37 | 828 | <0.0001 | 0.7% | 4.3% | 5.8 | 1 | 1 | 0 |
| M46L-L24I | 19 | 1615 | 58 | 807 | <0.0001 | 1.2% | 6.7% | 5.8 | 1 | 1 | 0 |
| I54V-G73 | 44 | 1590 | 133 | 732 | <0.0001 | 2.7% | 15.4% | 5.7 | 1 | 1 | 0 |
| G48V-Q58E | 7 | 1627 | 21 | 844 | <0.0001 | 0.4% | 2.4% | 5.7 | 1 | 1 | 0 |
| I54V-F53L | 41 | 1593 | 120 | 745 | <0.0001 | 2.5% | 13.9% | 5.5 | 1 | 1 | 0 |
| I54V-V82S | 16 | 1618 | 45 | 820 | <0.0001 | 1.0% | 5.2% | 5.3 | 1 | 1 | 0 |
| V82S-L90M | 9 | 1625 | 25 | 840 | <0.0001 | 0.6% | 2.9% | 5.2 | 1 | 1 | 0 |
| V82A-67 | 7 | 1627 | 19 | 846 | <0.0001 | 0.4% | 2.2% | 5.1 | 1 | 1 | 0 |
| L10I-V82S | 13 | 1621 | 35 | 830 | <0.0001 | 0.8% | 4.0% | 5.1 | 1 | 1 | 0 |
| M46L-I54V | 63 | 1571 | 169 | 696 | <0.0001 | 3.9% | 19.5% | 5.1 | 1 | 1 | 0 |
| V82A-L24I | 43 | 1591 | 115 | 750 | <0.0001 | 2.6% | 13.3% | 5.1 | 1 | 1 | 0 |
| V82A-E34Q | 8 | 1626 | 21 | 844 | <0.0001 | 0.5% | 2.4% | 5.0 | 1 | 1 | 0 |
| L10I-M46L | 64 | 1570 | 165 | 700 | <0.0001 | 3.9% | 19.1% | 4.9 | 1 | 1 | 0 |
| L10F-M46L | 13 | 1621 | 33 | 832 | <0.0001 | 0.8% | 3.8% | 4.8 | 1 | 1 | 0 |
| M46L-L90M | 54 | 1580 | 137 | 728 | <0.0001 | 3.3% | 15.8% | 4.8 | 1 | 1 | 0 |
| G48V-V82A | 54 | 1580 | 137 | 728 | <0.0001 | 3.3% | 15.8% | 4.8 | 1 | 1 | 0 |
| L10I-L24I | 49 | 1585 | 123 | 742 | <0.0001 | 3.0% | 14.2% | 4.7 | 1 | 1 | 0 |
| G48V-35 | 20 | 1614 | 50 | 815 | <0.0001 | 1.2% | 5.8% | 4.7 | 1 | 1 | 0 |
| L24I-35 | 28 | 1606 | 69 | 796 | <0.0001 | 1.7% | 8.0% | 4.7 | 1 | 1 | 0 |
| L90M-Q58E | 41 | 1593 | 101 | 764 | <0.0001 | 2.5% | 11.7% | 4.7 | 1 | 1 | 0 |
| I54V-L24I | 49 | 1585 | 120 | 745 | <0.0001 | 3.0% | 13.9% | 4.6 | 1 | 1 | 0 |
| A71V-E34Q | 9 | 1625 | 22 | 843 | <0.0001 | 0.6% | 2.5% | 4.6 | 1 | 1 | 0 |
| M46L-A71V | 58 | 1576 | 141 | 724 | <0.0001 | 3.5% | 16.3% | 4.6 | 1 | 1 | 0 |
| L10I-F53L | 43 | 1591 | 103 | 762 | <0.0001 | 2.6% | 11.9% | 4.5 | 1 | 1 | 0 |
| M46L-G73 | 16 | 1618 | 38 | 827 | <0.0001 | 1.0% | 4.4% | 4.5 | 1 | 1 | 0 |
| L10F-I54V | 35 | 1599 | 83 | 782 | <0.0001 | 2.1% | 9.6% | 4.5 | 1 | 1 | 0 |
| M46L-V82A | 81 | 1553 | 190 | 675 | <0.0001 | 5.0% | 22.0% | 4.4 | 1 | 1 | 0 |
| L10I-E34Q | 9 | 1625 | 21 | 844 | 0.0001 | 0.6% | 2.4% | 4.4 | 1 | 1 | 0 |
| L10I-G48V | 56 | 1578 | 126 | 739 | <0.0001 | 3.4% | 14.6% | 4.3 | 1 | 1 | 0 |
| L10F-V82A | 31 | 1603 | 69 | 796 | <0.0001 | 1.9% | 8.0% | 4.2 | 1 | 1 | 0 |
| M46L-35 | 43 | 1591 | 95 | 770 | <0.0001 | 2.6% | 11.0% | 4.2 | 1 | 1 | 0 |
| M46I-V82A | 78 | 1556 | 172 | 693 | <0.0001 | 4.8% | 19.9% | 4.2 | 1 | 1 | 0 |
| V82A-M46I | 78 | 1556 | 172 | 693 | <0.0001 | 4.8% | 19.9% | 4.2 | 1 | 1 | 0 |
| A71V-V82A | 154 | 1480 | 339 | 526 | <0.0001 | 9.4% | 39.2% | 4.2 | 1 | 1 | 0 |
| Q58E-35 | 30 | 1604 | 66 | 799 | <0.0001 | 1.8% | 7.6% | 4.2 | 1 | 1 | 0 |
| A71V-F53L | 40 | 1594 | 88 | 777 | <0.0001 | 2.4% | 10.2% | 4.2 | 1 | 1 | 0 |
| L90M-F53L | 43 | 1591 | 94 | 771 | <0.0001 | 2.6% | 10.9% | 4.1 | 1 | 1 | 0 |
| A71V-L24I | 35 | 1599 | 74 | 791 | <0.0001 | 2.1% | 8.6% | 4.0 | 1 | 1 | 0 |
| I54V-L90M | 180 | 1454 | 354 | 511 | <0.0001 | 11.0% | 40.9% | 3.7 | 1 | 1 | 0 |
| I54V-35 | 136 | 1498 | 263 | 602 | <0.0001 | 8.3% | 30.4% | 3.7 | 1 | 1 | 0 |
| V82A-L90M | 159 | 1475 | 305 | 560 | <0.0001 | 9.7% | 35.3% | 3.6 | 1 | 1 | 0 |
| M46I-I54V | 99 | 1535 | 189 | 676 | <0.0001 | 6.1% | 21.8% | 3.6 | 1 | 1 | 0 |
| I54V-M46I | 99 | 1535 | 189 | 676 | <0.0001 | 6.1% | 21.8% | 3.6 | 1 | 1 | 0 |
| V82A-35 | 117 | 1517 | 223 | 642 | <0.0001 | 7.2% | 25.8% | 3.6 | 1 | 1 | 0 |
| G48V-L90M | 35 | 1599 | 65 | 800 | <0.0001 | 2.1% | 7.5% | 3.5 | 1 | 1 | 0 |
| L10I-V82A | 229 | 1405 | 424 | 441 | <0.0001 | 14.0% | 49.0% | 3.5 | 1 | 1 | 0 |
| I54V-A71V | 190 | 1444 | 339 | 526 | <0.0001 | 11.6% | 39.2% | 3.4 | 1 | 1 | 0 |
| L10F-A71V | 34 | 1600 | 60 | 805 | <0.0001 | 2.1% | 6.9% | 3.3 | 1 | 1 | 0 |
| L10I-M46I | 143 | 1491 | 252 | 613 | <0.0001 | 8.8% | 29.1% | 3.3 | 1 | 1 | 0 |
| L10I-M46I | 143 | 1491 | 252 | 613 | <0.0001 | 8.8% | 29.1% | 3.3 | 1 | 1 | 0 |
| L10F-L90M | 45 | 1589 | 78 | 787 | <0.0001 | 2.8% | 9.0% | 3.3 | 1 | 1 | 0 |
| M46I-G73 | 64 | 1570 | 107 | 758 | <0.0001 | 3.9% | 12.4% | 3.2 | 1 | 1 | 0 |
| M46I-G73 | 64 | 1570 | 107 | 758 | <0.0001 | 3.9% | 12.4% | 3.2 | 1 | 1 | 0 |
| L10I-I54V | 243 | 1391 | 403 | 462 | <0.0001 | 14.9% | 46.6% | 3.1 | 1 | 1 | 0 |
| I54V-V82A | 246 | 1388 | 406 | 459 | <0.0001 | 15.1% | 46.9% | 3.1 | 1 | 1 | 0 |
| I54V-67 | 20 | 1614 | 33 | 832 | <0.0001 | 1.2% | 3.8% | 3.1 | 1 | 1 | 0 |
| M46I-L24I | 44 | 1590 | 72 | 793 | <0.0001 | 2.7% | 8.3% | 3.1 | 1 | 1 | 0 |
| L24I-M46I | 44 | 1590 | 72 | 793 | <0.0001 | 2.7% | 8.3% | 3.1 | 1 | 1 | 0 |
| L10I-L10F | 18 | 1616 | 29 | 836 | 0.0001 | 1.1% | 3.4% | 3.0 | 1 | 0 | 0 |
| L10I-A71V | 221 | 1413 | 355 | 510 | <0.0001 | 13.5% | 41.0% | 3.0 | 1 | 0 | 0 |
| L10I-G73 | 99 | 1535 | 155 | 710 | <0.0001 | 6.1% | 17.9% | 3.0 | 1 | 0 | 0 |

TABLE 3-continued

ANALYSIS OF COMBINATIONS OF PAIRS OF MUTATIONS

| Mutation Pair | PS, mt | PS, wt | PR, mt | PR, wt | P value | % mt S | % mt R | % R/% S | P < 0.001 | Ratio > 3 | Ratio < 0.3 |
|---|---|---|---|---|---|---|---|---|---|---|---|
| L10F-M46I | 31 | 1603 | 48 | 817 | <0.0001 | 1.9% | 5.5% | 2.9 | 1 | 0 | 0 |
| L10F-M46I | 31 | 1603 | 48 | 817 | <0.0001 | 1.9% | 5.5% | 2.9 | 1 | 0 | 0 |
| G73-35 | 57 | 1577 | 86 | 779 | <0.0001 | 3.5% | 9.9% | 2.9 | 1 | 0 | 0 |
| M46I-A71V | 113 | 1521 | 169 | 696 | <0.0001 | 6.9% | 19.5% | 2.8 | 1 | 0 | 0 |
| A71V-M46I | 113 | 1521 | 169 | 696 | <0.0001 | 6.9% | 19.5% | 2.8 | 1 | 0 | 0 |
| M46I-35 | 89 | 1545 | 126 | 739 | <0.0001 | 5.4% | 14.6% | 2.7 | 1 | 0 | 0 |
| M46I-35 | 89 | 1545 | 126 | 739 | <0.0001 | 5.4% | 14.6% | 2.7 | 1 | 0 | 0 |
| G48V-I54V | 41 | 1593 | 57 | 808 | <0.0001 | 2.5% | 6.6% | 2.6 | 1 | 0 | 0 |
| L10I-35 | 198 | 1436 | 265 | 600 | <0.0001 | 12.1% | 30.6% | 2.5 | 1 | 0 | 0 |
| A71V-G73 | 101 | 1533 | 129 | 736 | <0.0001 | 6.2% | 14.9% | 2.4 | 1 | 0 | 0 |
| L90M-67 | 30 | 1604 | 36 | 829 | 0.0009 | 1.8% | 4.2% | 2.3 | 1 | 0 | 0 |
| A71V-L90M | 282 | 1352 | 324 | 541 | <0.0001 | 17.3% | 37.5% | 2.2 | 1 | 0 | 0 |
| L10I-L90M | 328 | 1306 | 376 | 489 | <0.0001 | 20.1% | 43.5% | 2.2 | 1 | 0 | 0 |
| M46I-L90M | 187 | 1447 | 213 | 652 | <0.0001 | 11.4% | 24.6% | 2.2 | 1 | 0 | 0 |
| L90M-M46I | 187 | 1447 | 213 | 652 | <0.0001 | 11.4% | 24.6% | 2.2 | 1 | 0 | 0 |
| L90M-G73 | 154 | 1480 | 174 | 691 | <0.0001 | 9.4% | 20.1% | 2.1 | 1 | 0 | 0 |
| A71V-35 | 204 | 1430 | 208 | 657 | <0.0001 | 12.5% | 24.0% | 1.9 | 1 | 0 | 0 |
| L90M-35 | 254 | 1380 | 246 | 619 | <0.0001 | 15.5% | 28.4% | 1.8 | 1 | 0 | 0 |
| M46I-M46I | 358 | 1276 | 342 | 523 | <0.0001 | 21.9% | 39.5% | 1.8 | 1 | 0 | 0 |
| L33F-G48M | 0 | 1634 | 6 | 859 | 0.0017 | 0.0% | 0.7% | -N/A- | 0 | 1 | 0 |
| M46L-91 | 0 | 1634 | 5 | 860 | 0.0049 | 0.0% | 0.6% | -N/A- | 0 | 1 | 0 |
| I47V-V82F | 0 | 1634 | 5 | 860 | 0.0049 | 0.0% | 0.6% | -N/A- | 0 | 1 | 0 |
| G48M-G48V | 0 | 1634 | 5 | 860 | 0.0049 | 0.0% | 0.6% | -N/A- | 0 | 1 | 0 |
| G48M-V82S | 0 | 1634 | 6 | 859 | 0.0017 | 0.0% | 0.7% | -N/A- | 0 | 1 | 0 |
| G48M-G73 | 0 | 1634 | 5 | 860 | 0.0049 | 0.0% | 0.6% | -N/A- | 0 | 1 | 0 |
| I54S-E34Q | 0 | 1634 | 5 | 860 | 0.0049 | 0.0% | 0.6% | -N/A- | 0 | 1 | 0 |
| I54S-K43T | 0 | 1634 | 6 | 859 | 0.0017 | 0.0% | 0.7% | -N/A- | 0 | 1 | 0 |
| I54T-V11 | 0 | 1634 | 5 | 860 | 0.0049 | 0.0% | 0.6% | -N/A- | 0 | 1 | 0 |
| I54T-K43T | 0 | 1634 | 6 | 859 | 0.0017 | 0.0% | 0.7% | -N/A- | 0 | 1 | 0 |
| I54T-Q58E | 0 | 1634 | 6 | 859 | 0.0017 | 0.0% | 0.7% | -N/A- | 0 | 1 | 0 |
| L24I-91 | 0 | 1634 | 6 | 859 | 0.0017 | 0.0% | 0.7% | -N/A- | 0 | 1 | 0 |
| K43T-Q58E | 0 | 1634 | 5 | 860 | 0.0049 | 0.0% | 0.6% | -N/A- | 0 | 1 | 0 |
| Q58E-91 | 0 | 1634 | 6 | 859 | 0.0017 | 0.0% | 0.7% | -N/A- | 0 | 1 | 0 |
| L10F-V11 | 1 | 1633 | 8 | 857 | 0.0013 | 0.1% | 0.9% | 15.1 | 0 | 1 | 0 |
| M46I-E34Q | 1 | 1633 | 8 | 857 | 0.0013 | 0.1% | 0.9% | 15.1 | 0 | 1 | 0 |
| I54A-Q58E | 1 | 1633 | 8 | 857 | 0.0013 | 0.1% | 0.9% | 15.1 | 0 | 1 | 0 |
| V82F-G73 | 1 | 1633 | 8 | 857 | 0.0013 | 0.1% | 0.9% | 15.1 | 0 | 1 | 0 |
| E34Q-M46I | 1 | 1633 | 8 | 857 | 0.0013 | 0.1% | 0.9% | 15.1 | 0 | 1 | 0 |
| I47V-G73 | 1 | 1633 | 7 | 858 | 0.0033 | 0.1% | 0.8% | 13.2 | 0 | 1 | 0 |
| G48V-91 | 1 | 1633 | 6 | 859 | 0.0084 | 0.1% | 0.7% | 11.3 | 0 | 1 | 0 |
| I54A-G73 | 1 | 1633 | 6 | 859 | 0.0084 | 0.1% | 0.7% | 11.3 | 0 | 1 | 0 |
| L24I-L76V | 1 | 1633 | 6 | 859 | 0.0084 | 0.1% | 0.7% | 11.3 | 0 | 1 | 0 |
| F53L-91 | 1 | 1633 | 6 | 859 | 0.0084 | 0.1% | 0.7% | 11.3 | 0 | 1 | 0 |
| L33F-67 | 2 | 1632 | 9 | 856 | 0.0018 | 0.1% | 1.0% | 8.5 | 0 | 1 | 0 |
| M46L-L76V | 2 | 1632 | 9 | 856 | 0.0018 | 0.1% | 1.0% | 8.5 | 0 | 1 | 0 |
| G48V-A71L | 2 | 1632 | 9 | 856 | 0.0018 | 0.1% | 1.0% | 8.5 | 0 | 1 | 0 |
| V82S-F53L | 2 | 1632 | 9 | 856 | 0.0018 | 0.1% | 1.0% | 8.5 | 0 | 1 | 0 |
| A71L-G73 | 1 | 1633 | 4 | 861 | 0.0517 | 0.1% | 0.5% | 7.6 | 0 | 1 | 0 |
| L33F-E34Q | 3 | 1631 | 10 | 855 | 0.0022 | 0.2% | 1.2% | 6.3 | 0 | 1 | 0 |
| M46L-V82S | 3 | 1631 | 10 | 855 | 0.0022 | 0.2% | 1.2% | 6.3 | 0 | 1 | 0 |
| G48V-V82S | 4 | 1630 | 12 | 853 | 0.0011 | 0.2% | 1.4% | 5.7 | 0 | 1 | 0 |
| A71L-L90M | 3 | 1631 | 9 | 856 | 0.0051 | 0.2% | 1.0% | 5.7 | 0 | 1 | 0 |
| E34Q-Q58E | 2 | 1632 | 6 | 859 | 0.0237 | 0.1% | 0.7% | 5.7 | 0 | 1 | 0 |
| 35-91 | 3 | 1631 | 8 | 857 | 0.0204 | 0.2% | 0.9% | 5.0 | 0 | 1 | 0 |
| I54V-A71L | 2 | 1632 | 5 | 860 | 0.0528 | 0.1% | 0.6% | 4.7 | 0 | 1 | 0 |
| V82F-V82S | 2 | 1632 | 5 | 860 | 0.0528 | 0.1% | 0.6% | 4.7 | 0 | 1 | 0 |
| L24I-E34Q | 2 | 1632 | 5 | 860 | 0.0528 | 0.1% | 0.6% | 4.7 | 0 | 1 | 0 |
| I54T-35 | 6 | 1628 | 14 | 851 | 0.0015 | 0.4% | 1.6% | 4.4 | 0 | 1 | 0 |
| E34Q-G73 | 3 | 1631 | 7 | 858 | 0.0383 | 0.2% | 0.8% | 4.4 | 0 | 1 | 0 |
| G48V-L24I | 4 | 1630 | 8 | 857 | 0.0295 | 0.2% | 0.9% | 3.8 | 0 | 1 | 0 |
| V82A-V82F | 2 | 1632 | 4 | 861 | 0.1909 | 0.1% | 0.5% | 3.8 | 0 | 1 | 0 |
| V82F-L24I | 2 | 1632 | 4 | 861 | 0.1909 | 0.1% | 0.5% | 3.8 | 0 | 1 | 0 |
| M46L-67 | 6 | 1628 | 12 | 853 | 0.0059 | 0.4% | 1.4% | 3.8 | 0 | 1 | 0 |
| M46I-67 | 11 | 1623 | 17 | 848 | 0.0048 | 0.7% | 2.0% | 2.9 | 0 | 0 | 0 |
| M46I-67 | 11 | 1623 | 17 | 848 | 0.0048 | 0.7% | 2.0% | 2.9 | 0 | 0 | 0 |
| M46L-I47V | 2 | 1632 | 3 | 862 | 0.3483 | 0.1% | 0.3% | 2.8 | 0 | 0 | 0 |
| E34Q-K43T | 2 | 1632 | 3 | 862 | 0.3483 | 0.1% | 0.3% | 2.8 | 0 | 0 | 0 |
| M46I-V82S | 11 | 1623 | 16 | 849 | 0.0129 | 0.7% | 1.8% | 2.7 | 0 | 0 | 0 |
| V82S-M46I | 11 | 1623 | 16 | 849 | 0.0129 | 0.7% | 1.8% | 2.7 | 0 | 0 | 0 |
| G73-67 | 15 | 1619 | 21 | 844 | 0.0041 | 0.9% | 2.4% | 2.6 | 0 | 0 | 0 |
| I54A-I54V | 5 | 1629 | 7 | 858 | 0.1242 | 0.3% | 0.8% | 2.6 | 0 | 0 | 0 |
| L90M-L24I | 5 | 1629 | 7 | 858 | 0.1242 | 0.3% | 0.8% | 2.6 | 0 | 0 | 0 |
| K43T-67 | 3 | 1631 | 4 | 861 | 0.2441 | 0.2% | 0.5% | 2.5 | 0 | 0 | 0 |
| G48V-F53L | 4 | 1630 | 5 | 860 | 0.2903 | 0.2% | 0.6% | 2.4 | 0 | 0 | 0 |
| I54V-E34Q | 12 | 1622 | 14 | 851 | 0.0596 | 0.7% | 1.6% | 2.2 | 0 | 0 | 0 |
| 35-67 | 21 | 1613 | 23 | 842 | 0.0161 | 1.3% | 2.7% | 2.2 | 0 | 0 | 0 |

TABLE 3-continued

ANALYSIS OF COMBINATIONS OF PAIRS OF MUTATIONS

| Mutation Pair | PS, mt | PS, wt | PR, mt | PR, wt | P value | % mt S | % mt R | % R/% S | P < 0.001 | Ratio > 3 | Ratio < 0.3 |
|---|---|---|---|---|---|---|---|---|---|---|---|
| M46I-M46L | 19 | 1615 | 20 | 845 | 0.0402 | 1.2% | 2.3% | 2.0 | 0 | 0 | 0 |
| M46L-M46I | 19 | 1615 | 20 | 845 | 0.0402 | 1.2% | 2.3% | 2.0 | 0 | 0 | 0 |
| M46L-E34Q | 4 | 1630 | 4 | 861 | 0.4596 | 0.2% | 0.5% | 1.9 | 0 | 0 | 0 |
| L10F-35 | 52 | 1582 | 49 | 816 | 0.0038 | 3.2% | 5.7% | 1.8 | 0 | 0 | 0 |
| A71V-67 | 27 | 1607 | 24 | 841 | 0.0734 | 1.7% | 2.8% | 1.7 | 0 | 0 | 0 |
| F53L-67 | 8 | 1626 | 7 | 858 | 0.4144 | 0.5% | 0.8% | 1.7 | 0 | 0 | 0 |
| E34Q-35 | 6 | 1628 | 5 | 860 | 0.5285 | 0.4% | 0.6% | 1.6 | 0 | 0 | 0 |
| L10I-67 | 39 | 1595 | 28 | 837 | 0.2412 | 2.4% | 3.2% | 1.4 | 0 | 0 | 0 |
| G48V-67 | 3 | 1631 | 2 | 863 | 1.0000 | 0.2% | 0.2% | 1.3 | 0 | 0 | 0 |

-N/A-: Not Applicable; results in division by zero.
The last 3 columns (P < 0.001, ratio > 3, ratio < 0.3) contain either a "1" if the condition at the top of the column (e.g., P < 0.001) is true and a "0" if the condition is false.

TABLE 4

Algorithm Construction and Application to the Training and Validation Data Sets

| | Number of samples | | | | % of samples | | |
|---|---|---|---|---|---|---|---|
| Rules | PT-S, GT-S | PT-R, GT-R | PT-R, GT-S | PT-S, GT-R[2] | PT-R, GT-S | PT-S, GT-R | Total Discordance |
| Training Data Set[1] | | | | | | | |
| Starting mutations | 1635 | 1698 | 865 | 216 | 19.6 | 4.9 | 24.5 |
| Add 82F, 84C, 54AST + 2mut* | 1602 | 1892 | 672 | 237 | 15.2 | 5.4 | 20.6 |
| Add 33F/82A + 2mut* | 1586 | 2021 | 543 | 245 | 12.3 | 5.6 | 17.9 |
| Add 46IL + 47V, 54V, 71L, 76V, or 82A +2mut* | 1341 | 2302 | 262 | 388 | 5.9 | 8.8 | 14.7 |
| Validation Data Set[1] | | | | | | | |
| Starting mutations | 957 | 419 | 209 | 50 | 12.8 | 3.1 | 15.9 |
| Final algorithm | 910 | 556 | 72 | 97 | 4.4 | 5.9 | 10.3 |

[1] 4414 samples in the training data set; 1634 samples in the validation data set that were not used to derive the algorithm
[2] mixtures not accounted for (i.e., some discordance due to mixtures, not inaccuracy of rules)
*at least 2 secondary mutations required in addition to listed requirements.

TABLE 5

Primary and Secondary Mutations Associated With Amprenavir Resistance

| Primary | Secondary |
|---|---|
| I50V; V32I; I54L; I54M; I84A; I84V | L10I, F, R, or V; K20I, M, R, or T; L33F, M36I or L; M46I, L, or V; I47V; G48M, S, or V; I54A, L, M, S, T, or V; L63P, S, A, T, Q, or C; A71I, L, V, or T; V82A, F, T, or S; L90M |

What is claimed is:

1. A method for determining whether a human immunodeficiency virus type 1 virus (HIV-1) has an increased likelihood of having a reduced susceptibility to treatment with amprenavir, comprising:

detecting the presence or absence of a mutation in a protease associated with reduced susceptibility to treatment with amprenavir at amino acid position 11, 34, 76, 83, 91 or 95 of an amino acid sequence of said protease, wherein the mutation at position 11 is isoleucine (I) or leucine (L), the mutation at amino acid position 34 is glutamine (Q), the mutation at position 76 is valine (V), the mutation at position 83 is aspartic acid (D), the mutation at position 91 is alanine (A), valine (V), or serine (S), and the mutation at position 95 is phenylalanine (F), and determining whether the HIV-1 has an increased likelihood of having a reduced susceptibility to treatment with amprenavir, wherein the presence of said mutation indicates that the HIV-1 has an increased likelihood of having a reduced susceptibility to treatment with amprenavir, and wherein the level of susceptibility, mutations, and amino acid position number are compared to SEQ ID NO:1, the protease sequence of the NL4-3 reference strain.

2. The method of claim 1, wherein the presence or absence of a mutation at position 11 of said protease is detected.

3. The method of claim 1, wherein the presence or absence of a mutation at position 76 of said protease is detected.

4. The method of claim 1, wherein the presence or absence of a mutation at position 91 of said protease is detected.

5. The method of claim 1, wherein the presence or absence of a mutation at position 95 of said protease is detected.

6. The method of claim 1, wherein the presence or absence of a mutation at position 83 of said protease is detected.

7. The method of claim 1, wherein the method comprises detecting the presence or absence of a mutation associated with reduced susceptibility to treatment with amprenavir at each one of at least 2 of the amino acid positions.

8. The method of claim 1, further comprising detecting the presence or absence of a mutation in at least one amino acid position selected from the group consisting of position 32, 33, 43, 46, 48, 54, 58, 71, 82, and 84, wherein the mutation at position 32 is isoleucine (I); the mutation at position 33 is phenylalanine (F); the mutation at position 43 is threonine (T); the mutation at position 46 is isoleucine (I), leucine (L), or valine (V); the mutation at position 48 is methionine (M), serine (S), or valine (V); the mutation at position 54 is alanine (A), serine (S), threonine (T), leucine (L), valine (V), or methionine (M); the mutation at position 58 is glutamic acid (E); the mutation at position 71 is leucine (L), isoleucine (I), valine (V), or threonine (T); the mutation at position 82 is alanine (A), phenylalanine (F), serine (S), or threonine (T), and the mutation at position 84 is alanine (A) or cysteine (C), wherein the presence of said mutation indicates that the HIV-1 has an increased likelihood of having reduced susceptibility to treatment with amprenavir, and wherein the level of susceptibility, mutations, and amino acid position number are compared to SEQ ID NO:1, the protease sequence of the NL4-3 reference strain.

9. The method of claim 8, wherein the presence or absence of a mutation at position 33 of said protease is detected.

10. The method of claim 8, wherein the presence or absence of a mutation at position 48 of said protease is detected.

11. The method of claim 8, wherein the presence or absence of a mutation at position 54 of said protease is detected.

12. The method of claim 8, wherein the presence or absence of a mutation at position 71 of said protease is detected.

13. The method of claim 8, wherein the presence or absence of a mutation at position 82 of said protease is detected.

14. The method of claim 8, wherein the presence or absence of a mutation at position 84 of said protease is detected.

15. The method of claim 8, wherein the presence or absence of a mutation at position 43 of said protease is detected.

16. The method of claim 8, wherein the presence or absence of a mutation at position 54 of said protease is detected.

17. The method of claim 8, wherein the presence or absence of a mutation at position 58 of said protease is detected.

18. The method of claim 8, wherein the method comprises detecting the presence or absence of a mutation associated with reduced susceptibility to treatment with amprenavir at each one of at least 3 of the amino acid positions.

19. The method of claim 1, wherein the method comprises detecting the presence or absence of a mutation associated with reduced susceptibility to treatment with amprenavir at each one of at least 3 of the amino acid positions.

20. The method of claim 1, wherein the method comprises detecting the presence or absence of a mutation associated with reduced susceptibility to treatment with amprenavir at each one of at least 4 of the amino acid positions.

21. The method of claim 1, wherein the method comprises detecting the presence or absence of a mutation associated with reduced susceptibility to treatment with amprenavir at each one of at least 5 of the amino acid positions.

22. The method of claim 1, wherein the method comprises detecting the presence or absence of a mutation associated with reduced susceptibility to treatment with amprenavir at all of the amino acid positions.

23. The method of claim 8, wherein the method comprises detecting the presence of absence of a mutation associated with reduced susceptibility to treatment with amprenavir at each one of at least 4 of the amino acid positions.

24. The method of claim 8, wherein the method comprises detecting the presence of absence of a mutation associated with reduced susceptibility to treatment with amprenavir at each one of at least 5 of the amino acid positions.

25. The method of claim 8, wherein the method comprises detecting the presence of absence of a mutation associated with reduced susceptibility to treatment with amprenavir at each one of at least 6 of the amino acid positions.

26. The method of claim 8, wherein the method comprises detecting the presence of absence of a mutation associated with reduced susceptibility to treatment with amprenavir at each one of at least 7 of the amino acid positions.

27. The method of claim 8, wherein the method comprises detecting the presence of absence of a mutation associated with reduced susceptibility to treatment with amprenavir at each one of at least 8 of the amino acid positions.

28. The method of claim 8, wherein the method comprises detecting the presence of absence of a mutation associated with reduced susceptibility to treatment with amprenavir at each one of at least 9 of the amino acid positions.

29. The method of claim 8, wherein the method comprises detecting the presence of absence of a mutation associated with reduced susceptibility to treatment with amprenavir at each one of at least 10 of the amino acid positions.

30. The method of claim 8, wherein the method comprises detecting the presence of absence of a mutation associated with reduced susceptibility to treatment with amprenavir at each one of at least 11 of the amino acid positions.

31. The method of claim 8, wherein the method comprises detecting the presence of absence of a mutation associated with reduced susceptibility to treatment with amprenavir at each one of at least 12 of the amino acid positions.

32. The method of claim 8, wherein the method comprises detecting the presence of absence of a mutation associated with reduced susceptibility to treatment with amprenavir at each one of at least 13 of the amino acid positions.

33. The method of claim 8, wherein the method comprises detecting the presence of absence of a mutation associated with reduced susceptibility to treatment with amprenavir at each one of at least 14 of the amino acid positions.

34. The method of claim 8, wherein the method comprises detecting the presence of absence of a mutation associated with reduced susceptibility to treatment with amprenavir at each one of at least 15 of the amino acid positions.

35. The method of claim 8, wherein the method comprises detecting the presence of absence of a mutation associated with reduced susceptibility to treatment with amprenavir at all of the amino acid positions.

\* \* \* \* \*

UNITED STATES PATENT AND TRADEMARK OFFICE
CERTIFICATE OF CORRECTION

PATENT NO. : 7,993,824 B2  Page 1 of 1
APPLICATION NO. : 10/612603
DATED : August 9, 2011
INVENTOR(S) : Colombe Chappey et al.

It is certified that error appears in the above-identified patent and that said Letters Patent is hereby corrected as shown below:

Column 31, Line 59, After "This list included: L10F," please delete "L10F,", please insert -- L10I, --.
Column 51, Line 35, After "detecting the presence", please delete "of", please insert -- or --.
Column 51, Line 39, After "detecting the presence", please delete "of", please insert -- or --.
Column 51, Line 43, After "detecting the presence", please delete "of", please insert -- or --.
Column 52, Line 4, After "detecting the presence", please delete "of", please insert -- or --.
Column 52, Line 8, After "detecting the presence", please delete "of", please insert -- or --.
Column 52, Line 12, After "detecting the presence", please delete "of", please insert -- or --.
Column 52, Line 16, After "detecting the presence", please delete "of", please insert -- or --.
Column 52, Line 20, After "detecting the presence", please delete "of", please insert -- or --.
Column 52, Line 24, After "detecting the presence", please delete "of", please insert -- or --.
Column 52, Line 28, After "detecting the presence", please delete "of", please insert -- or --.
Column 52, Line 32, After "detecting the presence", please delete "of", please insert -- or --.
Column 52, Line 36, After "detecting the presence", please delete "of", please insert -- or --.
Column 52, Line 40, After "detecting the presence", please delete "of", please insert -- or --.

Signed and Sealed this
Twentieth Day of December, 2011

David J. Kappos
*Director of the United States Patent and Trademark Office*

```
                        SEQUENCE LISTING

<160> NUMBER OF SEQ ID NOS: 2

<210> SEQ ID NO 1
<211> LENGTH: 99
<212> TYPE: PRT
<213> ORGANISM: Human immunodeficiency virus

<400> SEQUENCE: 1

Pro Gln Ile Thr Leu Trp Gln Arg Pro Leu Val Thr Ile Lys Ile Gly
1               5                   10                  15

Gly Gln Leu Lys Glu Ala Leu Leu Asp Thr Gly Ala Asp Asp Thr Val
            20                  25                  30
```

-continued

```
Leu Glu Glu Met Asn Leu Pro Gly Arg Trp Lys Pro Lys Met Ile Gly
         35                  40                  45

Gly Ile Gly Gly Phe Ile Lys Val Arg Gln Tyr Asp Gln Ile Leu Ile
     50                  55                  60

Glu Ile Cys Gly His Lys Ala Ile Gly Thr Val Leu Val Gly Pro Thr
 65              70                  75                  80

Pro Val Asn Ile Ile Gly Arg Asn Leu Leu Thr Gln Ile Gly Cys Thr
                 85                  90                  95

Leu Asn Phe

<210> SEQ ID NO 2
<211> LENGTH: 297
<212> TYPE: DNA
<213> ORGANISM: Human immunodeficiency virus

<400> SEQUENCE: 2
cctcagatca ctctttggca gcgacccctc gtcacaataa agatagggggg gcaattaaag        60 gaagctctat tagatacagg agcagatgat acagtattag aagaaatgaa tttgccagga       120
agatggaaac caaaaatgat aggggggaatt ggaggtttta tcaaagtaag acagtatgat       180
cagatactca tagaaatctg cggacataaa gctataggta cagtattagt aggacctaca       240
cctgtcaaca taattggaag aaatctgttg actcagattg gctgcacttt aaatttt          297
```